United States Patent
Soto et al.

(10) Patent No.: US 11,873,332 B2
(45) Date of Patent: Jan. 16, 2024

(54) LYOPHILIZED FORMULATION OF A MONOCLONAL ANTIBODY AGAINST TRANSTHYRETIN

(71) Applicant: Novo Nordisk A/S, Bagsvaerd (DK)

(72) Inventors: Joseph Alexander Soto, San Francisco, CA (US); Andrea Hawe, Munich (DE); Ruedeeporn Tantipolphan, Munich (DE); Stefan Heindl, Perchtoldsdorf (AT)

(73) Assignee: NOVO NORDISK A/S, Bagsvaerd (DK)

( * ) Notice: Subject to any disclaimer, the term of this patent is extended or adjusted under 35 U.S.C. 154(b) by 622 days.

(21) Appl. No.: 16/767,994

(22) PCT Filed: Nov. 28, 2018

(86) PCT No.: PCT/US2018/062902
§ 371 (c)(1),
(2) Date: May 28, 2020

(87) PCT Pub. No.: WO2019/108689
PCT Pub. Date: Jun. 6, 2019

(65) Prior Publication Data
US 2020/0362023 A1 Nov. 19, 2020

Related U.S. Application Data

(60) Provisional application No. 62/592,294, filed on Nov. 29, 2017.

(51) Int. Cl.
| | |
|---|---|
| A61K 39/395 | (2006.01) |
| C07K 16/18 | (2006.01) |
| A61K 9/19 | (2006.01) |
| A61K 47/10 | (2017.01) |
| A61K 47/18 | (2017.01) |
| A61K 47/26 | (2006.01) |
| A61K 9/00 | (2006.01) |
| A61K 45/06 | (2006.01) |
| A61K 39/00 | (2006.01) |

(52) U.S. Cl.
CPC ............... *C07K 16/18* (2013.01); *A61K 9/19* (2013.01); *A61K 47/10* (2013.01); *A61K 47/183* (2013.01); *A61K 47/26* (2013.01); *A61K 9/0019* (2013.01); *A61K 45/06* (2013.01); *A61K 2039/545* (2013.01); *C07K 2317/24* (2013.01); *C07K 2317/56* (2013.01)

(58) Field of Classification Search
None
See application file for complete search history.

(56) References Cited

U.S. PATENT DOCUMENTS

| | | | |
|---|---|---|---|
| 5,530,101 A | 6/1996 | Queen et al. | |
| 8,871,447 B2 | 10/2014 | Kayed et al. | |
| 9,534,048 B2 | 1/2017 | Chakrabartty et al. | |
| 9,535,076 B2 | 1/2017 | Kayed et al. | |
| 9,637,552 B2 | 5/2017 | Cashman et al. | |
| 9,731,292 B2 | 8/2017 | Ermantraut et al. | |
| 9,879,080 B2 | 1/2018 | Nijjar et al. | |
| 10,253,100 B2 | 4/2019 | Igawa et al. | |
| 10,464,999 B2 | 11/2019 | Liu et al. | |
| 10,494,426 B2 | 12/2019 | Nijjar et al. | |
| 10,618,965 B2 | 4/2020 | Igawa et al. | |
| 10,633,433 B2 | 4/2020 | Nijjar et al. | |
| 10,669,330 B2 | 6/2020 | Liu et al. | |
| 10,906,967 B2 | 2/2021 | Nijjar et al. | |
| 11,028,158 B2 | 6/2021 | Liu et al. | |
| 2002/0019335 A1 | 2/2002 | Solomon et al. | |
| 2006/0280733 A1 | 12/2006 | Kayed et al. | |
| 2007/0110750 A1 | 5/2007 | Glabe et al. | |
| 2010/0233176 A1 | 9/2010 | Cashman et al. | |
| 2011/0200609 A1 | 8/2011 | Glabe et al. | |
| 2013/0344088 A1* | 12/2013 | Cosenza | A61K 39/39591 424/172.1 |
| 2014/0056904 A1 | 2/2014 | Chakrabartty et al. | |
| 2015/0353630 A1 | 12/2015 | Igawa et al. | |
| 2016/0039916 A1 | 2/2016 | Jiang et al. | |
| 2016/0251418 A1 | 9/2016 | Liu et al. | |
| 2016/0257736 A1 | 9/2016 | Nijjar et al. | |
| 2016/0257737 A1 | 9/2016 | Liu et al. | |
| 2016/0340419 A1 | 11/2016 | Torikai et al. | |
| 2016/0340420 A1 | 11/2016 | Zhang et al. | |
| 2016/0347832 A1 | 12/2016 | Hosoi et al. | |
| 2016/0355576 A1 | 12/2016 | Grimm et al. | |
| 2017/0015737 A1 | 1/2017 | Nijar et al. | |
| 2017/0058023 A1 | 3/2017 | Liu et al. | |
| 2017/0121398 A1 | 5/2017 | Nijjar et al. | |

(Continued)

FOREIGN PATENT DOCUMENTS

| | | |
|---|---|---|
| CA | 2886254 A1 | 4/2014 |
| CN | 103492882 A | 1/2014 |

(Continued)

OTHER PUBLICATIONS

Bergström, et al., "Surface exposed epitopes and structural heterogeneity of in vivo formed transthyretin amyloid fibrils," Biophysical Research Communications, 348:532-539 (2006).

(Continued)

*Primary Examiner* — Yunsoo Kim

(74) *Attorney, Agent, or Firm* — Alston & Bird LLP

(57) ABSTRACT

The invention provides antibody formulations and methods useful for prophylaxis or treatment of transthyretin-related amyloidosis.

12 Claims, No Drawings

Specification includes a Sequence Listing.

(56) References Cited

U.S. PATENT DOCUMENTS

| | | |
|---|---|---|
| 2018/0201670 A1 | 7/2018 | Nijjar et al. |
| 2020/0055929 A1 | 2/2020 | Nijar et al. |
| 2020/0087386 A1 | 3/2020 | Liu et al. |
| 2020/0249244 A1 | 8/2020 | Salmans et al. |
| 2020/0277361 A1 | 9/2020 | Nijjar et al. |
| 2020/0331992 A1 | 10/2020 | Salmans et al. |
| 2021/0188956 A1 | 6/2021 | Nijar et al. |

FOREIGN PATENT DOCUMENTS

| | | |
|---|---|---|
| CN | 106255702 A | 12/2016 |
| EP | 1185296 B1 | 1/2011 |
| EP | 2044443 B1 | 1/2011 |
| EP | 1578361 B1 | 4/2011 |
| EP | 2552955 B1 | 5/2017 |
| EP | 2679681 B1 | 8/2019 |
| EP | 2698431 B1 | 9/2020 |
| EP | 2857419 B1 | 1/2021 |
| JP | 2010-195710 A | 9/2010 |
| JP | 2014-510907 A | 5/2014 |
| JP | 2016-514091 A | 5/2016 |
| WO | WO 2004/024090 A3 | 3/2004 |
| WO | WO 2005/025516 A2 | 3/2005 |
| WO | WO 2006/108234 A1 | 10/2006 |
| WO | WO 2008/005455 A3 | 1/2008 |
| WO | WO 2010/012004 A2 | 1/2010 |
| WO | WO 2010/030203 A1 | 3/2010 |
| WO | WO 2010/040209 A1 | 4/2010 |
| WO | WO 2010/099612 A1 | 9/2010 |
| WO | WO 2014/058924 A2 | 4/2014 |
| WO | WO 2014/124334 A2 | 8/2014 |
| WO | WO 2014/142334 A1 | 9/2014 |
| WO | WO 2015/010118 A2 | 1/2015 |
| WO | WO 2015/092077 A1 | 6/2015 |
| WO | WO 2015/115331 A1 | 8/2015 |
| WO | PCT/IB2016/050414 | 1/2016 |
| WO | PCT/IB2016/050415 | 1/2016 |
| WO | PCT/IB2016/050416 | 1/2016 |
| WO | WO 2016/033326 A2 | 3/2016 |
| WO | WO 2016/120809 A1 | 8/2016 |
| WO | WO 2016/120810 A1 | 8/2016 |
| WO | WO 2016/120811 A1 | 8/2016 |
| WO | PCT/IB2017/053984 | 6/2017 |
| WO | PCT/IB2017/053987 | 6/2017 |
| WO | PCT/IB2017/053991 | 6/2017 |
| WO | WO 2018/007922 A2 | 1/2018 |
| WO | WO 2018/007923 A2 | 1/2018 |
| WO | WO 2018/007924 A2 | 1/2018 |
| WO | PCT/US2018/054720 | 10/2018 |
| WO | PCT/US2018/054723 | 10/2018 |
| WO | PCT/US2018/062902 | 11/2018 |
| WO | WO 2019/071205 A1 | 4/2019 |
| WO | WO 2019/071206 A1 | 4/2019 |
| WO | WO 2019/108689 A1 | 6/2019 |
| WO | PCT/US2021/018632 | 2/2021 |
| WO | WO 2021/168156 A1 | 8/2021 |

OTHER PUBLICATIONS

Goldsteins, et al., "Exposure of cryptic epitopes on transthyretin only in amyloid and in amyloidogenic mutants," Proc. Natl. Acad. Sci. USA, vol. 96, pp. 3108-3113 (Mar. 1999).

Gustavsson, et al., "Antigenic Mapping of Transthyretin Purified from Plasma and Amyloid Fibrils and within in Situ Tissue Localizations," American Journal of Pathology, vol. 144, No. 6, pp. 1301-1311 (Jun. 1994).

Redondo, et al., "Search for Intermediate Structures in Transthyretin Fibrillogenesis: Soluble Tetrameric Tyr78Phe TTR Expresses a Specific Epitope Present Only in Amyloid Fibrils," J. Mol. Biol., 304, 461-470 (2000).

Terazaki, et al., "Immunization in familial amyloidotic polyneuropathy: counteracting deposition by immunization with a Y78F TTR mutant," Laboratory Investigation, 86, 23-31 (2006).

Phay, et al., "Transthyretin Aggregate-Specific Antibodies Recognize Cryptic epitopes on Patient-Derived Amyloid Fibrils," Rejuvenation Research, vol. 17, No. 2, pp. 97-105 (2014).

PCT/IB2016/050415 International Search Report and Written Opinion dated Mar. 24, 2016.

Leger, et al., "Humanization of Antibodies," Molecular Medicine and Medicinal Chemistry, pp. 1-23, (Jan. 1, 2011).

Almagro, et al., "Humanization of antibodies," Frontiers in Bioscience, 12:1619-1633, (Jan. 1, 2008).

PCT/IB2016/050414 International Search Report and Written Opinion dated Apr. 25, 2016.

PCT/IB2016/050416 International Search Report and Written Opinion dated May 18, 2016.

Hernandez, et al., "Identification of new pathogenic candidates for diabetic mascular edema using fluorescence-based difference gel electrophoresis analysis", Diabetes Metab Res Rev, 29:499-506 (2013). [Retrieved from the Internet Mar. 8, 2017: https://www.researchgate.net/publication/236140050_Identification_of_new_pathogenic_candidates_for_diabetic_macular_edema_using_fluorescence-based_difference_gel_electrophoresis_analysis].

Dias-Santos, et al., "Macular and Iptic disc dedma and retinal vascular leakage in familal amyloid polyneuropathy with a transthyretin Val30Met mutation: a case report", J Med Case Rep, 8:327 (Oct. 4, 2014).

U.S. Appl. No. 15/009,662 Restriction Requirement dated Sep. 20, 2016.

U.S. Appl. No. 15/009,666 Restriction Requirement dated Sep. 20, 2016.

Adekar, et al., "Inherent Anti-amyloidogenic Activity of Human Immunoglobulin γ Heavy Chains," J Biol Chem, 285(2):1066-74, (2010).

Cardoso, et al., "Transthyretin Fibrillogenesis Entails the Assembly of Monomers: A Molecular Model for in Vitro Assembled Transthyretin Amyloid-like Fibrils," J Mol Biol, 317:683-95, (2002).

Chen, et al., "Endoplasmic Reticulum Proteostasis Influences the Oligomeric State of an Amyloidogenic Protein Secreted from Mammalian Cells," Cell Chem Biol, 23:1282-1293, (2016).

Galant, et al., "Substoichiometric inhibition of transthyretin misfolding by immune-targeting sparsely populated misfolding intermediates: a potential diagnostic and therapeutic for TTR amyloidoses," Sci Rep, 6:1-11, srep 25080, Apr. 28, 2016. [Retrieved from the Internet Feb. 27, 2017: <www.nature.com/scientificreports>].

Higaki, et al., "Novel conformation-specific monoclonal antibodies against amyloidogenic forms of transthyretin," Amyloid, 23(2):86-97, (2016).

Jiang, et al., "An Engineered Transthyretin Monomer that Is Nonamyloidogenic, Unless It Is Partially Denatured," Biochemistry, 40(38):11442-11452, (2011).

Johnson, et al., "The Transthyretin Amyloidoses: From Delineating the Molecular Mechanism of Aggregation Linked to Pathology to a Regulatory-Agency-Approved Drug," J Mol Biol, 421:185-203, (2012).

Lai, et al., "The Acid-Mediated Denaturation Pathway of Transthyretin Yields a Conformational Intermediate That Can Self-Assemble into Amyloid," Biochemistry, 35(20):6470-6482, (1996).

Lashuel, et al., "Characterization of the Transthyretin Acid Denaturation Pathways by Analytical Ultracentrifugation: Implications for Wild-Type, V30M, and L55P Amyloid Fibril Formation," Biochemistry, 37(51):17851-17864, (1998).

Levites, et al., "A Human Monoclonal IgG That Binds Aβ Assemblies and Diverse Amyloids Exhibits Anti-Amyloid Activities In Vitro and In Vivo," J Neurosci, 35(16):6265-6276, (2015).

McCutchen, et al., "Comparison of Lethal and Nonlethal Transthyretin Variants and Their Relationship to Amyloid Disease," Biochemistry, 34(41):13527-13536, (1995).

Miroy, et al., "Inhibiting transthyretin amyloid fibril formation via protein stabilization," Proc Natl Acad Sci USA, 93:15051-15056, (1996).

O'Nuallain, et al., "Localization of a Conformational Epitope Common to Non-Native and Fibrillar Immunoglobulin Light Chains," Biochemistry, 46(5):1240-1247, (2007).

(56) References Cited

OTHER PUBLICATIONS

O'Nuallain, et al., "Conformational Abs recognizing a generic amyloid fibril epitope," Proc Natl Acad Sci USA, 99(3):1485-1490, (2002).
O'Nuallain, et al., "Anti-amyloidogenic Activity of IgGs Contained in Normal Plasma," J Clin Immunol, 30 Suppl 1:S37-S42, (2010).
Phay, et al., "IgG Conformer's Binding to Amyloidogenic Aggregates," PLOS One, 10(9):1-25, (2015).
Planque, et al., "Physiological IgM Class Catalytic Antibodies Selective for Transthyretin Amyloid," J Biol Chem, 289(19):13243-13258, (2014).
Planque, et al., "Specific Amyloid B Clearance by a Catalytic Antibody Construct," J Biol Chem, 290(16):10229-10241, (2015).
Quintas, et al., "Tetramer Dissociation and Monomer Partial Unfolding Precedes Protofibril Formation in Amyloidogenic Transthyretin Variants," J Biol Chem, 276(29):27207-27213, (2001).
Su, et al., "Antibody therapy for familial amyloidotic polyneuropathy," Amyloid, 19(51):45-46, (2012).
Hosoi, et al., "Novel Antibody for the Treatment of Transthyretin Amyloidosis," J Biol Chem, 291(48):25096-25105, (2016).
U.S. Appl. No. 15/009,667 Restriction Requirement dated Dec. 30, 2016.
U.S. Appl. No. 15/009,662 Non-Final Office Action dated Mar. 7, 2017.
Paul, "Fundamental Immunology" textbook under the heading "Fv Structure and Diversity in Three Dimensions," pp. 292-295, (1993).
Rudikoff, et al., "Single amino acid substitution altering antigen-binding specificity," Proc Natl Acad Sci USA, 79(6):1979-1983, (1982).
U.S. Appl. No. 15/009,662 Examiner Initiated Interview Summary dated Mar. 7, 2017.
U.S. Appl. No. 15/009,666 Non-Final Office Action dated Mar. 6, 2017.
U.S. Appl. No. 15/009,666 Examiner Initiated Interview Summary dated Mar. 6, 2017.
U.S. Appl. No. 15/009,667 Non-Final Office Action dated Mar. 29, 2017.
U.S. Appl. No. 15/201,423 Restriction Requirement dated Jun. 5, 2017.
U.S. Appl. No. 15/201,416 Restriction Requirement dated May 31, 2017.
U.S. Appl. No. 15/201,429 Restriction Requirement dated Jul. 3, 2017.
PCT/IB2016/050416 International Preliminary Report on Patentability dated Aug. 10, 2017.
PCT/IB2016/050415 International Preliminary Report on Patentability dated Aug. 10, 2017.
PCT/IB2016/050414 International Preliminary Report on Patentability dated Aug. 1, 2017.
U.S. Appl. No. 15/201,423 Non-Final Office Action dated Oct. 19, 2017.
Sharma, et al., "Identification of Autoantibodies against Transthyretin for the Screening and Diagnosis of Rheumatoid Arthritis", PLoS One, vol. 9, Issue 4, (Apr. 2014).
PCT/IB2017/053991 Invitation to Pay Additional Fees mailed Nov. 2, 2017.
U.S. Appl. No. 15/201,429 Non-Final Office Action dated Nov. 14, 2017.
PCT/IB2017/053991 International Search Report and Written Opinion dated Jan. 17, 2018.
PCT/IB2017/053984 International Search Report and Written Opinion dated Jan. 2, 2018.
PCT/IB2017/053987 International Search Report and Written Opinion dated Jan. 31, 2018.
U.S. Appl. No. 15/201,429 Final Office Action dated Jul. 9, 2018.
U.S. Appl. No. 15/201,423 Notice of Allowance and Examiner Initiated Interview Summary dated Jun. 13, 2018.
U.S. Appl. No. 15/201,429 Advisory Action dated Sep. 17, 2018.
U.S. Appl. No. 15/201,423 Notice of Allowance and Examiner Initiated Interview Summary dated Oct. 12, 2018.

PCT/IB2017/053987 International Preliminary Report on Patentability dated Jan. 8, 2019.
PCT/IB2017/053991 International Preliminary Report on Patentability dated Jan. 8, 2019.
PCT/IB2017/053984 International Preliminary Report on Patentability dated Jan. 8, 2019.
PCT/US2018/054723 International Search Report and Written Opinion dated Jan. 3, 2018.
Ionis Pharmaceuticals Announces Phase 3 NEURO-TTR Study of Inotersen (IONIS-TTRRx) Meets Both Primary Endpoints, Press Release, Carlsbad California, May 15, 2017.
U.S. Appl. No. 15/201,423 Notice of Allowance and Examiner Initiated Interview Summary dated Mar. 6, 2019.
PCT/US2018/062902 International Search Report and Written Opinion dated Apr. 7, 2019.
PCT/US2018/054720 International Search Report and Written Opinion dated Feb. 12, 2019.
Schonhoft, et al., "Peptide probes detect misfolded transthyretin oligomers in plasma of hereditary amyloidosis patients," Sci. Tranl. Med., 9, eaam 7621, (2017).
U.S. Appl. No. 15/201,429 Non-Final Office Action dated Mar. 5, 2019.
U.S. Appl. No. 15/861,600 Notice of Allowance and Examiner Initiated Interview Summary dated Mar. 18, 2019.
U.S. Appl. No. 15/201,423 Notice of Allowance dated Jun. 12, 2019.
Damas, et al., "Review: TTR Amyloidosis—Structural Features Leading to Protein Aggregation and Their Implications on Therapeutic Strategies," Journal of Structural Biology, 120, 290-299, (2000).
U.S. Appl. No. 16/129,618 Non-Final Office Action and Interview Summary dated Aug. 22, 2019.
Carvalho, et al., "Liver Transplantation in Transthyretin Amyloidosis: Issues and Challenges," Liver Transplantation, 21:282-292, (2015).
Murray, et al., "Physiological consequences of changes in the primary structure," Human Biochemistry, vol. 1, p. 34, right column, (1993).
U.S. Appl. No. 15/861,600 Notice of Allowance dated Jul. 25, 2019.
U.S. Appl. No. 15/201,429 Notice of Allowance and Interview Summary dated Sep. 25, 2019.
U.S. Appl. No. 15/201,429 Notice of Allowance dated Jan. 23, 2020.
U.S. Appl. No. 16/129,618 Notice of Allowance and Interview Summary dated Jan. 23, 2020.
Ando, et al., "Toransusairechin up-to-date," Rinshokagaku, vol. 37, pp. 375-382, (2008) English abstract.
EP 16702812.5 Third Party Observation submitted Jan. 31, 2020.
Prothena Corporation plc news release, "Prothena Discontinues Development of NEOD001 for AL Amyloidosis," Globe NewsW RE, Apr. 23, 2018.
PCT/US2018/054723 International Preliminary Report on Patentability dated Apr. 16, 2020.
PCT/US2018/054720 International Preliminary Report on Patentability dated Apr. 16, 2020.
PCT/US2018/062902 International Preliminary Report on Patentability dated Jun. 2, 2020.
Chen, et al., Yearbook of Biotechnology Development, Military Medical Science Press, p. 115, published on Dec. 31, 2014, including a translation of the related Chinese Office Action dated Aug. 4, 2020, in Chinese application No. 2016800158008 providing a brief statement of relevance.
Liu, et al., New Concept and Clinical Practice of Oncology, p. 291, China Medical Science Press, published on Dec. 31, 1994, including a translation of the related Chinese Office Action dated Aug. 4, 2020, in Chinese application No. 2016800158008 providing a brief statement of relevance.
Wang, Antibody Technology, Military Medical Science Press, p. 129, published on Mar. 31, 2009, including a translation of the related Chinese Office Action dated Aug. 4, 2020, in Chinese application No. 2016800158008 providing a brief statement of relevance.
Zhang, Essential Medical Immunology, Sichuan University Press, p. 340, published on May 31, 2007, including a translation of the

(56) References Cited

OTHER PUBLICATIONS related Chinese Office Action dated Aug. 4, 2020, in Chinese application No. 2016800158008 providing a brief statement of relevance.
NCBI: CAA75032.1, published on Aug. 19, 1998; PIR: SS2059, published on Sep. 8, 2000.
U.S. Appl. No. 16/669,375 Notice of Allowance and Interview Summary dated Sep. 18, 2020.
U.S. Appl. No. 16/789,319 Non-Final Office Action dated Dec. 3, 2020.
U.S. Appl. No. 16/584,634 Notice of Allowance and Examiner Interview Summary dated Feb. 5, 2021.
U.S. Appl. No. 16/753,307 Restriction Requirement dated Apr. 26, 202.
PCT/US2021/018632 International Search Report and Written Opinion dated May 7, 2021.
Akasaki, et al., "Transthyretin Deposition in Articular Cartilage," Arthritis & Rheumatology, vol. 67, No. 8, pp. 2097-2107, (Aug. 2015).
Clement, et al., "Autoimmune response to transthyretin in juvenile idiopathic arthritis," JCI Insight, (2): e85633, (2016).
DeGregorio, et al., Left Atrial Morphology, Size and Function in Patients With Transthyretin Cardiac Amyloidosis and Primary Hypertrophic Cardiomyopathy: Circulation Journal, 80: 1830-1837, (2016).
Gu, et al., Clinical and laboratory characteristics of patients having amyloidogenic transthyretin deposition in osteoarthritic knee joints, J. Zhejiang Unvi-Sci B (Biomed and Biotechnol), 15(1):92-99, (2014).
Mullins, et al., "Drusen associated with aging and age-related macular degeneration contain proteins common to extracellular deposits associated with atherosclerosis, elastosis, amyloidosis, and dense deposit disease," The FASEB Journal, vol. 14, pp. 836-846, (May 2000).
Sueyoski, et al., "Wild-type transthyretin-derived amyloidosis in various ligaments and tendons," Human Pathology, 42, 1259-1264, (2011).
Takanashi, et al., "Synovial deposition of wild-type transthyretin-derived amyloid in knee joint osteroarthritis patients," Amyloid, 20(3): 151-155, (2013).
Takinami, et al., "Identification of Potential Prognostic Markers for Knee Osteoarthritis by Serum Proeomic Analysis," Biomarker Insights, 8, 85-95, (2013).
Westermark, et al., "Transthyretin-derived amyloidosis: Probably a common cause of lumbar spinal stenosis," Upsala Journal of Medical Sciences, 119: 223228, (2014).
Yanagisawa, et al., "Amyloid deposits derived from transthyretin in the ligamentum flavum as related to lumbar spinal canal stenosis," Modern Pathology, 28, 201-207, (2015).
Ni, et al., "Transthyretin as a potential serological marker for the diagnosis of patients with early rheumatoid arthritis," Clin Exp Rheumatol, 31(3): 394-399, (2013).
"Synovial deposition of wild-type transthyretin-derived amyloid in knee joint osteoarthritis patients", Shinshu Medical Journal, vol. 62, No. 5, p. 329-330, (2014).
U.S. Appl. No. 16/753,307 Non-Final Office Action dated Jul. 14, 2021.
Kussie, et al., "A Single Engineered Amino Acid Substitution Changes Antibody Fine Specificity," J Immunonol, 152(1): 146-152, (1994).
Sinai, "Rotator Cuff Injury," Accessed from cedars-sinai.org on Jul. 9, 2021, (2021).
Saelices, et al., "Uncovering the Mechanism of Aggregation of Human Transthyretin," Journal of Biological Chemistry, vol. 290, No. 48, pp. 28932-28943, (Nov. 27, 2015).
Chen, et al., "Enhancement and destruction of antibody function by somatic mutation: unequal occurrence is controlled by V gene combinatorial associations," EMBO Journal, vol. 14, No. 12, pp. 2784-2794, (1995).
Saldanha, Molecular Engineering I: Humanization, Handbook of Therapeutic Antibodies, edited by Stefan Dubel, Copyright 2007 Wiley-VCH Verlag GmbH & Co. KGaA, Weinheim, excerpt, (2007).
EP 18864376.1 Supplemental European Search Report dated Jun. 1, 2021.
EP 18863984 Supplemental European Search Report dated Jul. 1, 2021.
Kang, et al., Rapid Formulation Development for Monoclonal Antibodies, Apr. 12, 2016, Internet Citation, retrieved at www.https://bioprocessintl.com/manufacturing/formulation/rapid-formulation-development-for-monoclonal-antibodies/ on Sep. 20, 2021.
EP 18882542.6 Supplemental European Search Report dated Jul. 27, 2021.
Wang, et al., "Antibody Structure, Instability and Formulation," Journal of Pharmaceutical Sciences, vol. 96, No. 1, (Jan. 2007).
Daugherty, et al., "Formulation and Delivery Issues for Monoclonal Antibody Therapeutics," Advanced Drug Delivery Reviews, 58(5-6):686-42 (2006) with permission Elsevier.
U.S. Appl. No. 16/789,319 Notice of Allowance and Interview Summary dated Oct. 27, 2021.
U.S. Appl. No. 16/789,319 Corrected Notice of Allowance dated Nov. 19, 2021.
Liu et al., "The Proteomics Research of Sjogren's Syndrome," Journal of Kunming Medical University, 37(4) : 65-70, (2016).
PCT/US2021/018632 International Preliminary Report on Patentability dated Aug. 23, 2022.
U.S. Appl. No. 17/127,719 Notice of Allowance and Interview Summary dated Sep. 30, 2022.
Martinez-Naharro, et al., "Magnetic Resonance in Transthyretin Cardiac Amyloidosis," Journal of the American College of Cardiology, vol. 70, No. 4, (2017).
Gertz, et al., "Diagnosis, Prognosis, and Therapy of Transthyretin Amyloidosis," Journal of the American College of Cardiology, vol. 66, No. 21, (2015).
Ando, et al., "Transthyretin: its function and pathogenicity," Japan Pharmaceutical Society Journal, vol. 98, No. 8, pp. 2006-2012, (2009), English Abstract not available.
Sekijima, Pathogenesis and Therapeutic Strategy for Protein Misfolding Disease, The Shinshu Medical Journal, vol. 56, Issue 3, (2008). English Abstract not available.
EP22195219 European Search Report dated Jan. 5, 2023.
U.S. Appl. No. 17/307,968 Non-Final Office Action and Interview Summary dated Mar. 9, 2023.
Package Insert for Herceptin, Roche, date Jun. 25, 2014.
Package Insert for Xolair, Genentech USA, Inc. and Novartis Pharmaceuticals Corporation, revision date Sep. 2014 and initial date Jun. 2003.
U.S. Appl. No. 15/201,429, filed Jul. 2, 2016; now issued as U.S. Pat. No. 10,633,433 on Apr. 28, 2020.
U.S. Appl. No. 15/201,423, filed Jul. 2, 2016; now issued as U.S. Pat. No. 10,464,999 on Nov. 5, 2019.
U.S. Appl. No. 15/201,416, filed Jul. 2, 2016; now issued as U.S. Pat. No. 9,879,080 on Jan. 30, 2018.
U.S. Appl. No. 15/861,600, filed Jan. 3, 2018; now issued as U.S. Pat. No. 10,494,426 on Dec. 3, 2019.
U.S. Appl. No. 16/129,618, filed Sep. 12, 2018, now issued as U.S. Pat. No. 10,669,330 on Jun. 2, 2020.
U.S. Appl. No. 16/584,634, filed Sep. 26, 2019; now issued as U.S. Pat. No. 11,028,158 on Jun. 8, 2021.
U.S. Appl. No. 16/669,375, filed Oct. 30, 2019; now issued as U.S. Pat. No. 10,906,967 on Feb. 2, 2021.
U.S. Appl. No. 16/789,319, filed Feb. 12, 2020; now issued as U.S. Pat. No. 11,267,878 on Mar. 8, 2022.
U.S. Appl. No. 16/753,307, filed Apr. 2, 2020; now issued as U.S. Pat. No. 11,267,877 on Mar. 8, 2022.
U.S. Appl. No. 16/753,661, filed Apr. 3, 2020.
U.S. Appl. No. 17/127,719, filed Dec. 18, 2020.
U.S. Appl. No. 17/307,968, filed May 4, 2021.
U.S. Appl. No. 62/109,004, filed Jan. 28, 2015.
U.S. Appl. No. 62/266,555, filed Dec. 11, 2015.
U.S. Appl. No. 15/009,667, filed Jan. 28, 2016.
U.S. Appl. No. 62/109,002, filed Jan. 28, 2015.
U.S. Appl. No. 62/266,556, filed Dec. 11, 2015.

(56) References Cited

OTHER PUBLICATIONS

U.S. Appl. No. 15/009,662, filed Jan. 28, 2016.
U.S. Appl. No. 62/109,001, filed Jan. 28, 2015.
U.S. Appl. No. 62/266,557, filed Dec. 11, 2015.
U.S. Appl. No. 15/009,666, filed Jan. 28, 2016.
U.S. Appl. No. 15/844,430, filed Dec. 15, 2017.
U.S. Appl. No. 62/569,438, filed Oct. 6, 2017.
U.S. Appl. No. 62/579,817, filed Oct. 31, 2017.
U.S. Appl. No. 62/647,582, filed Mar. 23, 2018.
U.S. Appl. No. 62/592,294, filed Nov. 29, 2017.
U.S. Appl. No. 62/569,436, filed Oct. 6, 2017.
U.S. Appl. No. 62/598,965, filed Dec. 14, 2017.
U.S. Appl. No. 62/979,373, filed Feb. 20, 2020.
U.S. Appl. No. 63/022,342, filed May 8, 2020.

* cited by examiner

LYOPHILIZED FORMULATION OF A MONOCLONAL ANTIBODY AGAINST TRANSTHYRETIN

CROSS-REFERENCE TO RELATED APPLICATION

This application is a national stage entry of PCT/US2018/062902 filed Nov. 28, 2018, which claims the benefit of U.S. 62/592,294 filed Nov. 29, 2018, which is incorporated by reference in its entirety for all purposes.

REFERENCE TO A SEQUENCE LISTING

This application includes an electronic sequence listing in a file named 541985SEQLST.txt, created on May 28, 2020, and containing 140,726 bytes, which is incorporated by reference.

BACKGROUND

Several diseases are thought to be caused by the abnormal folding and aggregation of disease-specific proteins. These proteins can accumulate into pathologically diagnostic accumulations, known as amyloids, which are visualized by certain histologic stains. Amyloids are thought to elicit inflammatory responses and have multiple negative consequences for the involved tissues. In addition, smaller aggregates of abnormally folded protein may exist and exert cytotoxic effects.

Transthyretin (TTR) is one of the many proteins that are known to misfold and aggregate (e.g., undergo amyloidogenesis). Transthyretin-related amyloidosis encompasses two forms of disease: familial disease arising from misfolding of a mutated or variant TTR, and a sporadic, non-genetic disease caused by misaggregation of wild-type TTR. The process of TTR amyloidogenesis can cause pathology in the nervous system and/or heart, as well as in other tissues.

SUMMARY OF THE CLAIMED INVENTION

The invention provides pharmaceutical formulations that comprise (a) a monoclonal antibody comprising a mature heavy chain variable region comprising three CDRs of SEQ ID NO:61 and a mature light chain variable region comprising three CDRs of SEQ ID NO:70, except that positions H52 and L26 by Kabat numbering can each be independently N or S, or a monoclonal antibody comprising a mature heavy chain variable region comprising three CDRs of SEQ ID NO:1 and a mature light chain variable region comprising three CDRs of SEQ ID NO:16, wherein the antibody is present at a concentration within the range from about 25 mg/mL to about 75 mg/mL; (b) a buffer present at a concentration of about 20 mM, wherein the buffer is citrate, histidine, phosphate or succinate; (c) a sugar present at a concentration within the range from about 205 mM to about 260 mM, wherein the sugar is sucrose or trehalose or, if the sugar is absent about 160 mM arginine is present; and (d) a surfactant present at a concentration within the range from about 0.01% to about 1% by weight; wherein the formulation is characterized by a pH within the range from about 5.0 to about 6.5; provided that: (i) if histidine or succinate buffer is present, the pH is about 6.0; (ii) if phosphate buffer is present, the pH is about 6.5; and (iii) if histidine and trehalose are present the surfactant is a. PS80 orb. PS20, provided that if PS20 is present, about 25 mM L-arginine is also present. Optionally, the formulation is essentially free of mannitol or sorbitol. Optionally, the formulation comprising a monoclonal antibody as described in (a) is essentially free of mannitol and sorbitol.

In some formulations, the buffer is histidine. Optionally, the sugar is present in a range from about 230 mM to about 250 mM, optionally about 230 mM to about 240 mM. Optionally, the sugar is trehalose. Optionally, the sugar is sucrose and the surfactant is PS20 or PX188. Optionally, the surfactant is PS20 at a concentration of 0.02% w/w. Optionally, the surfactant is PX188 at a concentration of 0.04% w/w. In some formulations, 160 mM arginine is present. Optionally, the sugar is present and is trehalose. Optionally, the trehalose is present at a concentration of 205 mM. Optionally, the surfactant is PS20.

In some formulations, the buffer is citrate. Optionally, the sugar is present at 230 mM. Optionally, the surfactant is 0.02% PS20. In some formulations, the buffer is phosphate. Optionally, the sugar is present and is sucrose. In some formulations, the buffer is succinate. Optionally, the sugar is present and is sucrose.

Some formulations comprise (a) 20 mM citrate, 230 mM trehalose and 0.02% w/w PS20 at pH 5; (b) 20 mM histidine, 230 mM sucrose and 0.02% w/w PS20; (c) 20 mM phosphate, 230 mM sucrose and 0.02% w/w PS20 at pH 6.5; (d) 20 mM citrate, 230 mM sucrose and 0.02% w/w PS20 at pH 6.5; (e) 20 mM histidine, 230 mM trehalose and 0.02% w/w PS80; (f) 20 mM histidine, 0.02% w/w PS20 and 160 mM L-arginine; (g) 20 mM histidine, 240 mM sucrose and 0.04% w/w PX188; (h) 20 mM succinate, 240 mM sucrose and 0.02% w/w PS20 at a pH of 6.0; or (i) 20 mM histidine, 205 mM trehalose, 0.02% w/w PS20 and 25 mM L-arginine. Optionally, the formulation consists essentially of the antibody and about: (a) 20 mM citrate, 230 mM trehalose and 0.02% w/w PS20 at pH 5; (b) 20 mM histidine, 230 mM sucrose and 0.02% w/w PS20; (c) 20 mM phosphate, 230 mM sucrose and 0.02% w/w PS20 at pH 6.5; (d) 20 mM citrate, 230 mM sucrose and 0.02% w/w PS20 at pH 6.5; (e) 20 mM histidine, 230 mM trehalose and 0.02% w/w PS80; (f) 20 mM histidine, 0.02% w/w PS20 and 160 mM L-arginine; (g) 20 mM histidine, 240 mM sucrose and 0.04% w/w PX188; (h) 20 mM succinate, 240 mM sucrose and 0.02% w/w PS20 at a pH of 6.0; or (i) 20 mM histidine, 205 mM trehalose, 0.02% w/w PS20 and 25 mM L-arginine. Optionally, the formulation consists essentially of the antibody and about: (a) 20 mM histidine, 240 mM sucrose and 0.04% w/w PX188; (b) 20 mM succinate, 240 mM sucrose and 0.02% w/w PS20 at a pH of 6.0; or (c) 20 mM histidine, 205 mM trehalose, 0.02% w/w PS20 and 25 mM L-arginine.

In some formulations, the antibody comprises a mature heavy chain variable region comprising the amino acid sequence of SEQ ID NO:65, and a mature light chain variable region comprising the amino acid sequence of SEQ ID NO:76. Optionally, the formulation consists essentially of the antibody at about 50 mg/ml, and about 20 mM histidine, about 240 mM sucrose and about 0.04% w/w PX188.

In some formulations, the antibody comprises a mature heavy chain variable region comprising the three Kabat CDRs of SEQ ID NO:61, and a mature light chain variable region comprising the three Kabat CDRs of SEQ ID NO:70 except that positions H52 and L26 by Kabat numbering can each be independently N or S.

In some formulations, the antibody comprises a mature heavy chain variable region comprising the three Kabat CDRs of SEQ ID NO:1, and a mature light chain variable region comprising the three Kabat CDRs of SEQ ID NO:16.

In some formulations, the monoclonal antibody is a humanized, chimeric or veneered antibody. Optionally, the monoclonal antibody is humanized. Optionally, the mature heavy chain variable region has an amino acid sequence comprising any one of SEQ ID NOs:64-66 and the mature light chain variable region has an amino acid sequence comprising any one of SEQ ID NOs:74-76. Optionally, the mature heavy chain variable region has an amino acid sequence comprising any one of SEQ ID NOs:5-12 and the mature light chain variable region has an amino acid sequence comprising any one of SEQ ID NOs:19-23. Optionally, the mature heavy chain has an amino acid sequence comprising SEQ ID NO:11 and the mature light chain has an amino acid sequence comprising SEQ ID NO:19. Optionally, the mature heavy chain has an amino acid sequence comprising SEQ ID NO:65 and the mature light chain has an amino acid sequence comprising SEQ ID NO:76.

In formulations comprising a humanized antibody, the mature heavy chain variable region is fused to a heavy chain constant region and the mature light chain variable region is fused to a light chain constant region. Optionally, the mature heavy chain variable region is fused to a heavy chain constant region having the sequence of SEQ ID NO:103 provided the C-terminal lysine can be absent and/or the mature light chain variable region is fused to a light chain constant region having the sequence of SEQ ID NO:104 or 105.

In some formulations, the monoclonal antibody is present at a concentration of about 50 mg/mL. In some formulations, the histidine buffer is at a concentration of about 20 mM. In some formulations, the pH is about 5.75 to 6.25. In some formulations, the sugar/polyol is sucrose present at a concentration of about 240 mM. In some formulations, the poloxamer is poloxamer 188 at a concentration of about 0.04% by weight. In some formulations, less than about 5% or 3% by weight of the antibody is present as an aggregate in the formulation. In some formulations, at least 95% or 97% of antibody by weight runs as a single peak under HP-SEC analysis. Some formulations are sterile. Some formulations are stable on freezing and thawing. Some formulations have an osmolality of from about 270 mOsmol/kg to about 330 mOsmol/kg.

The invention also provides a lyophilized formulation of an antibody that comprises (a) a monoclonal antibody comprising a mature heavy chain variable region comprising three CDRs of SEQ ID NO:61 and a mature light chain variable region comprising three CDRs of SEQ ID NO:70, except that positions H52 and L26 by Kabat numbering can each be independently N or S, or a monoclonal antibody comprising a mature heavy chain variable region comprising three CDRs of SEQ ID NO:1 and a mature light chain variable region comprising three CDRs of SEQ ID NO:16; (b) histidine; (c) a sugar/polyol; and (d) a poloxamer. Optionally, the lyophilized formulation is prepared by lyophilizing the above-mentioned formulations. Optionally, the lyophilized formulation is reconstitutable with water to a pH of between about 5.5 to about 6.5. Optionally, the lyophilized formulation is reconstitutable with water to a pH of about 6.0. Optionally, the lyophilized formulation contains about 10 mg to about 40 mg of the antibody.

The invention also provides a lyophilized formulation, which is reconstitutable with water to yield an aqueous solution comprising: (a) an antibody comprising a mature heavy chain variable region comprising three CDRs of SEQ ID NO:61 and a mature light chain variable region comprising three CDRs of SEQ ID NO:70, except that positions H52 and L26 by Kabat numbering can each be independently N or S, or a monoclonal antibody comprising a mature heavy chain variable region comprising three CDRs of SEQ ID NO:1 and a mature light chain variable region comprising three CDRs of SEQ ID NO:16 wherein the antibody is present at a concentration within the range from about 25 mg/mL to about 75 mg/mL; (b) buffer present at a concentration within a range from about 10 mM to about 30 mM; (c) sugar/polyol present at a concentration within a range from about 220 mM to about 260 mM; (d) surfactant present at a concentration within a range from about 0.01% to about 0.1% by weight; and (e) a pH within a range from about 5.5 to about 7.0.

In some lyophilized formulations, the antibody comprises a mature heavy chain variable region having an amino acid sequence comprising any one of SEQ ID NOs:64-66 and a mature light chain variable region having an amino acid sequence comprising any one of SEQ ID NOs:74-76, or an antibody comprising a mature heavy chain variable region having an amino acid sequence comprising any one of SEQ ID NOs:5-12 and a mature light chain variable region having an amino acid sequence comprising any one of SEQ ID NOs:19-23. Optionally, the lyophilized formulation is reconstitutable with water so that the antibody is present at a concentration of about 50 mg/mL. Optionally, the buffer comprises histidine. Optionally, the lyophilized formulation is reconstitutable with water so that the pH is about 6.0. Optionally, the sugar/polyol is sucrose. Optionally, the surfactant is poloxomer. Optionally, the poloxomer is PX188.

In some lyophilized formulations, (a) the antibody comprises a mature heavy chain variable region having an amino acid sequence comprising any one of SEQ ID NOs:64-66 and a mature light chain variable region having an amino acid sequence comprising any one of SEQ ID NOs:74-76 and is reconstitutable to a concentration of about 50 mg/ml; (b) the buffer is histidine and is reconstitutable to a concentration of about 20 mM; (c) the sugar/polyol is sucrose and is reconstitutable to a concentration of about 240 mM; and (d) the surfactant is poloxomer 188 and is reconstitutable to a concentration of about 0.04% by weight. Optionally, the lyophilized formulation is reconstitutable with water so that the pH is about 6.0. Optionally, the antibody comprises a mature heavy chain variable region having an amino acid sequence comprising SEQ ID NO:65 and a mature light chain variable region having an amino acid sequence comprising SEQ ID NO:76. Optionally, the mature heavy chain variable region is fused to a heavy chain constant region having the sequence of SEQ ID NO:103 and the mature light chain variable region is fused to a light chain constant region having the sequence of SEQ ID NO:104. In these lyophilized formulations, at least 95 or 97% of the antibody runs as a single peak under HP-SEC after storage for up to 3 months at 2-8° C.

The invention also provides a method of reconstituting the lyophilized formulation that comprises combining the lyophilized formulation with sterile water to produce a liquid formulation. Optionally, it further comprises introducing the reconstituted formulation into a bag of isotonic fluid for infusion. Optionally, the lyophilized formulation is in powder form or in the form of a solid foam in a vial.

The invention further provides a sterile lyophilized dosage form of an antibody formulation in a 20 ml vial consisting essentially of: (i) an antibody within a range of about 225-275 mg; (ii) histidine within a range of about 15-19 mg; (iii) poloxamer PX188 within a range of about 2-2.5 mg; and; (iv) sucrose within a range of about 400-490 mg; wherein the antibody is a monoclonal antibody comprising a mature heavy chain variable region comprising three CDRs of SEQ ID NO:61 and a mature light chain variable region comprising three CDRs of SEQ ID NO:70, except that positions H52 and L26 by Kabat numbering can each be independently N or S, or a monoclonal antibody comprising a mature heavy chain variable region comprising three CDRs of SEQ ID NO:1 and a mature light chain variable region comprising three CDRs of SEQ ID NO:16. Optionally, the vial has contents consisting essentially of: (i) about 250 mg of the antibody; (ii) about 16.8 mg of L-histidine; (iii) about 2.2 mg of poloxomer PX188; and (iv) about 445.3 mg of sucrose. Optionally, the antibody comprises a mature heavy chain variable region comprising the three Kabat CDRs of SEQ ID NO:61, and a mature light chain variable region comprising the three Kabat CDRs of SEQ ID NO:70 except that positions H52 and L26 by Kabat numbering can each be independently N or S. Optionally, the antibody comprises a mature heavy chain variable region comprising the three Kabat CDRs of SEQ ID NO:1, and a mature light chain variable region comprising the three Kabat CDRs of SEQ ID NO:16. Optionally, the mature heavy chain variable region has an amino acid sequence comprising any one of SEQ ID NOs:64-66 and the mature light chain variable region has an amino acid sequence comprising any one of SEQ ID NOs:74-76. Optionally, the mature heavy chain variable region has an amino acid sequence comprising any one of SEQ ID NOs:5-12 and the mature light chain variable region has an amino acid sequence comprising any one of SEQ ID NOs:19-23. Optionally, the mature heavy chain has an amino acid sequence comprising SEQ ID NO:65 and the mature light chain has an amino acid sequence comprising SEQ ID NO:76. Optionally, the mature heavy chain has an amino acid sequence comprising SEQ ID NO:6 and the mature light chain has an amino acid sequence comprising SEQ ID NO:21. Optionally, the mature heavy chain variable region is fused to a heavy chain constant region having the sequence of SEQ ID NO:103 provided the C-terminal lysine can be absent and/or the mature light chain variable region is fused to a light chain constant region having the sequence of SEQ ID NO:104 or 105. Optionally, the mature heavy chain has the sequence of SEQ ID NO:82, except the C-terminal lysine may be absent, and the mature light chain has the sequence of SEQ ID NO:86.

The invention also provides a method of preparing the lyophilized dosage form of for administration to a subject, comprising: (i) reconstituting the antibody formulation to a volume of about 5.0 mL with sterile water, and (ii) diluting the reconstituted antibody formulation of step (i) in normal saline for infusion. Optionally, the total volume for infusion is 250 mL. Optionally, the total volume for infusion is 100 mL. Optionally, the total volume for infusion is 500 mL.

The invention also provides a reconstituted formulation resulting from reconstituting lyophilized formulations. Some reconstituted formulations comprise the antibody at a concentration of about 50 mg/mL, the histidine buffer at a concentration of about 20 mM, poloxamer at a concentration of about 0.04% by weight, and at pH of about 6.0. Optionally, at least 95, 96, 97, 98 or 99% of the antibody runs as a single peak on high pressure size exclusion chromatography.

The invention also provides a method of treating or effecting prophylaxis of a subject having or at risk of a transthyretin-mediated amyloidosis, comprising administering to the subject an effective regime of the pharmaceutical formulation or a reconstituted form of the lyophilized formulation. Optionally, the subject has been previously treated with a TTR tetramer stabilizer, an antisense oligonucleotide based therapy, an RNA interference (RNAi) based therapy, or an amyloid degrader. Optionally, the subject no longer receives the treatment with the TTR tetramer stabilizer, antisense oligonucleotide based therapy, RNA interference (RNAi) based therapy, or amyloid degrader. Optionally, the subject is concurrently receiving treatment with diflunisal. Optionally, the subject is concurrently receiving treatment with tafamidis. Optionally, the subject is concurrently receiving treatment with a TTR tetramer stabilizer, an antisense oligonucleotide based therapy, an RNA interference (RNAi) based therapy, or an amyloid degrader. Optionally, the subject is concurrently receiving treatment with tafamidis, diflunisal, patisiran, inotersen, 4'-iodo-4'-deoxydoxorubicin (IDOX), doxycycline, tauroursodeoxycholic acid (TUDCA), cyclodextrin (CyD), or an anti-SAP antibody. Optionally, the subject has been diagnosed with ATTR amyloidosis. Optionally, the subject has wild-type ATTR-cardiomyopathy. Optionally, the subject has hereditary ATTR-cardiomyopathy, or hereditary ATTR-polyneuropathy or both. Optionally, the subject has ATTR cardiac involvement. Optionally, the subject has ATTR amyloidosis peripheral neuropathy involvement. Optionally, the subject is receiving concomitant tafamidis.

The invention also provides that a pharmaceutical formulation, the reconstituted form of the lyophilized formulation or the reconstituted form of the lyophilized antibody formulation is administered to the subject intravenously in diluted form. Optionally, the diluent for the diluted form is normal saline. Optionally, the total volume of the diluted form administered to the subject is at least about 100 mL. Optionally, the total volume of the diluted form administered to the subject is at least about 250 mL. Optionally, the total volume of the diluted form administered to the subject is at least about 500 mL. Optionally, the total volume is about 250 mL. Optionally, 0.1, 0.2, 0.3, 1, 3, 10 or 30 mg/kg of the antibody is administered to the subject about once every 28 days. Optionally, 0.1, 0.2, 0.3, 1 or 3 mg/kg of the antibody is administered to the subject as an infusion over a range of about 60 to 120 minutes. Optionally, 10 or 30 mg/kg of the antibody is administered to the subject as an infusion over a range of about 90 to 180 minutes. Optionally, the subject is premedicated with an antihistamine. Optionally, the subject is adminstered diphenhydramine within a range of about 30 to 90 minutes prior to the antibody administration. Optionally, the subject is administered acetaminophen within a range of about 30 to 90 minutes prior to the antibody administration. Optionally, the duration of the regime is at least 3 months. Optionally, the duration of the regime is at least 12 months.

The invention further provides a method of treating or effecting prophylaxis of a subject having or at risk of a transthyretin-mediated amyloidosis that comprises administering an effective regime of a TTR tetramer stabilizer, an antisense oligonucleotide based therapy, an RNA interference (RNAi) based therapy, or an amyloid degrader, wherein the subject has previously been treated with the pharmaceutical formulation or a reconstituted form of the lyophilized formulation as described above. Optionally, the subject no longer receives the treatment with the pharmaceutical formulation. Optionally, the TTR tetramer stabilizer is tafamidis or diflunisal. Optionally, the antisense oligonucleotide based therapy is inotersen. Optionally, the RNA interference (RNAi) based therapy is patisiran or revusiran. Optionally, the amyloid degraders are 4'-iodo-4'-deoxydoxorubicin (IDOX), doxycycline, tauroursodeoxycholic acid (TUDCA), cyclodextrin (CyD), or an anti-SAP antibody.

Optionally, the amyloid degraders are doxycycline in combined with tauroursodeoxycholic acid (TUDCA). Optionally, the subject has been diagnosed with ATTR amyloidosis. Optionally, the subject has wild-type ATTR-cardiomyopathy. Optionally, the subject has hereditary ATTR-cardiomyopathy. Optionally, the subject has hereditary ATTR-polyneuropathy. Optionally, the subject has ATTR cardiac involvement. Optionally, the subject has ATTR amyloidosis peripheral neuropathy involvement. Optionally, the pharmaceutical formulation, reconstituted form of the lyophilized formulation or the reconstituted form of the lyophilized antibody formulation is administered to the subject intravenously in diluted form. Optionally, the diluent for the diluted form is normal saline. Optionally, the total volume of the diluted form administered to the subject is at least about 100 mL. Optionally, the total volume of the diluted form administered to the subject is at least about 250 mL. Optionally, the total volume of the diluted form administered to the subject is at least about 500 mL. Optionally, the total volume is about 250 mL. Optionally, 0.1, 0.2, 0.3, 1, 3, 10 or 30 mg/kg of the antibody is administered to the subject about once every 28 days. Optionally, 0.1, 0.2, 0.3, 1 or 3 mg/kg of the antibody is administered to the subject as an infusion over a range of about 60 to 120 minutes. Optionally, 10 or 30 mg/kg of the antibody is administered to the subject as an infusion over a range of about 90 to 180 minutes. Optionally, the subject is premedicated with an antihistamine. Optionally, the subject is adminstered diphenhydramine within a range of about 30 to 90 minutes prior to the antibody administration. Optionally, the subject is administered acetaminophen within a range of about 30 to 90 minutes prior to the antibody administration. Optionally, the duration of the regime is at least 3 months. Optionally, the duration of the regime is at least 12 months.

BRIEF DESCRIPTION OF THE SEQUENCES

SEQ ID NO:1 sets forth the amino acid sequence of the heavy chain variable region of the mouse 9D5 antibody.

SEQ ID NO:2 sets forth the amino acid sequence of the mouse heavy chain variable region structure template 1SEQ_H.

SEQ ID NO:3 sets forth the amino acid sequence of the heavy chain variable acceptor ACC #BACO2114.

SEQ ID NO:4 sets forth the amino acid sequence of the heavy chain variable acceptor ACC #AAX82494.1.

SEQ ID NO:5 sets forth the amino acid sequence of the heavy chain variable region of the humanized 9D5 antibody version 1 (Hu9D5VHv1).

SEQ ID NO:6 sets forth the amino acid sequence of the heavy chain variable region of the humanized 9D5 antibody version 2 (Hu9D5VHv2).

SEQ ID NO:7 sets forth the amino acid sequence of the heavy chain variable region of the humanized 9D5 antibody version 2b (Hu9D5VHv2b).

SEQ ID NO:8 sets forth the amino acid sequence of the heavy chain variable region of the humanized 9D5 antibody version 3 (Hu9D5VHv3).

SEQ ID NO:9 sets forth the amino acid sequence of the heavy chain variable region of the humanized 9D5 antibody version 3b (Hu9D5VHv3b).

SEQ ID NO:10 sets forth the amino acid sequence of the heavy chain variable region of the humanized 9D5 antibody version 4 (Hu9D5VHv4).

SEQ ID NO:11 sets forth the amino acid sequence of the heavy chain variable region of the humanized 9D5 antibody version 4b (Hu9D5VHv4b).

SEQ ID NO:12 sets forth the amino acid sequence of the heavy chain variable region of the humanized 9D5 antibody version 5 (Hu9D5VHv5).

SEQ ID NO:13 sets forth the amino acid sequence of Kabat CDR-H1 of the mouse 9D5 antibody.

SEQ ID NO:14 sets forth the amino acid sequence of Kabat CDR-H2 of the mouse 9D5 antibody.

SEQ ID NO:15 sets forth the amino acid sequence of Kabat CDR-H3 of the mouse 9D5 antibody.

SEQ ID NO:16 sets forth the amino acid sequence of the light chain variable region of the mouse 9D5 antibody.

SEQ ID NO:17 sets forth the amino acid sequence of the mouse light chain variable region structure template 1MJU_L.

SEQ ID NO:18 sets forth the amino acid sequence of the light chain variable acceptor ACC #ABC66952.

SEQ ID NO:19 sets forth the amino acid sequence of the light chain variable region of the humanized 9D5 antibody version 1 (Hu9D5VLv1).

SEQ ID NO:20 sets forth the amino acid sequence of the light chain variable region of the humanized 9D5 antibody version 2 (Hu9D5VLv2).

SEQ ID NO:21 sets forth the amino acid sequence of the light chain variable region of the humanized 9D5 antibody version 3 (Hu9D5VLv3).

SEQ ID NO:22 sets forth the amino acid sequence of the light chain variable region of the humanized 9D5 antibody version 4 (Hu9D5VLv4).

SEQ ID NO:23 sets forth the amino acid sequence of the light chain variable region of the humanized 9D5 antibody version 5 (Hu9D5VLv5).

SEQ ID NO:24 sets forth the amino acid sequence of Kabat CDR-L1 of the mouse 9D5 antibody.

SEQ ID NO:25 sets forth the amino acid sequence of Kabat CDR-L2 of the mouse 9D5 antibody.

SEQ ID NO:26 sets forth the amino acid sequence of Kabat CDR-L3 of the mouse 9D5 antibody.

SEQ ID NO:27 sets forth the amino acid sequence of humanized 9D5 heavy chain version 1.

SEQ ID NO:28 sets forth the amino acid sequence of humanized 9D5 heavy chain version 2.

SEQ ID NO:29 sets forth the amino acid sequence of humanized 9D5 heavy chain version 2b.

SEQ ID NO:30 sets forth the amino acid sequence of humanized 9D5 heavy chain version 3.

SEQ ID NO:31 sets forth the amino acid sequence of humanized 9D5 heavy chain version 3b.

SEQ ID NO:32 sets forth the amino acid sequence of humanized 9D5 heavy chain version 4.

SEQ ID NO:33 sets forth the amino acid sequence of humanized 9D5 heavy chain version 4b.

SEQ ID NO:34 sets forth the amino acid sequence humanized 9D5 heavy chain version 5.

SEQ ID NO:35 sets forth the amino acid sequence of humanized 9D5 light chain version 1.

SEQ ID NO:36 sets forth the amino acid sequence of humanized 9D5 light chain version 2.

SEQ ID NO:37 sets forth the amino acid sequence of humanized 9D5 light chain version 3.

SEQ ID NO:38 sets forth the amino acid sequence of humanized 9D5 light chain version 4.

SEQ ID NO:39 sets forth the amino acid sequence of humanized 9D5 light chain version 5.

SEQ ID NO:40 sets forth the nucleic acid sequence of the heavy chain variable region of the mouse 9D5 antibody with signal peptide.

SEQ ID NO:41 sets forth the amino acid sequence of the heavy chain variable region of the mouse 9D5 antibody with signal peptide.

SEQ ID NO:42 sets forth the nucleic acid sequence of the light chain variable region of the mouse 9D5 antibody with signal peptide.

SEQ ID NO:43 sets forth the amino acid sequence of the light chain variable region of the mouse 9D5 antibody with signal peptide.

SEQ ID NO:44 sets forth the nucleic acid sequence of the heavy chain variable region of the humanized 9D5 antibody version 1 (Hu9D5VHv1).

SEQ ID NO:45 sets forth the nucleic acid sequence of the heavy chain variable region of the humanized 9D5 antibody version 2 (Hu9D5VHv2).

SEQ ID NO:46 sets forth the nucleic acid sequence of the heavy chain variable region of the humanized 9D5 antibody version 2b (Hu9D5VHv2b).

SEQ ID NO:47 sets forth the nucleic acid sequence of the heavy chain variable region of the humanized 9D5 antibody version 3 (Hu9D5VHv3).

SEQ ID NO:48 sets forth the nucleic acid sequence of the heavy chain variable region of the humanized 9D5 antibody version 3b (Hu9D5VHv3b).

SEQ ID NO:49 sets forth the nucleic acid sequence of the heavy chain variable region of the humanized 9D5 antibody version 4 (Hu9D5VHv4).

SEQ ID NO:50 sets forth the nucleic acid sequence of the heavy chain variable region of the humanized 9D5 antibody version 4b (Hu9D5VHv4b).

SEQ ID NO:51 sets forth the nucleic acid sequence of the heavy chain variable region of the humanized 9D5 antibody version 5 (Hu9D5VHv5).

SEQ ID NO:52 sets forth the nucleic acid sequence of the light chain variable region of the humanized 9D5 antibody version 1 (Hu9D5VLv1).

SEQ ID NO:53 sets forth the nucleic acid sequence of the light chain variable region of the humanized 9D5 antibody version 2 (Hu9D5VLv2).

SEQ ID NO:54 sets forth the nucleic acid sequence of the light chain variable region of the humanized 9D5 antibody version 3 (Hu9D5VLv3).

SEQ ID NO:55 sets forth the nucleic acid sequence of the light chain variable region of the humanized 9D5 antibody version 4 (Hu9D5VLv4).

SEQ ID NO:56 sets forth the nucleic acid sequence of the light chain variable region of the humanized 9D5 antibody version 5 (Hu9D5VLv5).

SEQ ID NO:57 sets forth the amino acid sequence of the mouse 9D5 heavy chain variable region signal peptide.

SEQ ID NO:58 sets forth the nucleic acid sequence of the mouse 9D5 heavy chain variable region signal peptide.

SEQ ID NO:59 sets forth the amino acid sequence of the mouse 9D5 light chain variable region signal peptide.

SEQ ID NO:60 sets forth the nucleic acid sequence of the mouse 9D5 light chain variable region signal peptide.

SEQ ID NO:61 sets forth the amino acid sequence of the heavy chain variable region of the mouse 14G8 antibody.

SEQ ID NO:62 sets forth the amino acid sequence of the mouse heavy chain variable region structure template 1MQK_H.

SEQ ID NO:63 sets forth the amino acid sequence of the heavy chain variable acceptor ACC #AAD30410.1.

SEQ ID NO:64 sets forth the amino acid sequence of the heavy chain variable region of the humanized 14G8 antibody version 1 (Hu14G8VHv1).

SEQ ID NO:65 sets forth the amino acid sequence of the heavy chain variable region of the humanized 14G8 antibody version 2 (Hu14G8VHv2).

SEQ ID NO:66 sets forth the amino acid sequence of the heavy chain variable region of the humanized 14G8 antibody version 3 (Hu14G8VHv3).

SEQ ID NO:67 sets forth the amino acid sequence of Kabat CDR-H1 of the mouse 14G8 antibody.

SEQ ID NO:68 sets forth the amino acid sequence of Kabat CDR-H2 of the mouse 14G8 antibody.

SEQ ID NO:69 sets forth the amino acid sequence of Kabat CDR-H3 of the mouse 14G8 antibody.

SEQ ID NO:70 sets forth the amino acid sequence of the light chain variable region of the mouse 14G8 antibody.

SEQ ID NO:71 sets forth the amino acid sequence of the mouse light chain variable region structure template 1MJU_L.

SEQ ID NO:72 sets forth the amino acid sequence of the light chain variable acceptor ACC #ABA71374.1.

SEQ ID NO:73 sets forth the amino acid sequence of the light chain variable acceptor ACC #ABC66952.1.

SEQ ID NO:74 sets forth the amino acid sequence of the light chain variable region of the humanized 14G8 antibody version 1 (Hu14G8VLv1).

SEQ ID NO:75 sets forth the amino acid sequence of the light chain variable region of the humanized 14G8 antibody version 2 (Hu14G8VLv2).

SEQ ID NO:76 sets forth the amino acid sequence of the light chain variable region of the humanized 14G8 antibody version 3 (Hu14G8VLv3).

SEQ ID NO:77 sets forth the amino acid sequence of Kabat CDR-L1 of the mouse 14G8 antibody.

SEQ ID NO:78 sets forth the amino acid sequence of Kabat CDR-L2 of the mouse 14G8 antibody.

SEQ ID NO:79 sets forth the amino acid sequence of Kabat CDR-L3 of the mouse 14G8 antibody.

SEQ ID NO:80 sets forth the amino acid sequence of Kabat CDR-L1 of the humanized 14G8 antibody version 3 (Hu14G8VLv3).

SEQ ID NO:81 sets forth the amino acid sequence of humanized 14G8 heavy chain version 1.

SEQ ID NO:82 sets forth the amino acid sequence of humanized 14G8 heavy chain version 2.

SEQ ID NO:83 sets forth the amino acid sequence of humanized 14G8 heavy chain version 3.

SEQ ID NO: 84 sets forth the amino acid sequence of humanized 14G8 light chain version 1.

SEQ ID NO:85 sets forth the amino acid sequence of humanized 14G8 light chain version 2.

SEQ ID NO:86 sets forth the amino acid sequence of humanized 14G8 light chain version 3.

SEQ ID NO:87 sets forth the nucleic acid sequence of the heavy chain variable region of the mouse 14G8 antibody with signal peptide.

SEQ ID NO:88 sets forth the amino acid sequence of the heavy chain variable region of the mouse 14G8 antibody with signal peptide.

SEQ ID NO:89 sets forth the nucleic acid sequence of the light chain variable region of the mouse 14G8 antibody with signal peptide.

SEQ ID NO:90 sets forth the amino acid sequence of the light chain variable region of the mouse 14G8 antibody with signal peptide.

SEQ ID NO:91 sets forth the nucleic acid sequence of the heavy chain variable region of the humanized 14G8 antibody version 1 (Hu14G8VHv1).

SEQ ID NO:92 sets forth the nucleic acid sequence of the heavy chain variable region of the humanized 14G8 antibody version 2 (Hu14G8VHv2).

SEQ ID NO:93 sets forth the nucleic acid sequence of the heavy chain variable region of the humanized 14G8 antibody version 3 (Hu14G8VHv3).

SEQ ID NO:94 sets forth the nucleic acid sequence of the light chain variable region of the humanized 14G8 antibody version 1 (Hu14G8VLv1).

SEQ ID NO:95 sets forth the nucleic acid sequence of the light chain variable region of the humanized 14G8 antibody version 2 (Hu14G8VLv2).

SEQ ID NO:96 sets forth the nucleic acid sequence of the light chain variable region of the humanized 14G8 antibody version 3 (Hu14G8VLv3).

SEQ ID NO:97 sets forth the amino acid sequence of the mouse 14G8 heavy chain variable region signal peptide.

SEQ ID NO:98 sets forth the nucleic acid sequence of the mouse 14G8 heavy chain variable region signal peptide.

SEQ ID NO:99 sets forth the amino acid sequence of the mouse 14G8 light chain variable region signal peptide.

SEQ ID NO:100 sets forth the nucleic acid sequence of the mouse 14G8 light chain variable region signal peptide.

SEQ ID NO:101 sets forth the amino acid sequence of an exemplary human IgG1 heavy chain constant region.

SEQ ID NO:102 sets forth the amino acid sequence of an exemplary human IgG1 heavy chain constant region of the IgG1 G1m3 allotype with alanines occupying positions 234 and 235 by EU numbering.

SEQ ID NO:103 sets forth the amino acid sequence of an exemplary human IgG1 heavy chain constant region of the IgG1 G1m3 allotype.

SEQ ID NO:104 sets forth the amino acid sequence of an exemplary human kappa light chain constant region having an N-terminal arginine.

SEQ ID NO:105 sets forth the amino acid sequence of an exemplary human kappa light chain constant region without an N-terminal arginine.

SEQ ID NO:106 sets forth the nucleic acid sequence of an exemplary heavy chain constant region of the G1m3 allotype.

SEQ ID NO:107 sets forth the nucleic acid sequence of an exemplary light chain constant region having an N-terminal arginine.

SEQ ID NO:108 sets forth the nucleic acid sequence of an exemplary light chain constant region without an N-terminal arginine.

SEQ ID NO:109 sets forth the amino acid sequence of human transthyretin set forth in accession number P02766.1 (UniProt).

SEQ ID NO:110 sets forth the amino acid sequence of human transthyretin set forth in accession number AAB35639.1 (GenBank).

SEQ ID NO:111 sets forth the amino acid sequence of human transthyretin set forth in accession number AAB35640.1 (GenBank).

SEQ ID NO:112 sets forth the amino acid sequence of human transthyretin set forth in accession number ABI63351.1 (GenBank).

SEQ ID NO:113 sets forth the amino acid sequence of residues 89-97 of human transthyretin.

SEQ ID NO:114 sets forth the amino acid sequence of a potential transthyretin immunogen.

SEQ ID NO:115 sets forth the amino acid sequence of a potential transthyretin immunogen.

SEQ ID NO:116 sets forth the amino acid sequence of a potential transthyretin immunogen.

SEQ ID NO:117 sets forth the amino acid sequence of composite Chothia-Kabat CDR-H1 of the mouse 9D5 antibody.

SEQ ID NO:118 sets forth the amino acid sequence of composite Chothia-Kabat CDR-H1 of the mouse 14G8 antibody.

Definitions

The term "antibody" includes intact antibodies and binding fragments thereof. Typically, fragments compete with the intact antibody from which they were derived for specific binding to the target. Fragments include separate heavy chains, separate light chains, Fab, Fab', F(ab')2, F(ab)c, Fv, single chain antibodies, and single domain antibodies The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The basic antibody structural unit is a tetramer of subunits. Each tetramer includes two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. When initially expressed, this variable region is typically linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function. A constant region can include any or all of a CH1 region, hinge region, CH2 region, and CH3 region.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except for bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the regions FR1, CDR1, FR2, CDR2, FR3, CDR3 and FR4. The assignment of amino acids to each region is in accordance with the definitions of Kabat, *Sequences of Proteins of Immunological Interest* (National Institutes of Health, Bethesda, MD, 1987 and 1991), or Chothia & Lesk, *J. Mol. Biol.* 196:901-917 (1987); Chothia et al., *Nature* 342:878-883 (1989) or CDRs can be defined by the alternative definitions in Table 1 below. Kabat also provides a widely used numbering convention (Kabat numbering) in which corresponding residues between different heavy chains or between different light chains are assigned the same number.

TABLE 1

Table 1: Conventional Definitions of CDRs Using Kabat Numbering

| Loop | Kabat | Chothia | Composite of Chothia & Kabat | AbM | Contact |
|---|---|---|---|---|---|
| L1 | L24-L34 | L24-L34 | L24-L34 | L24-L34 | L30-L36 |
| L2 | L50-L56 | L50-L56 | L50-L56 | L50-L56 | L46-L55 |
| L3 | L89-L97 | L89-L97 | L89-L97 | L89-L97 | L89-L96 |
| H1 | H31-H35B | H26-H32 ... H34* | H26-H35B* | H26-H35B | H30-H35B |
| H2 | H50-H65 | H52-H56 | H50-H65 | H50-H58 | H47-H58 |
| H3 | H95-H102 | H95-H102 | H95-H102 | H95-H102 | H93-H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

The mature variable region of a heavy or light chain is being compared with the same region of a reference antibody, the percentage sequence identity between the subject and reference antibody regions is the number of positions occupied by the same amino acid in both the subject and reference antibody region divided by the total number of aligned positions of the two regions (with gaps not counted) multiplied by 100 to convert to percentage.

For purposes of classifying amino acids substitutions as conservative or non-conservative, amino acids are grouped as follows: Group I (hydrophobic sidechains): Norleucine, Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions involve substitutions between amino acids in the same class.

Non-conservative substitutions constitute exchanging a member of one of these classes for a member of another.

Antibodies of the invention typically bind to their designated target with an affinity constant of at least $10^6$, $10^7$, $10^8$, $10^9$, or $10^{10}$ M$^{-1}$. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a monoclonal antibody binds one and only one target.

The term "symptom" refers to subjective evidence of a disease, such as altered gait, as perceived by a subject. A "sign" refers to objective evidence of a disease as observed by a physician.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor. Statistical significance means $p \leq 0.05$.

Unless otherwise apparent from the context, the term "about" encompasses values within ±5 or ±10% of a stated value.

Unless otherwise apparent from the context, reference to a range includes any integer within the range.

The term "native" with respect to the structure transthyretin (TTR) refers to the normal folded structure of TTR in its properly functioning state (i.e., a TTR tetramer). As TTR is a tetramer in its natively folded form, non-native forms of TTR include, for example, misfolded TTR tetramers, TTR monomers, aggregated forms of TTR, and fibril forms of TTR. Non-native forms of TTR can include molecules comprising wild-type TTR amino acid sequences or mutations.

The term "misfolded" with respect to TTR refers to the secondary and tertiary structure of a TTR polypeptide monomer or multimer, and indicates that the polypeptide has adopted a conformation that is not normal for that protein in its properly functioning state. Although TTR misfolding can be caused by mutations in the protein (e.g., deletion, substitution, or addition), wild-type TTR proteins can also be misfolded in diseases, exposing specific epitopes.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

DETAILED DESCRIPTION

I. General

14G8 and 9D5 are antibodies binding to transthyretin (TTR). Humanized forms of the antibodies are described in WO2016/120810, incorporated by reference in its entirety for all purposes. The present application provides liquid and lyophilized formulations incorporating antibodies having the CDRs of the 14G8 or 9D5 antibody, particularly chimeric, veneered or humanized forms of 14G8 or 9D5. The formulations include combinations of pharmaceutically acceptable carriers conferring stability on the antibody as further described below.

II. Target Molecules

Transthyretin (TTR) is a 127-amino acid, 55 kDa serum and cerebrospinal fluid transport protein primarily synthesized by the liver. It has also been referred to as prealbumin, thyroxine binding prealbumin, ATTR, and TBPA. In its native state, TTR exists as a tetramer. In homozygotes, the tetramers comprise identical 127-amino-acid beta-sheet-rich subunits. In heterozygotes, the TTR tetramers are made up of variant and/or wild-type subunits, typically combined in a statistical fashion.

The established function of TTR in the blood is to transport holo-retinol binding protein. Although TTR is the major carrier of thyroxine (T4) in the blood of rodents, utilizing binding sites that are orthogonal to those used for holo-retinol binding protein, the T4 binding sites are effectively unoccupied in humans.

TTR is one of at least thirty different human proteins whose extracellular misfolding and/or misassembly (amyloidogenesis) into a spectrum of aggregate structures is thought to cause degenerative diseases referred to as amyloid diseases. TTR undergoes conformational changes in order to become amyloidogenic. Partial unfolding exposes stretches of largely uncharged hydrophobic residues in an extended conformation that efficiently misassemble into largely unstructured spherical aggregates that ultimately undergo conformation conversion into cross-beta sheet amyloid structures.

Unless otherwise apparent from context, reference to transthyretin (TTR) or its fragments or domains includes the natural human amino acid sequences including isoforms, mutants, and allelic variants thereof. Exemplary TTR polypeptide sequences are designated by Accession Numbers P02766.1 (UniProt), AAB35639.1 (GenBank), AAB35640.1 (GenBank), and ABI63351.1 (GenBank) (SEQ ID NOS: 109-112, respectively). Residues are numbered according to Swiss Prot P02766.1, with the first amino acid of the mature protein (i.e., not including the 20 amino acid signal sequence) designated residue 1. In any other TTR protein, residues are numbered according to the corresponding residues in P02766.1 on maximum alignment.

III. Transthyretin Amyloidosis

Transthyretin (TTR) amyloidosis is a systemic disorder characterized by pathogenic, misfolded TTR and the extracellular deposition of amyloid fibrils composed of TTR. TTR amyloidosis is generally caused by destabilization of the native TTR tetramer form (due to environmental or genetic conditions), leading to dissociation, misfolding, and aggregation of TTR into amyloid fibrils that accumulate in various organs and tissues, causing progressive dysfunction. See, e.g., Almeida and Saraiva, *FEBS Letters* 586:2891-2896 (2012); Ando et al., *Orphanet Journal of Rare Diseases* 8:31 (2013).

In humans, both wild-type TTR tetramers and mixed tetramers comprised of mutant and wild-type subunits can dissociate, misfold, and aggregate, with the process of amyloidogenesis leading to the degeneration of post-mitotic tissue. Thus, TTR amyloidoses encompass diseases caused by pathogenic misfolded TTR resulting from mutations in TTR or resulting from non-mutated, misfolded TTR.

For example, senile systemic amyloidosis (SSA) and senile cardiac amyloidosis (SCA) are age-related types of amyloidosis that result from the deposition of wild-type TTR amyloid outside and within the cardiomyocytes of the heart. TTR amyloidosis is also the most common form of hereditary (familial) amyloidosis, which is caused by mutations that destabilize the TTR protein. The TTR amyloidoses associated with point mutations in the TTR gene include familial amyloid polyneuropathy (FAP), familial amyloid cardiomyopathy (FAC), and the rare central nervous system selective amyloidosis (CNSA). Patients with hereditary (familial) TTR amyloidosis are almost always heterozygotes, meaning that the TTR tetramers are composed of mutant and/or wild-type TTR subunits, generally statistically distributed. Hereditary (familial) versions of TTR amyloidosis are generally autosomal dominant and are typically earlier onset than the sporadic diseases (SSA and SCA).

There are over 100 mutations in the gene encoding TTR that have been implicated in the autosomal dominant disorders FAP and FAC. See, e.g., US 2014/0056904; Saraiva, *Hum. Mutat.* 17(6):493-503 (2001); Damas and Saraiva, *J. Struct. Biol.* 130:290-299; Dwulet and Benson, *Biochem. Biophys. Res. Commun.* 114:657-662 (1983). These amyloid-causing mutations are distributed throughout the entire molecule of TTR. Generally, the more destabilizing the mutant subunits are to the TTR tetramer structure, the earlier the onset of amyloid disease. The pathogenic potential of a TTR variant is generally determined by a combination of its instability and its cellular secretion efficiency. The initial pathology caused by some TTR variants comes from their selective destruction of cardiac tissue, whereas that from other TTR variants comes from compromising the peripheral and autonomic nervous system. The tissue damage caused by TTR amyloidogenesis appear to stem largely from the toxicity of small, diffusible TTR aggregates, although accumulation of extracellular amyloid may contribute and almost certainly compromises organ structure in the late stages of the TTR amyloidosis.

TTR amyloidosis presents in many different forms, with considerable phenotypic variation across individuals and geographic locations. For example, TTR amyloidosis can present as a progressive, axonal sensory autonomic and motor neuropathy. TTR amyloidosis can also present as an infiltrative cardiomyopathy.

The age at onset of disease-related symptoms varies between the second and ninth decades of life, with great variations across different populations. The multisystem involvement of TTR amyloidosis is a clue to its diagnosis. For example, TTR amyloidosis diagnosis is considered when one or several of the following are present: (1) family history of neuropathic disease, especially associated with heart failure; (2) neuropathic pain or progressive sensory disturbances of unknown etiology; (3) carpal tunnel syndrome without obvious cause, particularly if it is bilateral and requires surgical release; (4) gastrointestinal motility disturbances or autonomic nerve dysfunction of unknown etiology (e.g., erectile dysfunction, orthostatic hypotension, neurogenic gladder); (5) cardiac disease characterized by thickened ventricular walls in the absence of hypertension; (6) advanced atrio-ventricular block of unknown origin, particularly when accompanied by a thickened heart; and (6) vitreous body inclusions of the cotton-wool type. See Ando et al., Orphanet Journal of Rare Diseases 8:31 (2013). Other symptoms can include, for example, polyneuropathy, sensory loss, pain, weakness in lower limbs, dyshidrosis, diarrhea, constipation, weight loss, and urinary incontinence/retention.

Peripheral neuropathy can be detected and quantified by various clinical scales. For example, Clinical Neuropathy Assessment (CAN), (Dyck P J, Hughes R A C, O'Brien P C. Quantitating overall neuropathic symptoms, impairments and outcomes. In: Dyck P J, Thomas P K, editors. Peripheral neuropathy. 4$^{th}$ ed. Philadelphia, PA: Elsevier Saunders; 2005. P 1031-51), provides a scale comprising a Lower Limb Function score (LLF), and ability (scored 0) or inability (scored 1) to walk on the toes, walk on the heels, and arise from a kneeling position; items are scored separately for each side The Neuropathy Impairment Score (NIS) provides a clinical assessment that tests muscle strength, reflex activity, and sensation of toes and fingers. For subjects with hATTR with peripheral neuropathy, neurologic function can be assessed over time using NIS. NIS involves a neurologic exam of lower limbs, upper limbs, and cranial nerves with total score of 244 (weakness 192, sensation 32, reflexes 20). The Neuropathy Symptoms and Change (NSC) is a 38-item questionnaire that assesses the severity and change of symptoms (weakness, sensory, autonomic) of peripheral neuropathy with 3 scales: number of symptoms, severity of symptoms (mild=1, moderate=2, severe=3) which can be used to assess change over time, and a change category (comparing a symptom to baseline). Other scales are the Familial Amyloidotic Polyneuropathy (FAP) stage and the Polyneuropathy Disability (PND) score.

Diagnosis of TTR amyloidosis typically relies on target organ biopsies, followed by histological staining of the excised tissue with the amyloid-specific dye, Congo red. If a positive test for amyloid is observed, immunohistochemical staining for TTR is subsequently performed to ensure that the precursor protein responsible for amyloid formation is indeed TTR. For familial forms of the diseases, demonstration of a mutation in the gene encoding TTR is then needed before diagnosis can be made. This can be accomplished, for example, through isoelectric focusing electrophoresis, polymerase chain reaction, or laser dissection/liquid chromatography-tandem mass spectrometry. See, e.g., US 2014/0056904; Ruberg and Berk, Circulation 126:1286-1300 (2012); Ando et al., Orphanet Journal of Rare Diseases 8:31 (2013).

IV. Antibodies

A. Binding Specificity and Functional Properties

The antibody 14G8 was originally isolated as a mouse antibody having a mature heavy chain variable region defined by SEQ ID NO:61 and a mature light chain variable defined by SEQ ID NO: 70. Kabat CDRH1, H2 and H3 have SEQ ID NOs:67-69 and CDRL1, L2 and L3 have SEQ ID NOs:77-79. A composite Chothia-Kabat CDR-H1 is provided as SEQ ID NO:118.

The antibody 9D5 was also originally isolated as a mouse antibody having a mature heavy chain variable region defined by SEQ ID NO:61 and a mature light chain variable defined by SEQ ID NO:70. Kabat CDRH1, H2 and H3 have SEQ ID NOs:13-15 and Kabat CDRL1, L2 and L3 have SEQ ID NOs:24-26. The Kabat CDRs of 9D5 are the same as those of 14G8 except that in 9D5 positions H52 and L26 by Kabat numbering are occupied by N and in 9D5 by S. A composite Chothia-Kabat CDR-H1 is provided as SEQ ID NO:117.

CDRs can alternatively be defined by any of the following conventions described above.

The formulations of the invention include an antibody comprising a mature heavy chain comprising CDRs H1, H2 and H3 of 14G8 and CDRs L1, L2 and L3 of 14G8 except that positions H52 and L26 by Kabat numbering can each be independently N or S. Some antibodies include CDRs H1, H2 and H3 of 14G8 and CDRs L1, L2 and L3 of 14G8 wherein positions H52 and L26 are both occupied by N. Some antibodies include a mature heavy chain comprising CDRs H1, H2, H3 of 9D5 and a mature light chain comprising CDRs L1, L2 and L3 of 9D5, wherein positions H52 and L26 are S.

Unless otherwise apparent from the context reference to 14G8 or 9D5 should be understood as referring to any of the mouse, chimeric, veneered, and humanized forms of the mouse antibody. These antibodies specifically bind within approximately amino acid residues 89-97 (SEQ ID NO:113) of TTR. Such epitopes are buried in the native TTR tetramer and exposed in monomeric, misfolded, aggregated, or fibril forms of TTR.

Other antibodies can be obtained by mutagenesis of cDNA encoding the heavy and light chains of an exemplary antibody, such as 14G8 or 9D5. Monoclonal antibodies that are at least 70%, 80%, 90%, 95%, 96%, 97%, 98%, or 99% identical to 14G8 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention.

Antibodies including the CDRs of 14G8 or 9D5 as generally described above are characterized by their ability to bind to monomeric, misfolded, aggregated, or fibril forms of TTR preferentially over native tetrameric forms of TTR. In addition, these antibodies are characterized by their preferential immunoreactivity on TTR-mediated amyloidosis cardiac tissue but not on healthy cardiac tissue. Preferential binding or immunoreactivity can be relative e.g., at least 2 fold better or absolute (i.e., no binding or immunoreactivity to native TTR, or health cardiac tissue).

Some antibodies can inhibit or reduce aggregation of TTR, inhibit or reduce TTR fibril formation, reduce or clear TTR deposits or aggregated TTR, or stabilize non-toxic conformations of TTR in an animal model or clinical trial. Some antibodies can treat, effect prophylaxis of, or delay the onset of a TTR amyloidosis as shown in an animal model or clinical trial. Exemplary animal models for testing activity against a TTR amyloidosis include those described in Kohno et al., *Am. J. Path.* 150(4):1497-1508 (1997); Teng et al., *Laboratory Investigations* 81:385-396 (2001); Wakasugi et al., *Proc. Japan Acad.* 63B:344-347 (1987); Shimada et al., *Mol. Biol. Med.* 6:333-343 (1989); Nagata et al., *J. Biochem.* 117:169-175 (1995); Sousa et al., *Am. J. Path.* 161:1935-1948 (2002); and Santos et al., *Neurobiology of Aging* 31:280-289 (2010).

B. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition, such as, for example, by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by any conventional definition, such as, for example, by Kabat are identical.

Although humanized antibodies often incorporate all six CDRs (defined by any conventional definition, such as, for example, by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.*, 320: 415-428, 2002; Iwahashi et al., *Mol. Immunol.* 36:1079-1091, 1999; Tamura et al, *J. Immunol.*, 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and substantial reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

Examples of acceptor sequences for the heavy chain are the human mature heavy chain variable regions with NCBI accession codes BACO2114 and AAX82494.1 (SEQ ID NOs:3 and 4) and heavy chain variable regions of human Kabat subgroup 3. BACO2114 shares the same canonical form as mouse 9D5 heavy chain. Other examples of acceptor sequences for the heavy chain are the human mature heavy chain variable regions with NCBI accession codes AAD30410.1 and AAX82494.1 (SEQ ID NOs:63 and 4, respectively) and heavy chain variable regions of human Kabat subgroup 1. AAD30410.1 and AAX82494.1 include two CDRs having the same canonical form as mouse 14G8 heavy chain. Examples of acceptor sequences for the light chain are the human mature light chain variable region with NCBI accession code ABC66952 (SEQ ID NO:18) and light chain variable regions of human Kabat subgroup 3. ABC66952 includes two CDRs having the same canonical form as mouse 9D5 light chain. Other examples of acceptor sequences for the light chain are the human mature light chain variable regions with NCBI accession codes ABA71374.1 and ABC66952.1 (SEQ ID NOs:72 and 73, respectively) and light chain variable regions of human Kabat subgroup 2. ABA71374.1 and ABC66952.1 have the same canonical form as mouse 14G8 light chain.

If more than one human acceptor antibody sequence is selected, a composite or hybrid of those acceptors can be used, and the amino acids used at different positions in the humanized light chain and heavy chain variable regions can be taken from any of the human acceptor antibody sequences used. For example, the human mature heavy chain variable regions with NCBI accession codes BACO2114 and AAX82494.1 (SEQ ID NOs:3 and 4) were used as acceptor sequences for humanization of the 9D5 mature heavy chain variable region. Examples of positions in which these two acceptors differ include positions H19 (R or K), H40 (A or T), H44 (G or R), H49 (S or A), H77 (S or T), H82a (N or S), H83 (R or K), H84 (A or S), and H89 (V or M). Humanized versions of the 9D5 heavy chain variable region can include either amino acid at any of these positions. Similarly, the human mature heavy chain variable regions with NCBI accession codes AAD30410.1 and AAX82494.1 (SEQ ID NOs:63 and 4, respectively) were used as acceptor sequences for humanization of the 14G8 mature heavy chain variable region. Examples of positions in which these two acceptors differ include positions H82a (N or S), H83 (R or K), H84 (A or S), and H89 (V or M). Humanized versions of the 14G8 heavy chain variable region can include either amino acid at any of these positions. Similarly, the human mature light chain variable regions with NCBI accession codes ABA71374.1 and ABC66952.1 (SEQ ID NOs:72 and 73, respectively) were used as acceptor sequences for humanization of the 14G8 mature light chain variable region. An example of a position in which these two acceptors differ is position L18 (S or P). Humanized versions of the 14G8 light chain variable region can include either amino acid at this position.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine mature variable region framework residue and a selected human mature variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region)
(4) mediates interaction between the heavy and light chains.

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, J. Mol. Biol. 196:901-917 (1987); Thornton & Martin, J. Mol. Biol. 263:800815 (1996)). Framework residues that support antigen-binding loop conformations and play a role in fine-tuning the fit of an antibody to antigen are sometimes referred to as vernier residues (Foote & Winter, J. Mol. Biol 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 15 variable region framework positions were considered as candidates for substitutions in the eight exemplified Hu9D5 mature heavy chain variable regions and the five exemplified Hu9D5 mature light chain variable regions, as further specified in the examples: H42 (G42E), H47 (W47L), H69 (I69F), H82 (M82S), H82b (S82(b)L), H108 (T108L), L8 (P8A), L9 (L9P), L18 (P18S), L19 (A19V), L36 (Y36F), L39 (K39R), L60 (D60S), L70 (D70A), and L74 (K74R). Likewise, the following 11 variable region framework positions were considered as candidates for substitutions in the three exemplified Hu14G8 mature heavy chain variable regions and the three exemplified Hu14G8 mature light chain variable regions, as further specified in the examples: H1 (Q1E), H3 (Q3K), H47 (W47L), H105 (Q105T), L8 (P8A), L9 (L9P), L19 (A19V), L26 (N26S), L36 (Y36F), L60 (D60S), and L70 (D70A).

Here, as elsewhere, the first-mentioned residue is the residue of a humanized antibody formed by grafting Kabat CDRs or a composite Chothia-Kabat CDR in the case of CDR-H1 into a human acceptor framework (e.g., a composite or hybrid human acceptor framework), and the second-mentioned residue is a residue being considered for replacing such residue. Thus, within variable region frameworks, the first mentioned residue is human, and within CDRs, the first mentioned residue is mouse.

Exemplified Hu9D5 antibodies include any permutations or combinations of the exemplified mature heavy and light chain variable regions (e.g., VHv1/VLv1 or H1L1, VHv1/VLv2 or H1L2, VHv1/VLv3 or H1L3, VHv1/VLv4 or H1L4, VHv1/VLv5 or H1L5, VHv2/VLv1 or H2L1, VHv2/VLv2 or H2L2, VHv2/VLv3 or H2L3, VHv2/VLv4 or H2L4, VHv2/VLv5 or H2L5, VHv2b/VLv1 or H2bL1, VHv2b/VLv2 or H2bL2, VHv2b/VLv3 or H2bL3, VHv2b/VLv4 or H2bL4, VHv2b/VLv5 or H2bL5, VHv3/VLv1 or H3L1, VHv3/VLv2 or H3L2, VHv3/VLv3 or H3L3, VHv3/VLv4 or H3L4, VHv3/VLv5 or H3L5, VHv3bNLv1 or H3bL1, VHv3b/VLv2 or H3bL2, VHv3b/VLv3 or H3bL3, VHv3b/VLv4 or H3bL4, VHv3b/VLv5 or H3bL5, VHv4/VLv1 or H4L1, VHv4/VLv2 or H4L2, VHv4/VLv3 or H4L3, VHv4/VLv4 or H4L4, VHv4/VLv5 or H4L5, VHv4b/VLv1 or H4bL1, VHv4b/VLv2 or H4bL2, VHv4b/VLv3 or H4bL3, VHv4b/VLv4 or H4bL4, VHv4b/VLv5 or H4bL5, VHv5/VLv1 or H5L1, VHv5/VLv2 or H5L2, VHv5/VLv3 or H5L3, VHv5/VLv4 or H5L4, and VHv5/VLv5 or H5L5).

The invention provides formulations of variants of humanized 9D5 antibodies in which the humanized mature heavy chain variable region shows at least 90%, 95%, 96%, 97%, 98%, or 99% identity to a humanized Hu9D5VHv4b (SEQ ID NO:11) and the humanized mature light chain variable region shows at least 90%, 95%, 96%, 97%, 98%, or 99% identity to a Hu9D5VLv1 (SEQ ID NO:19). In some such antibodies, at least 1, 2, or all 3 of the backmutations or other mutations in Hu9D5 H4bL1 are retained. The invention also provides variants of the other exemplified humanized 9D5 antibodies. Such variants have mature light and heavy chain variable regions showing at least 90%, 95%, 96%, 97%, 98%, or 99% sequence identity to the mature light and heavy chain variable regions of the exemplified humanized 9D5 H1L1, H1L2, H1L3, H1L4, H1L5, H2L1, H2L2, H2L3, H2L4, H2L5, H2bL1, H2bL2, H2bL3, H2bL4, H2bL5, H3L1, H3L2, H3L3, H3L4, H3L5, H3bL1, Hb3L2, H3bL3, Hb3L4, H3bL5, H4L1, H4L2, H4L3, H4L4, H4L5, H4bL1, H4bL2, H4bL3, H4bL4, H4bL5, H5L1, H5L2, H5L3, H5L4, or H5L5 antibodies.

Variable regions framework positions are in accordance with Kabat numbering unless otherwise stated. Other such variants typically differ from the sequences of the exemplified Hu9D5 heavy and light chains by a small number (e.g., typically no more than 1, 2, 3, 5, 10, or 15) of replacements, deletions or insertions. Such differences are usually in the framework but can also occur in the CDRs.

Exemplified Hu14G8 antibodies include any permutations or combinations of the exemplified mature heavy and light chain variable regions (e.g., VHv1/VLv1 or H1L1, VHv1/VLv2 or H1L2, VHv1/VLv3 or H1L3, VHv2NLv1 or H2L1, VHv2/VLv2 or H2L2, VHv2/VLv3 or H2L3, VHv3/VLv1 or H3L1, VHv3/VLv2 or H3L2, and VHv3/VLv3 or H3L3).

The invention provides formulations of variants of humanized 14G8 antibodies in which the humanized mature heavy chain variable region shows at least 90%, 95%, 96%, 97%, 98%, or 99% identity to Hu14G8VHv2 (Hu14G8 H2) (SEQ ID NO:65) and the humanized mature light chain variable region shows at least 90%, 95%, 96%, 97%, 98%, or 99% identity to Hu14G8VLv3 (Hu14G8 L3) (SEQ ID NO:76). In some such antibodies, at least 1, 2, 3, 4, or all 5 of the backmutations or other mutations in Hu14G8 H2L3 are retained. The invention also provides variants of the other exemplified humanized 14G8 antibodies. Such variants have mature light and heavy chain variable regions showing at least 90%, 95%, 96%, 97%, 98%, or 99% sequence identity to the mature light and heavy chain variable regions of the exemplified humanized 14G8 H1L1, H1L2, H1L3, H2L1, H2L2, H2L3, H3L1, H3L2, or H3L3 antibodies.

In some antibodies, at least one of positions H1 and H47 in the Vh region is occupied by E and L, respectively. In some antibodies, positions H1 and H47 in the Vh region are occupied by E and L, respectively, as in Hu14G8VHv2 and Hu14G8VHv3. In some antibodies, at least one of positions H3 and H105 in the Vh region is occupied by K and T, respectively. In some antibodies, positions H3 and H105 in the Vh region are occupied by K and T, respectively, as in Hu14G8VHv1. In some antibodies, position L36 in the Vk region is occupied by F, as in Hu14G8VLv2. In some antibodies, at least one of positions L8, L9, L19, L26, L60, and L70 in the Vk region is occupied by A, P, V, S, S, and A, respectively. In some antibodies, positions L8, L9, L19, and L70 in the Vk region are occupied by A, P, V, and A, respectively, as in Hu14G8VLv1. In some antibodies, positions L26 and L60 in the Vk region are each occupied by S, as in Hu14G8VLv3. The CDR regions of such humanized antibodies can be identical or substantially identical to the CDR regions of the 14G8 mouse donor antibody. The CDR regions can be defined by any conventional definition (e.g., Chothia, or composite of Chothia and Kabat), for example, as defined by Kabat.

Variable regions framework positions are in accordance with Kabat numbering unless otherwise stated. Other such variants typically differ from the sequences of the exemplified Hu14G8 heavy and light chains by a small number (e.g., typically no more than 1, 2, 3, 5, 10, or 15) of replacements, deletions or insertions. Such differences are usually in the framework but can also occur in the CDRs.

A possibility for additional variation in humanized 14G8 or 9D5 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in humanized 14G8 or 9D5 variants (whether or not conservative) have no substantial deleterious effect on the binding affinity or potency of the humanized mAb, that is, its ability to bind to monomeric TTR (e.g., the potency in some or all of the assays described in the present examples of the variant humanized 14G8 or 9D5 antibody is essentially the same or at least 90% of, i.e., within experimental error, as that of murine 14G8 or 9D5 antibody).

C. Selection of Constant Region

The heavy and light chain variable regions of humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624, 821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine, such as in SEQ ID NO: 102. In some antibodies, the isotype is human IgG2 or IgG4.

An exemplary human light chain kappa constant region has the amino acid sequence of SEQ ID NO:104. The N-terminal arginine of SEQ ID NO:104 can be omitted, in which case light chain kappa constant region has the amino acid sequence of SEQ ID NO:105. Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Reference to a human constant region includes a constant region with any natural allotype or any permutation of residues occupying positions in natural allotypes. Exemplary heavy chain sequences including those having the amino acid sequences SEQ ID NOs:101-103 with SEQ ID NO:103, which is of IgG1 G1m3 allotype, preferred. Reference to a human constant region includes a constant region with any natural allotype or any permutation of residues occupying positions in natural allotypes.

D. Expression of Recombinant Antibodies

Antibodies can be produced by recombinant expression. Nucleic acids encoding the antibodies can be codon-optimized for expression in the desired cell-type (e.g., CHO or Sp2/0). Recombinant nucleic acid constructs typically include an expression control sequence operably linked to the coding sequences of antibody chains, including naturally-associated or heterologous promoter regions. The expression control sequences can be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase, to allow amplification of copy number of the nucleic acids encoding the antibody chains.

*E. coli* is a prokaryotic host particularly useful for expressing antibodies, particularly antibody fragments. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. It can be advantageous to use nonhuman cells. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Suitable expression control sequences are promoters derived from endogenous genes, cytomegalovirus, SV40, adenovirus, bovine papillomavirus, and the like. See Co et al., J. Immunol. 148:1149 (1992).

Having introduced vector(s) encoding antibody heavy and light chains into cell culture, cell pools can be screened for growth productivity and product quality in serum-free media. Top-producing cell pools can then be subjected to FACS-based single-cell cloning to generate monoclonal lines. Specific productivities above 50 pg or 100 pg per cell per day, which correspond to product titers of greater than 7.5 g/L culture, can be advantageous. Antibodies produced by single cell clones can also be tested for turbidity, filtration properties, PAGE, IEF, UV scan, HP-SEC, carbohydrate-oligosaccharide mapping, mass spectrometry, and binning assay, such as ELISA or Biacore. A selected clone can then be banked in multiple vials and stored frozen for subsequent use.

Methodology for commercial production of antibodies including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 6,114,148, 6,063,598, 7,569,339, WO2004/050884, WO2008/012142, WO2008/012142, WO2005/019442, WO2008/107388, and WO2009/027471, and U.S. Pat. No. 5,888,809).

Once expressed, antibodies can be purified according to standard procedures of the art, including protein A capture, column chromatography (e.g., hydrophobic interaction or ion exchange), low-pH for viral inactivation and the like (see generally, Scopes, Protein Purification (Springer-Verlag, NY, 1982)).

Antibodies used to prepare the disclosed formulations are typically isolated or purified, i.e., substantially free of cellular material or other contaminating proteins from the cells in which they are produced, or substantially free of chemical precursors or other chemicals when chemically synthesized. For example, an antibody that is substantially free of cellular material includes preparations of the antibody having less than about 30%, 25%, 20%, 15%, 10%, 8%, 5%, 2%, 1%, 0.5%, 0.1%, or less (by dry weight) of contaminating protein. When an antibody is recombinantly produced, it is also substantially free of culture medium such that culture medium represents less than about 30%, 25%, 20%, 15%, 10%, 8%, 5%, 2%, 1%, 0.5%, 0.1%, or less, of the volume of the protein preparation. When an antibody is produced by chemical synthesis, it is preferably substantially free of or separated from chemical precursors or other chemicals involved in the synthesis of the protein. Accordingly, such antibody preparations have less than about 30%, 25%, 20%, 15%, 10%, 8%, 5%, 2%, 1%, 0.5%, 0.1%, or less (by dry weight) of chemical precursors or compounds other than the antibody drug substance. Recombinantly expressed antibody can be purified by methods—such as, for example, affinity chromatography, acid treatment, depth filtration, anion exchange chromatography, cation exchange chromatography, nanofiltration, ultrafiltration, dialysis and diafiltration.

The purified antibody drug substance can be adjusted to a solution comprising any of the formulations described herein, diluted to the desired concentration and stored until ready for use. Optionally, the formulation can be stored in concentrated form until ready for use.

E. Conjugates

Antibodies used in the disclosed formulations can be coupled with a therapeutic moiety, such as a cytotoxic agent, a radiotherapeutic agent, an immunomodulator, a second antibody (e.g., to form an antibody heteroconjugate), or any other biologically active agent that facilitates or enhances the activity of a chimeric, veneered or humanized 14G8 or 9D5. Representative therapeutic moieties include drugs that reduce levels of TTR, stabilize the native tetrameric structure of TTR, inhibit aggregation of TTR, disrupt TTR fibril or amyloid formation, or counteract cellular toxicity.

The antibodies disclosed herein can also be coupled or conjugated to one or more other antibodies (e.g., to form antibody heteroconjugates). Such other antibodies can bind to different epitopes within TTR or a portion thereof or can bind to a different target antigen.

Antibodies can also be coupled with a detectable label. Such antibodies can be used, for example, for diagnosing a TTR amyloidosis, for monitoring progression of a TTR amyloidosis, and/or for assessing efficacy of treatment. Such antibodies are particularly useful for performing such determinations in subjects having or being susceptible to a TTR amyloidosis, or in appropriate biological samples obtained from such subjects. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as yttrium$^{90}$ (90Y), radiosilver-111, radiosilver-199, Bismuth$^{213}$, iodine ($^{131}$I, $^{125}$I, $^{123}$I, $^{121}$I), carbon ($^{14}$C), sulfur ($^{5}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rn, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies; nonradioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., Cell Biophys. 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, Cancer Chemother. Phannacol., 48 Suppl 1:S91-S95 (2001).

Therapeutic moieties, other proteins, other antibodies, and/or detectable labels may be coupled or conjugated, directly or indirectly through an intermediate (e.g., a linker), to an antibody of the invention. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., Immunol. Rev., 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

V. Formulations

Formulations (also known as pharmaceutical compositions) of the invention comprise any of the monoclonal antibodies described in this application including chimeric, veneered or humanized version of antibody 14G8 or 9D5, a buffer, one or more sugars and/or polyols and a surfactant, and have a pH within the range from about 4.5 to about 7.5. Other components (besides water in liquid formulations), such as, for example, arginine, lysine, NaCl, sorbitol or mannitol may or may not be present. The formulations can be in liquid or in lyophilized form. Liquid formulations can refer to a formulation before lyophilization or after reconstitution of a lyophilized formulation. In general, components of a formulation other than water occur in the same relative proportions by weight or moles in a lyophilized formulation as in a liquid formulation prior to lyophilization. Likewise, components of the formulation after reconstitution with water are in general in the same relative proportions as in the formulation prelyophilization or the lyophilized formulation but the absolute concentrations can change in proportion to the relative volumes of the formulation pre and post reconstitution. The volume post reconstitution can be the same, less or more than the volume prelyophilization. Usually the volume post reconstitution is the same within a factor of 5, 3, 2, 1.5, 1.2 or 1.1 of the volume prelyophilization. If for example, the volume post reconstitution is twice the volume prelyophilization the concentrations of components are approximately half that post reconstitution as prelyophilization.

In liquid formulations, the antibody can be present at a concentration within a range from about 10-100, 15-80, 20-65, 25-75, 40-65, 45-65 mg/mL, among others. In some formulations, the antibody is present at 55-65 mg/ml prelyophilization and 45-55 mg/ml after reconstitution. In some formulations, the antibody is present at 50 mg/ml after reconstitution.

Formulations include a buffer, such as, for example, citrate, histidine, phosphate or succinate, to confer a pH range of from about 4.5 to about 7.5, for example, a pH of 5.5, 5.6, 5.7, 5.8, 5.9, 6.0, 6.1, 6.2, 6.3, 6.4, 6.5, 6.6, 6.7, 6.8, 6.9, or 7.0. Some formulations have a pH of between about 5.5 to about 7.0, or about 5.5 to about 6.5, or about 5.5 to about 6.0, or about 6.0 to about 6.5, or about 6.0 to about 7.0, or about 5.75-6.25. Some formulations have a pH of about 6.0 and some formulations have a pH of about 6.5. In some formulations, histidine is present at a concentration within a range of about 10-30 mM, or 15-25 mM, for example at a concentration of about 10 mM, 20 mM or 25 mM. In some formulations, citrate is present at a concentration within a range of about 10-30 mM, for example at a concentration of about 10 mM or 20 mM. In some formulations, phosphate is present at a concentration of about 20 mM. In some formulations, succinate is present at a concentration of about 20 mM.

Formulations include a sugar/polyol, such as, for example, trehalose or sucrose. The sugar/polyol can be present at about 30 mM to about 260 mM, or about 150-350 mM, or about 200-300 mM, or about 220-260 mM, or about 230-250 mM, or about 205-240 mM, or about 205-250 mM or about 205-260 mM, or, or about 230-250 mM, or about 230-240 mM, or about 30 mM, about 205 mM or about 240 mM. In some formulations, trehalose is present at a concentration within a range of about 205-260 mM, about 205-250 mM, or about 205-240 mM, such as, for example, about 205 mM, about 230 mM or about 240 mM. In some formulations, sucrose is present at a concentration within a range of about 30-260 mM, about 30-250 mM, or about 30-240 mM, such as, for example, about 30 mM, about 230 mM or about 240 mM.

Formulations include a surfactant, such as, for example, polysorbate 20 (PS20), polysorbate 80 (PS80) or a poloxamer, for example, poloxamer 188 (also known as PX188, PLURONIC F68 or FLOCOR). The surfactant can be present at a concentration within the range from about 0.01%-0.1%, 0.02%-0.04%, or 0.03%-0.05% by weight. For example, the concentration can be 0.005%, 0.01%, 0.015%, 0.02%, 0.025%, 0.03%, 0.035%, 0.04%, 0.045%, or 0.05% by weight. Poloxamers are nonionic triblock copolymers composed of a central hydrophobic chain of polyoxypropylene (poly(propylene oxide)) flanked by two hydrophilic chains of polyoxyethylene (poly(ethylene oxide)). Some formulations include about 0.02% w/w PS20, about 0.02% w/w PS80 or about 0.04% poloxamer, for example, 0.04% poloxamer PX188 by weight.

Some such formulations are characterized by an osmolality in the range of about 270 mOsm/kg to about 330 mOsm/kg, such as, for example, about 335 mOsm/kg.

An exemplary formulation characterized by a pH within the range from about 5.0 to about 6.5 includes (a) a chimeric, veneered or humanized version of antibody 14G8 comprising a mature heavy chain variable region comprising three CDRs of SEQ ID NO:61 and a mature light chain variable region comprising three CDRs of SEQ ID NO:70, except that positions H52 and/or L26 by Kabat numbering can be N or S, or a chimeric, veneered or humanized version of anti-TTR antibody 9D5 comprising a mature heavy chain variable region comprising three CDRs of SEQ ID NO:1 and a mature light chain variable region comprising three CDRs of SEQ ID NO:16, wherein the antibody is present at a concentration within the range from about 25 mg/mL to about 75 mg/mL; (b) histidine, citrate, phosphate or succinate present at a concentration of about 20 mM; (c) sucrose or trehalose present at a concentration within the range from about 295 mM to about 240 mM or if the sugar is absent 160 mM arginine is present; and (d) a surfactant present at a concentration within the range from about 0.01% to about 0.1% by weight; provided that (i) if histidine or succinate buffer is present, the pH is about 6.0, (ii) if phosphate buffer is present, the pH is about 6.5, and if histidine and trehalose are present the surfactant is PS80 or PS20, provided that if PS20 is present, 25 mM L-arginine is also present.

Some formulations are essentially free of mannitol or sorbitol or both mannitol and sorbitol. In some formulations, the buffer comprises histidine, such as, for example, a histidine buffer. In some such formulations, the sugar can be present in a range from about 230 mM to about 240 mM. In some formulations, the sugar is sucrose and the surfactant is PS20 or PX188, for example PS20 at a concentration of 0.02% w/w or PX188 at a concentration of 0.04% w/w. In other formulations, the sugar is trehalose. In some formulations 160 mM arginine is present. The buffer of some formulations can be citrate. In some such formulations, the sugar is present at 230 mM. In some such formulations the surfactant is 0.02% PS20. Alternatively, the buffer can be phosphate. In some such formulations, sucrose is present. In other formulations, the buffer is succinate. In some such formulations sucrose is present. In some formulations comprising histidine, trehalose is present, for example at a concentration of 205 mM.

Exemplary formulations include about (a) 20 mM citrate, 230 mM trehalose and 0.02% w/w PS20 at pH5; (b) 20 mM histidine, 230 mM sucrose and 0.02% w/w PS20; (c) 20 mM phosphate, 230 mM sucrose and 0.02% w/w PS20 at pH6.5; (d) 20 mM citrate, 230 mM sucrose and 0.02% w/w PS20 at pH 6.5; (e) 20 mM histidine, 230 mM trehalose and 0.02% w/w PS80; (f) 20 mM histidine, 0.02% w/w PS20 and 160 mM L-arginine; (g) 20 mM histidine, 240 mM sucrose and 0.04% w/w PX188; (h) 20 mM succinate, 240 mM sucrose and 0.022% w/w PS20 at a pH of 6.0 and (i) 20 mM histidine, 205 mM trehalose, 0.02% w/w PS20 and 25 mM L-arginine. Some of such formulations consist essentially of the antibody and (a) 20 mM citrate, 230 mM trehalose and 0.02% w/w PS20 at pH5; (b) 20 mM histidine, 230 mM sucrose and 0.02% w/w PS20; (c) 20 mM phosphate, 230 mM sucrose and 0.02% w/w PS20 at pH6.5; (d) 20 mM citrate, 230 mM sucrose and 0.02% w/w PS20 at pH 6.5; (e) 20 mM histidine, 230 mM trehalose and 0.02% w/w PS80; (f) 20 mM histidine, 0.02% w/w PS20 and 160 mM L-arginine; (g) 20 mM histidine, 240 mM sucrose and 0.04% w/w PX188; (h) 20 mM succinate, 240 mM sucrose and 0.022% w/w PS20 at a pH of 6.0 or (i) 20 mM histidine, 205 mM trehalose, 0.02% w/w PS20 and 25 mM L-arginine. For example, the formulation can consist essentially of the antibody and about (a) 20 mM histidine, 240 mM sucrose and 0.04% w/w PX188; (b) 20 mM succinate, 240 mM sucrose and 0.02% w/w PS20 at a pH of 6.0; or (c) 20 mM histidine, 205 mM trehalose, 0.02% w/w PS20 and 25 mM L-arginine.

For example, the formulation can include (a) an antibody comprising a mature light chain having the amino acid sequence set forth as SEQ ID NO:65 and a mature heavy chain comprising an amino acid sequence set forth as SEQ ID NO:76, which is present at a concentration of about 45-65 mg/mL; (b) a histidine buffer at a concentration of about 15-25 mM; (c) sucrose at a concentration of about 220-260 mM; (d) poloxamer at a concentration of about 0.03-0.05%; and a pH of about 5.75-6.25. The formulation can include (a) an antibody comprising a mature light chain having the amino acid sequence set forth as SEQ ID NO:65 and a mature heavy chain comprising an amino acid sequence set forth as SEQ ID NO:76, which is present at a concentration of about 45-65 mg/mL; (b) a histidine buffer at a concentration of about 20 mM; (c) sucrose at a concentration of about 240 mM; (d) poloxamer at a concentration of about 0.04%; and a pH of about 6. For example, the formulation can consist essentially of an antibody comprising a mature light chain having the amino acid sequence set forth as SEQ ID NO:65 and a mature heavy chain comprising an amino acid sequence set forth as SEQ ID NO:76, and about 20 mM histidine, about 240 mM sucrose and about 0.04% w/w PX188.

Lyophilized formulations include any of the antibodies described herein, (b) a buffer, such as histidine; (c) a sugar/polyol such as sucrose; and (d) a surfactant, such as a poloxamer. In some lyophilized formulations, any residual water constitutes less than 5% by weight and in some such formulations less than 2 or 1% by weight of the formulation. The amounts of components depend on the volume lyophilized but can be for example about 100-300, 150-250 or 225-275 mg of antibody, about 15-35 or 15-19 mg buffer, and about 0.2-2.5 or 2.0-2.5 mg surfactant and about 400-490 mg of sugar or polyol. An exemplary lyophilized formulation includes 225-275 mg of a humanized 14G8 antibody, about 15-19 mg of L-histidine, about 400-490 mg sucrose and about 2.0-2.5 mg poloxamer, or the same components present in the same proportions but in different amounts. Lyophilized formulations can be prepared from any of the liquid formulations described above. One such lyophilized formulation consists essentially of about 250 mg of a humanized 14G8 antibody, about 16.8 mg of L-histidine, about 2.2 mg of poloxomer PX188 and about 445.3 mg of sucrose or different amounts of the same components in the same proportions. Lyophilized formulations can be stored frozen (e.g., −20° C.), in the cold (e.g., 4° C.) or at room temperature (e.g., 22° C.). An exemplary vial size for a lyophilized formulation is 20 ml.

Lyophilized formulations can be reconstituted by combining with suitable liquid, for example, sterile water. Lyophilized formulations can be reconstitutable with sterile water to a particle-free solution by eye within less than 5, 4, 3, 2 minutes. Reconstitution can be measured to the same volume (+/−20%) as that of the liquid formulation before lyophilization. Reconstitution to a certain desired final volume, for example, about 5 ml, can be achieved by adding a certain amount of liquid taking into account the volume occupied by the dry components. For example, some lyophilized formulations can be reconstituted to a total volume of about 5 ml by adding about 4.9 ml sterile water. The reconstitution can result in the components having approximately the same concentrations, relative and absolute, as before lyophilization or can result in approximately the same relative concentrations as before lyophilization but deceased or increased absolute concentrations. Some lyophilized formulations are constituted in a volume of about 1.2 fold the volume of the prelyophilized formulation resulting in a decrease of concentrations of about 17%. Some reconstituted formulations include an antibody concentration of about 40-60 mg/mL, for example, about 50 mg/mL; (b) a histidine buffer present at a concentration of about 15-25 mM, for example, about 20 mM; (c) sucrose present at a concentration of about 200-300 mM, for example, about 240 mM; (d) poloxamer present at a concentration of about 0.01% to about 0.1% by weight, for example, about 0.04% by weight; and (e) a pH of about 5.5-6.5, for example, about 6.0.

Liquid or reconstituted lyophilized formulations can be substantially isotonic implying an osmolality of about 250-350 mOsm/kg water. Some formulations have an osmolality of about 335 mOsm/kg. Some formulations have an osmolality of 270-300 mOsm/kg. Liquid or reconstituted lyophilized formulations can also be hypertonic >350 mOsm/kg water or hypotonic (<250 mOsm/kg water).

Liquid formulations (typically after reconstitution) can be added to infusion bag containing a diluent such as normal saline or Ringer's solution before administration to the patient. The volume of the infusion bag is usually relatively large (e.g., 50 ml to 1 L, or 100-500 ml) compared with the volume of the liquid formulation or constituted lyophilized formulation (e.g., 1-10 ml). Several liquids can be used in the infusion bag, such as normal saline, lactated Ringers solution, or 5% dextrose solution, each of which is substantially isotonic. In an exemplary regime about 5 ml of liquid or reconstituted lyophilized formulation is injected through the port of a 100-ml bag of normal saline and administered by iv infusion over a period of about an hour at a flow rate of about 1.75 ml/min.

Formulations intended for administration to humans are preferably made under good manufacturing practices (GMP) approved or approvable by the FDA or a regulatory agency for a country other than the United States, for example, the European Medicines Agency, for preparation of drugs for administration to humans. Typically, the formulations are sterile, for example, as accomplished by sterile filtration using a 0.2 μm or a 0.22 μm filter.

Stability of formulation can be assessed after storage in the lyophilized form followed by reconstitution. Exemplary formulation are stable at 38° C.-42° C. (e.g., as assessed by high performance size exclusion chromatography (HPSEC)) after storage in lyophilized form for at least about 30 days, formulations having stability at 20° C.-24° C. after storage for at least about 1 year, and formulations having stability at 2° C.-4° C. after storage for at least about 3 years. A formulation is considered stable if, after incubation at one or more of these specified combinations of time and temperature, it meets the below definition for low to undetectable fragmentation and/or low to undetectable aggregation. More particularly, the disclosed formulations exhibit low to undetectable levels of antibody aggregation and/or fragmentation, or a low or undetectable increase in antibody fragmentation and/or aggregation above an initial level (e.g., less than about 10% aggregation). Some formulations exhibit ≤about 5% combined aggregation and/or fragmentation. A formulation having low to undetectable levels of fragmentation contains at least about 80%, 85%, 90%, 95%, 97%, 98%, or 99%, of the total protein, for example, in a single peak as determined by high performance size exclusion chromatography (HPSEC), or in two peaks (one corresponding to each of the antibody heavy chains and antibody light chains) by reduced Capillary Gel Electrophoresis (rCGE), representing the non-degraded antibody, and containing no other single peaks having more than 5%, more than 4%, more than 3%, more than 2%, more than 1%, or more than 0.5% of the total protein each. A formulation having low to undetectable levels of aggregation contains no more than about 15%, no more than about 10%, no more that about 5%, no more than about 4%, no more than about 3%, no more than about 2%, no more than about 1%, or no more than about 0.5% aggregation by weight protein, as measured by high performance size exclusion chromatography (HPSEC). For example, in some formulations, less than about 10% of the anti-synuclein antibody is present as an aggregate. Stable formulations of the invention also show little or no loss of biological activity(ies) of antibody having, for example, binding affinity measurable by ELISAs and/or additional functional assay, that is at least about 50%, 55%, 60%, 65%, 70%, 75%, 80%, 85%, 90%, 95%, 98%, or 99% of an initial measurable value. Some formulations have a binding affinity that is from about 60% to about 140% of an initial measurable value of the reference material.

VI. Methods of Treatment

Formulations of the invention can be used for treating or effecting prophylaxis of a disease in a patient having or at risk for the disease mediated at least in part by transthyretin (TTR), and particularly by monomeric, misfolded, aggregated, or fibril forms of TTR. In some methods of treatment, the patient has been diagnosed with ATTR amyloidosis. Some such patients may have ATTR cardiac involvement and/or peripheral neuropathy involvement. Some patients have wild-type ATTR-cardiomyopathy in which normal, 'wild type' TTR proteins clump together and form amyloid deposits. Some patients have hereditary ATTR-cardiomyopathy. Some patients have hereditary polyneuropathy.

Formulations are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, for example, once every four weeks, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 3 months, 12 months, 5 years, 10 years, or the life of the patient.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the p<0.05 or 0.01 or even 0.001 level.

Effective doses vary depending on many different factors, such as means of administration, target site, physiological state of the subject, whether the subject is human or an animal, other medications administered, and whether treatment is prophylactic or therapeutic.

An exemplary dose range for antibodies can be from about 0.1 to 80 mg/kg, 0.1-30, 0.5-5, or 1-10 mg/kg body weight (e.g., 0.1, 0.2, 0.3, 1.0, 3.0, 10.0 or 30.0 mg/kg) or 10-5000, e.g., 10-1500 mg as a fixed dosage. Some methods increase the dose with time. The dose can be increased in increments of one (i.e., one change of dose), two, three or more. There can be 1, 2, 3 or more dosages at each level prior to the final level. The final level can be continued for e.g., at least 15 dosages. For example, an initial dose can be in the range 0.1 mg/kg to 3 mg/kg for three infusions one every 28 days, then three infusions at an intermediate level also every 28 days, followed by dosing at a higher level of e.g., 10-30 mg/kg every 38 hours, optionally at least 15 times. The dosage depends on the condition of the patient and response to prior treatment, if any, whether the treatment is prophylactic or therapeutic and whether the disorder is acute or chronic, among other factors.

Formulations can be administered via a peripheral route. Routes of administration include topical, intravenous, oral, subcutaneous, intraarterial, intracranial, intrathecal, intraperitoneal, intranasal or intramuscular. For example, routes for administration of the formulations provided herein can be intravenous or subcutaneous. Intravenous administration can be, for example, by infusion over a period within a range of 30-180 minutes, such as 30-90 minutes, 60-120 minutes, or 90-180 minutes. This type of injection is most typically performed in the arm or leg muscles. In some such methods, the patient may be premedicated with a pain reliever or an antihistamine or diphenhydramine. For example, diphenhydramine can be administered to the patient within a range of about 30 to 90 minutes prior to the antibody administration. Some patients may be premedicated with acetaminophen within a range of about 30 to 90 minutes prior to the antibody administration. In some methods, agents are injected directly into a particular tissue where deposits have accumulated, for example, intracranial injection.

Liquid formulations can be administered directly to the patient, for example, by subcutaneous injection or by infusion. Lyophilized formulations are reconstituted in a liquid, for example, sterile water prior to administration to the patient. For infusion, the liquid formulation is introduced into a bag of isotonic fluid, for example, normal saline. For example, a lyophilized dosage form of the formulation can be reconstituted to a volume of about 5.0 mL with sterile water, and diluted in normal saline for infusion, for example, for a total infusion volume of 100 mL, 250 mL, or 500 mL.

The regimes comprising the formulated antibodies herein can be administered in combination with other therapies to a subject having or at risk of a transthyretin-mediated amyloidosis. Optionally, in addition to administering the formulated antibody herein, such therapies are administered sequentially or separately to a subject in need thereof. Optionally, the subject no longer receives the treatment with the pharmaceutical formulation comprising the formulated antibodies.

These therapies include TTR stabilizers, such as tafamidis and diflunisal, gene therapies to suppress TTR expression and subsequent TTR protein production including use of small interfering RNAs, such as patisiran and inotersen, and antisense oligonucleotides, as well as amyloid degraders including 4'-iodo-4'-deoxydoxorubicin (IDOX), doxycycline, tauroursodeoxycholic acid (TUDCA), and cyclodextrin (CyD) and anti-SAP antibodies.

TTR stabilizers, such as tafamidis (Pfizer's Vyndaquel) (see, e.g., WO2011116123, U.S. Pat. No. 9,150,489) and diflunisal (generic), can be used to maintain TTR's normal soluble tetrameric structure and to limit the number of TTR monomers in the circulation. For example, tafamidis is under active investigation as a novel compound that binds to the thyroxine-binding sites of the TTR tetramer, inhibiting its dissociation into monomers and blocking the rate-limiting step in the TTR amyloidogenesis cascade. Diflunisal binds and stabilizes common familial TTR variants against acid-mediate fibril formation.

RNA inhibiting therapies bind the targeted mRNA and thereby suppress in mRNA expression and prevent translation of the corresponding protein. The clinical results so far have indicated that small interfering RNA, e.g., patisiran or revusiran (see, e.g., WO 2016033326), and antisense oligonucleotide, e.g., inotersen (see, e.g., U.S. Pat. Nos. 8,101,743 and 9,061,044), are potent approaches to eliminate TTR protein production by triggering the degradation of TTR mRNA or inhibiting translation.

Patisiran, a siRNA therapy is being investigated in a Phase III multicenter clinical trial for hereditary ATTR amyloidosis patients with polyneuropathy (hATTR Also under investigation, is inotersen (IONIS-TTRRx), a subcutaneously administered anti sense oligonucleotide targeting the same patient group as patisiran.

Antisense oligonucleotides (ASOs) are under clinical investigation for their ability to inhibit hepatic expression of amyloidogenic TTR protein. Currently, the ASO compound, ISIS-TTR$_{Rx}$, is under investigation in a phase 3 multicenter, randomized, double-blind, placebo-controlled clinical trial in patients with familial amyloid polyneuropathy (FAP).

Amyloid degraders such as the doxycycline/tauroursodeoxycholic add combination therapy have the potential to remove TTR amyloid deposited in the organs. For example, combined doxycycline and tauroursodeoxycholic acid (TUDCA) disrupt TTR amyloid fibrils and appeared to have an acceptable safety profile in a small phase 2 open-label study among 20 TTR patients.

Another example of TTR degraders are anti-SAP antibodies. Anti-SAP antibodies are antibodies against a normal non-fibrillar glycoprotein SAP, which promotes a giant cell reaction that removes visceral amyloid deposits.

X. Examples

Example 1. Pre-Formulation Testing at Low Concentration

Pre-formulation development studies were conducted on a humanized 14G8 antibody having the mature heavy chain sequence of SEQ ID NO:82 (except that the C-terminal lysine can be absent) and the mature light chain sequence of SEQ ID NO:86. Pre-formulation testing was performed with the humanized 14G8 antibody in 20 formulations containing combinations of various buffers in a pH range of from about 4.5 to about 7.0 with and without certain sugars, surfactants and other excipients.

The properties of the formulations were tested by methods including visual inspection, dynamic light scattering (DLS) micro-flow imaging (MFI), differential scanning fluorimetry (DSF), differential scanning calorimetry (DSC), and high performance size exclusion chromatography (HP-SEC).

The buffers tested were citrate, histidine, succinate and phosphate in a concentration ranging from about 10 mM to about 20 mM. The sugars tested were trehalose and sucrose in a concentration ranging from about 205 mM to about 230 mM. Formulations having trehalose in a citrate or histidine buffer were tested, as were formulations having sucrose in any of the four buffers.

The surfactants tested were PS20, PS80 and poloxamer 188 in a concentration ranging from about 0.02% w/w to about 0.04% w/w. PS20 was tested in various formulations. Poloxomer and PS80 were tested only in one formulation, which contained trehalose in a histidine buffer.

Additional excipients tested were L-arginine, L-lysine and NaCl in concentrations ranging from about 25 mM to about 160 mM in histidine formulations with and without trehalose or PS20.

The results of the formulations under each of these tests (F1-F20) were assigned values according to the relative extent of change compared to T0. Most favorable were circumstances under which no changes were observed. Unacceptable were those circumstances under which large changes were observed. Additional values were assigned to circumstances under which small changes were observed and under which intermediate changes were observed. Tables 2-3 report the results of subjecting the samples to freeze-thawing stress (T-FT) and storage for 1 week at 50° C. (T-50) as determined by visual inspection, MFI, DLS and HP-SEC. Table 2 provides a list of common properties of formulations for which no large changes were observed in any of the tests. Overall, formulations F13 and F20, both of which lacked surfactant, showed the worst performance upon stressing. Formulations with a pH of 4.5 or less or 7.0 or greater generally did not perform as well as other formulations. 10 mM buffer concentrations did not perform as well as 20 mM buffer concentrations. The presence of sugars was beneficial, although formulations with no sugars and a high concentration of L-arginine performed better than formulations lacking both sugars and high concentrations of L-arginine.

Table 2 provides a list of conclusions from formulations exhibiting respectable performance in all tests (i.e., no large changes).

TABLE 2

| Conclusion | Details |
|---|---|
| Suitable pH Range | 5-6.5 |
| Suitable buffers | 20 mM citrate, histidine or phosphate |
| Presence of sugars or high concentration of L-arginine is beneficial | 230 mM trehalose or sucrose |
| Surfactant is required | 0.02% w/w PS20 or PS80 |

Table 3 provides a list of specific excipient combinations that did not show large changes under any particular test.

TABLE 3

| Formulation | pH | Buffer | Excipient 1 (sugar) | Excipient 2 (surfactant) | Other excipients |
|---|---|---|---|---|---|
| F2 | 5.0 | 20 mM citrate | 230 mM trehalose | 0.02% w/w PS20 | — |
| F8 | 6.0 | 20 mM histidine | 230 mM sucrose | 0.02% w/w PS20 | — |
| F10 | 6.5 | 20 mM phosphate | 230 mM sucrose | 0.02% w/w PS20 | — |
| F11 | 6.5 | 20 mM citrate | 230 mM sucrose | 0.02% w/w PS20 | — |
| F14 | 6.0 | 20 mM histidine | 230 mM trehalose | 0.02% w/w PS80 | — |
| F16 | 6.0 | 20 mM histidine | — | 0.02% w/w PS20 | 160 mM L-arginine |

However, because all of the formulations exhibited intermediate changes in at least one of the tests, further modifications of the formulations were performed, as discussed in Example 2, to create formulations that would provide the most stabilizing conditions for the antibody.

Example 2: Formulation Screening at 50 mg/ml

Based on the results from the pre-formulation screening, formulations F21-F31 listed in Table 4 were subjected to testing at a concentration of 50 mg/ml antibody.

TABLE 4

Table 4: List of Formulations Tested at 50 mg/ml

| Formulation | pH | Buffer | Excipient 1 (sugar) | Excipient 2 (surfactant) | Other excipients |
|---|---|---|---|---|---|
| F21 | 6.5 | 25 mM histidine | 230 mM trehalose | 0.02% w/w PS20 | — |
| F22 | 6.0 | 20 mM histidine | 240 mM sucrose | 0.02% w/w PS20 | — |
| F23 | 6.5 | 20 mM histidine | 240 mM sucrose | 0.02% w/w PS20 | — |
| F24 | 7.0 | 20 mM histidine | 240 mM sucrose | 0.02% w/w PS20 | — |
| F25 | 6.0 | 20 mM histidine | 240 mM sucrose | 0.04% w/w PX188 | — |
| F26 | 6.0 | 20 mM phosphate | 240 mM sucrose | 0.02% w/w PS20 | — |
| F27 | 6.0 | 20 mM succinate | 240 mM sucrose | 0.02% w/w PS20 | — |
| F28 | 6.0 | 20 mM histidine | 240 mM trehalose | 0.02% w/w PS20 | — |

TABLE 4-continued

Table 4: List of Formulations Tested at 50 mg/ml

| Formulation | pH | Buffer | Excipient 1 (sugar) | Excipient 2 (surfactant) | Other excipients |
|---|---|---|---|---|---|
| F29 | 6.0 | 20 mM histidine | 30 mM sucrose | 0.02% w/w PS20 | 220 mM mannitol |
| F30 | 6.0 | 20 mM histidine | 205 mM trehalose | 0.02% w/w PS20 | 25 mM L-arginine |
| F31 | 6.0 | 20 mM histidine | 205 mM trehalose | 0.02% w/w PS20 | 25 mM L-lysine |

The samples were subjected to visual inspection, glass transition temperature, MFI, HP-SEC and cIEF tests as appropriate after preparation (T-liquid), lyophilization (T0), two weeks storage in liquid state at 25° C. and one month and three months storage of lyophilized forms at 2-8° C., 25° C. and 40° C. The results of the formulations under each of these tests were assigned values of "bad", "acceptable", "good" and "very good". Acceptable formulations had 4000-6000 particles ≥10 μm/ml (F27), greater than 94.0% monomer and less than 3% high molecular weight species (F22-F27 and F30), and greater than 74% main isoforms after storage for three months at 40° C./75% r.h. Table 5 provides a list of common properties of formulations that did not receive a "bad" score in any of the tests performed.

TABLE 5

Table 5: List of conclusions from formulations exhibiting acceptable to very good performance in all tests.

| Conclusion | Details |
|---|---|
| Optimal pH | 6.0 |
| Optimal buffers | 20 mM histidine or succinate |
| Optimal sugars | 205-240 mM trehalose or sucrose |
| Optimal surfactant | 0.02%-0.04% w/w PS20 or PX188 |

TABLE 6

Table 6: List of formulations exhibiting acceptable to very good performance in all tests.

| Formulation | pH | Buffer | Excipient 1 (sugar) | Excipient 2 (surfactant) | Other excipients |
|---|---|---|---|---|---|
| F25 | 6.0 | 20 mM histidine | 240 mM sucrose | 0.04% w/w PX188 | — |
| F27 | 6.0 | 20 mM succinate | 240 mM sucrose | 0.02% w/w PS20 | — |
| F30 | 6.0 | 20 mM histidine | 205 mM trehalose | 0.02% w/w PS20 | 25 mM L-arginine |

Formulation F25 was found to be superior to all formulations tested, exhibiting less than 4000 particles/ml, greater than 96.0% monomer with less than 2.5% high molecular weight species, and 77% main isoforms (determined by cIEF) in the liquid formulation stored for 2 weeks at 25° C. and in the lyophilized forms stored for 1 month and 3 months at temperatures tested (40° C.). Based on these studies, Formulation 25 (20 mM histidine-HCl, 240 mM sucrose, 0.04% poloxamer, pH 6.0) was identified as the lead candidate for further development as described in Example 3.

Example 3: Preparation and Characterization of Formulation F25

Sample Preparation:

The liquid formulation prelyophilization was 61 mg/ml humanized 14G8, 20 mM histidine, 240 mM sucrose and 0.04% poloxamer. After lyophilization, the formulation was reconstituted to an antibody concentration of about 50 mg/ml.

The frozen starting material as described above was thawed in a water bath at 20° C. After thawing, material of two batches was mixed and protein concentration was determined. The aliquot for the second batch was frozen again to −80° C. until further usage. The sample concentration was adjusted by dilution with formulation buffer to obtain a target concentration of 50 mg/ml. Surfactant was added by spiking an aliquot of a concentrated stock solution in water directly into the formulation. Then, the sample was filtered through 0.22-μm PVDF membrane filters under a laminar flow hood. Finally, the filtered formulation was filled into pre-cleaned glass type I, 20R vials; each vial with a filling volume of 5 ml prior to loading onto freeze-dryer shelves.

Lyophilization:

Lyophilization of the samples was performed by using an Epsilon 2-12D pilot scale freeze-dryer (Martin Christ, Osterode, Germany). The lyophilization processes were based on the critical product temperatures of the chosen formulation (Tg' of −25.7° C. and a Tconset of −25.3° C.) and were developed for the active DP. The starting point for selected conditions to perform freeze drying was based on published guidelines (see e.g., Carpenter J F et al., Pharm Res. 1997 August, 4(8):969-75; Jameel F et al., Book chapter 30 in Formulation and Process Development Strategies for Manufacturing Biopharmaceuticals, published online: August 2010; and Remmele R L et al, Curr Pharm Biotechnol., 2012 March, 13(3):471-96). A standard freezing protocol was applied that is used for sucrose-based formulations by cooling to −45° C. with a rate of 0.5° C./minute. Initial guess for the shelf temperature during primary drying was maintained such that resulting product temperature is at or below the measured Tg' and measured collapse temperature of the formulation, in order to avoid collapse during primary drying. A chamber pressure of 0.13 mbar was chosen so that vacuum was within a practical range for drying at both a laboratory, pilot and commercial scale (recommended range of chamber pressure is 0.07-0.20 mbar), also considering the solids content of the formulation. Thus, the chamber pressure selected would ensure optimum sublimation and completion of primary drying within a reasonable period of time (on a lab scale, approximately 25 h). Shelf temperature during secondary drying was maintained at 25° C. under a chamber pressure of 0.13 mbar. For sucrose-based formulations with a high solids content. A shelf temperature of 25-45° C. during secondary drying should be appropriate for water desorption within in a reasonable time to achieve a low moisture content without an adverse impact on product quality (Pikal M J, International Journal of Pharmaceutics, 1990, 60:203-217; Startzel P et al., Journal of Pharmaceutical Sciences, 2015, 104:2345-2358; and Davis J M et al, Pharm Dev Technol. 2013, July-August, 18(4): 883-96). Ramp rates from primary to secondary drying were kept low (conservative) to avoid product temperature rise above shelf temperature (and possibly above Tg) during initial phases of secondary drying when moisture content in the product are high. The vacuum during the freeze-drying process was controlled by a capacitance (MKS) gauge. During the freeze-drying process, the Plexiglas door of the freeze-dryer was covered with a stainless steel shield to reduce heat radiation. In order to produce samples of different residual moistures and to characterize the drying behavior of the formulation in the course of the processes, single shelf closure was performed at the following sampling time points: 1) T-IPC1: at the end of primary drying; 2) T-IPC2: after the ramp to the secondary drying temperature (25° C.); 3) T-IPC3: after 5 h (DevRun #1) and 6 h (DevRun #2) of secondary drying at 25° C.; 4) T-final (=T0): at the end of secondary drying.

Analytical Charaterization of Lyophilized Formulation 25:

Optical Appearance:

In general, freeze-dried formulations in the course of drying (T-IPC1, T-IPC2, T-IPC3) showed excellent retention of the cake structure with off-white cakes.

Karl Fischer Titration:

The water content of the lyophilized cakes was determined using the coulometric Karl Fischer titrator Aqua 40.00 (Analytik Jena GmbH, Jena, Germany), which is equipped with a headspace module. For the measurement, about 15 mg sample were weighed into 2R glass vials in a glove box under humidity controlled conditions (rel. humidity <5%) and heated to 120° C. in the oven connected to the reaction vessel via a tubing system. The evaporated water was transferred into the titration solution and the amount of water was determined. The measurement was performed until no more water evaporation was detectable. Water content of the sample was calculated considering environmental moisture as determined in three blanks. At the end of both cycles, all samples had a residual moisture of ≤1.0%.

Differential Scanning Calorimetry (DSC):

Differential scanning calorimetry (DSC) in a Mettler Toledo DSC1_943 (Mettler Toledo, Giessen, Germany) was used to determine thermal events of the frozen formulation, e.g. the glass transition temperature of the lyophilized products (Tg). For the physico-chemical analysis of the dried product 10 mg of the freeze-dried product were analyzed in crimped Al-crucibles (Mettler Toledo, Giessen, Germany). The samples were cooled to 0° C. with 10 K/min and reheated to 120° C. with a scanning rate of 10 K/min. This temperature profile was repeated in a second cycle. The midpoint of the endothermic shift of the baseline during the heating scan was taken as Tg. The glass transition temperature varied inversely with residual moisture content.

X-Ray Powder Diffraction (XRD):

Wide angle X-ray powder diffraction (XRD) was used to study the morphology of lyophilized products. The X-ray diffractometer Empyrean (Panalytical, Almelo, The Netherlands) equipped with a copper anode (45 kV, 40 mA, Kα1 emission at a wavelength of 0.154 nm) and a PIXcel3D detector was used. Approximately 100 mg of the freeze-dried samples were analyzed in reflection mode in the angular range from 5–45° 2θ, with a step size of 0.04° 2θ and a counting time of 100 seconds per step. The morphology/crystallinity of the freeze-dried cakes of samples generated in the course of freeze drying (T-IPC1, T-IPC2, T-IPC3, T0) in both lyophilization process were determined by XRD. All samples exhibited a fully amorphous cake structure and no distinct peaks referring to crystallization of buffer salts or other excipients were detected. In all the samples, only one broad peak with a maximum at roughly 20 degrees 2θ was observed, which is characteristic of amorphous samples (Liu W et al, AAPS Pharmscitech, 2005, Vol. 6(2)).

Reconstitution of the Lypophilized Formulations: The reconstitution volume was determined by weighing of four vials per shelf pre and post lyo for both cycles to determine the mass of the removed water. Samples of the lyophilized products (placebo and active vials) were reconstituted under a laminar flow hood according to the following procedure: the required amount of ultrapure water (Milli-Q water) was added to the lyophilized product (into the center of the vial) by using a pipette. The vial was carefully slewed (shaking was avoided). The reconstitution time was measured as the time to achieve a full reconstitution of the lyophilized product after addition of the liquid. The reconstitution behavior was judged, mainly with respect to foaming. The reconstitution time (dissolution of all visible solids) of samples generated in the course of freeze drying (T-IPC1, T-IPC2, T-IPC3, T0) in both lyophilization processes as determined after addition of ultra-pure water to the lyophilizates is shown in Table 7. After addition of 4.5 ml of ultra-pure water the reconstitution of the end products was completed in less than 4 minutes.

TABLE 7

Table 7: Reconstitution times of samples generated at different time points during lyophilization

| | Reconstitution time [mm:ss] | |
|---|---|---|
| Time Point | DevRun #1 | DevRun #2 |
| T-liquid | — | — |
| T-IPC1 | 01:55 | 04:26 |
| T-IPC2 | 02:33 | 04:20 |
| T-IPC3 | 02:32 | 05:03 |
| T-final | 01:35 | 03:52 | pH:

Formulation pH was measured with a calibrated pH meter (SevenEasy®, Mettler Toledo AG, Schwerzenbach, Switzerland) using a low ionic strength electrode (InLab® Pure Pro) or a high/normal ionic strength electrode (InLab® Micro). The pH-value of all samples generated in the course of freeze drying (T-IPC1, T-IPC2, T-IPC3, T0) in both lyophilization processes after reconstitution is shown in Table 8. No change in pH was observed before and after lyophilization. After preparation (T-liquid), the target pH-value of 6.0 was achieved in both cycles and the pH-values remained within the target range of 6.0±0.1 in the course and after the two lyophilization processes.

TABLE 8

Table 8: pH-values of samples generated at different time points during lyophilization.

| Time point | Visual Score | |
|---|---|---|
| | DevRun#1 | DevRun#2 |
| T-liquid | 6.0 | 6.0 |
| T-IPC1 | 6.1 | 6.0 |
| T-IPC2 | 6.0 | 6.0 |
| T-IPC3 | 6.0 | 6.0 |
| T-final | 6.0 | 5.9 |

Osmolality:

Osmolality of the samples was measured by method of freezing-point depression using a Knauer Automatic Semi-Micro Osmometer No. A0300 (Knauer, Berlin, Germany). The osmolality of all samples generated in the course of freeze drying (T-IPC1, T-IPC2, T-IPC3, T0) in both lyophilization processes after reconstitution is shown in Table 9. The osmolality after preparation (T-liquid) was within the physiological range (270-330 mOsmol/kg) and remained basically unchanged in the course and after lyophilization.

TABLE 9

Table 9: Osmolality of samples generated at different time points during lyophilization.

| Time point | Osmolality [mOsmol/kg] | |
|---|---|---|
| | DevRun#1 | DevRun#2 |
| T-liquid | 317 | 310 |
| T-IPC1 | 314 | 317 |
| T-IPC2 | 321 | 314 |
| T-IPC3 | 319 | 315 |
| T-final | 320 | 314 |

UV-Vis Spectroscopy:

A Tecan Safire$^2$ plate reader (Tecan Austria GmbH, Grödig, Austria) was used for concentration determination and turbidity assessment. Triplicates of 200 µl of the samples were prepared in 96 well plates (Corning Incorporation, NY, USA). After the measurement, the obtained absorption values were corrected for the pathlength and subtracted with corresponding blank. All samples were diluted to 0.5$^{-1}$ mg/ml in placebo buffer prior to the measurement. An extinction coefficient based on a concentration of 1 mg/ml at a pathlength of 1 cm of 1.404 ml cm$^{-1}$ at 280 nm was used for concentration calculation (information from Rentschler). Furthermore, an increase in optical density at 350 nm from light scattering of particles was used to evaluate the turbidity of the samples. To calculate the aggregation index (A.I.) the following equation was used: A.I.=100*(A350/(A280−A350)). The protein concentration of all samples (n=3) generated in the course of freeze drying (T-IPC1, T-IPC2, T-IPC3, T0) in both lyophilization processes after reconstitution is shown in Table 10. After preparation (T-liquid), the target concentration of 50±2.5 mg/ml was achieved for all samples and remained within the specification in the course and after lyophilization.

TABLE 10

Table 10: Protein concentration of samples generated at different time points during lyophilization.

| Time point | Protein concentration [mg/ml] | |
|---|---|---|
| | DevRun#1 | DevRun#2 |
| T-liquid | 48.8 ± 0.5 | 49.7 ± 0.4 |
| T-IPC1 | 48.3 ± 0.5 | 51.8 ± 0.1 |
| T-IPC2 | 47.8 ± 0.3 | 51.5 ± 0.3 |
| T-IPC3 | 47.9 ± 0.5 | 51.2 ± 0.2 |
| T-final | 51.0 ± 0.3 | 48.7 ± 0.1 |

High Performance Size Exclusion Chromatography (HP-SEC):

HP-SEC was performed according to the information obtained from Rentschler. Of the Bio-Rad gel filtration standard (GFS) and the antibody samples, an amount of 20 µg was loaded on the column (concentration of 1 mg/ml was used). As shown in Table 11, no change in low molecular weight solids was observed and with lyophilization, and change in high molecular weight solids was slight or none. Thus, lyophilization retains the vast majority of antibody in monomer form.

TABLE 11

Table 11: Relative content of different species in samples generated at different time points during lyophilization.

| Time point | Monomer [%] | | HMWS [%] | | LMWS [%] | | Total peak area [mAu* min] | |
|---|---|---|---|---|---|---|---|---|
| | DevRun #1 | DevRun #2 | DevRun #1 | DevRun #2 | DevRun #1 | DevRun #2 | DevRun #1 | DevRun #2 |
| T-liquid | 97.4 ± 0.0 | 97.4 ± 0.0 | 1.1 ± 0.0 | 1.2 ± 0.0 | 1.5 ± 0.0 | 1.4 ± 0.0 | 762.7 ± 0.4 | 746.8 ± 85.2 |
| T-IPC1 | 97.6 ± 0.0 | 97.3 ± 0.0 | 0.9 ± 0.0 | 1.3 ± 0.0 | 1.5 ± 0.0 | 1.4 ± 0.0 | 757.6 ± 0.3 | 649.9 ± 65.5 |
| T-IPC2 | 97.6 ± 0.1 | 97.3 ± 0.0 | 0.9 ± 0.0 | 1.3 ± 0.0 | 1.5 ± 0.1 | 1.4 ± 0.1 | 761.3 ± 0.3 | 687.9 ± 8.2 |
| T-IPC3 | 97.6 ± 0.0 | 96.7 ± 0.0 | 0.9 ± 0.0 | 1.9 ± 0.0 | 1.5 ± 0.0 | 1.3 ± 0.0 | 753.6 ± 2.9 | 534.3 ± 119.2 |
| T-Final | 97.6 ± 0.0 | 96.7 ± 0.0 | 0.9 ± 0.0 | 1.9 ± 0.0 | 1.5 ± 0.1 | 1.4 ± 0.0 | 770.3 ± 0.3 | 503.9 ± 82.6 |

Various changes in form and details can be made therein without departing from the spirit and scope of the invention. Unless otherwise apparent from the context, any embodiment, aspect, element, feature, step or the like can be used in combination with any other. Insofar as information associated with a citation may change with time, the information associated with the citation at the earliest effective filing date is meant, the earliest effective filing date for a citation meaning the filing date of the present application or earlier priority application disclosing the citation. All references, issued patents and patent applications cited within the body of the instant specification are hereby incorporated by reference in their entirety, for all purposes. Any embodiment, aspect, feature, element, step or the like can be combined with any other unless the context indicates otherwise. When a composition is said to comprise certain specified components, the application should be read unless the context requires otherwise as disclosing that in the alternative, the composition may consist of or consist essentially of the specified components. For example, when an antibody chain is said to have an amino acid sequence comprising a specified SEQ ID NO., it should be understood unless the context requires otherwise that alternatively the antibody chain can consist of or consist essentially of the SEQ ID NO.

"Consisting essentially of" is used in accordance with convention to designate the basic and novel components of a composition. Unless otherwise apparent from the context, water can also be present in any amount. Other components may be present in minor amounts having no significant effect on the activity or stability of the composition. "Essentially free of" is likewise defined to indicate a component may be present, if at all, only in such minor amounts. When a component of a composition is said to be present at a concentration of "about" a designated value or range of values, the application should be read as disclosing in the alternative that the component can be present at the designated value or range of values.

What is claimed is:

1. A pharmaceutical formulation comprising:
   (a) a monoclonal antibody comprising a mature heavy chain comprising the amino acid sequence of SEQ ID NO:82 except the C-terminal lysine may be absent and a mature light chain comprising the amino acid sequence of SEQ ID NO:86, wherein the antibody is present at a concentration within the range from about 25 mg/mL to about 75 mg/mL;
   (b) a histidine buffer present at a concentration of about 20 mM;
   (c) sucrose present at a concentration of about 220 to about 260 mM, and
   (d) poloxamer 188 (PX188) present at a concentration within the range from about 0.03% to about 0.050% by weight;
   wherein the formulation is characterized by a pH within the range from about 5.5 to about 6.5.

2. The pharmaceutical formulation of claim 1, comprising:
   20 mM histidine, 240 mM sucrose and 0.04% w/w PX188.

3. The pharmaceutical formulation of claim 2, wherein the formulation consists essentially of the antibody and about 20 mM histidine, 240 mM sucrose and 0.04% w/w PX188.

4. The formulation of claim 1, wherein the antibody is present at about 50 mg/ml.

5. A lyophilized formulation of an antibody prepared by lyophilizing the formulation of claim 1.

6. The lyophilized formulation of claim 5, which is reconstitutable with water to a pH of between about 5.5 to about 6.5.

7. A method of reconstituting the lyophilized formulation of claim 5 comprising:
   combining the lyophilized formulation with sterile water to produce a liquid formulation.

8. A sterile lyophilized dosage form of an antibody formulation in a 20 ml vial, which is used for reconstituting the antibody formulation to a volume of 5.0 mL, consisting essentially of:
   (i) an antibody within a range of about 225-275 mg;
   (ii) histidine within a range of about 15-19 mg;
   (iii) poloxamer 188 (PX188) within a range of about 2-2.5 mg; and;
   (iv) sucrose within a range of about 400-490 mg;
   wherein the antibody comprises a mature heavy chain comprising the amino acid sequence of SEQ ID NO:82 except the C-terminal lysine may be absent and a mature light chain comprising the amino acid sequence of SEQ ID NO:86.

9. The sterile lyophilized dosage form of claim 8, wherein the vial has contents consisting essentially of:
   (i) about 250 mg of the antibody;
   (ii) about 16.8 mg of L-histidine,
   (iii) about 2.2 mg of poloxamer PX188; and
   (iv) about 445.3 mg of sucrose.

10. A method of preparing the lyophilized dosage form of claim 8 for administration to a subject, comprising:
   (i) reconstituting the antibody formulation to a volume of about 5.0 mL with sterile water, and
   (ii) diluting the reconstituted antibody formulation of step (i) in normal saline for infusion.

11. A reconstituted formulation resulting from reconstituting the lyophilized formulation of claim 5.

12. The reconstituted formulation of claim 11, comprising the antibody at a concentration of about 50 mg/mL, the histidine buffer at a concentration of about 20 mM, poloxamer 188 (PX188) at a concentration of about 0.04% by weight, and at pH of about 6.0.

\* \* \* \* \*

UNITED STATES PATENT AND TRADEMARK OFFICE
CERTIFICATE OF CORRECTION

| | | |
|---|---|---|
| PATENT NO. | : 11,873,332 B2 | Page 1 of 1 |
| APPLICATION NO. | : 16/767994 | |
| DATED | : January 16, 2024 | |
| INVENTOR(S) | : Joseph Alexander Soto et al. | |

It is certified that error appears in the above-identified patent and that said Letters Patent is hereby corrected as shown below:

In the Claims

In Column 148, Line 40, Claim 4, delete "The formulation" and insert -- The pharmaceutical formulation --, therefor.

Signed and Sealed this
Twenty-third Day of July, 2024

Katherine Kelly Vidal
*Director of the United States Patent and Trademark Office*

```
                          SEQUENCE LISTING

<160> NUMBER OF SEQ ID NOS: 118

<210> SEQ ID NO 1
<211> LENGTH: 124
<212> TYPE: PRT
<213> ORGANISM: Artificial Sequence
<220> FEATURE:
<223> OTHER INFORMATION: m9D5VH

<400> SEQUENCE: 1

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Phe Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Thr Gly Thr Thr Val Thr Val Ser Ser
        115                 120

<210> SEQ ID NO 2
<211> LENGTH: 123
<212> TYPE: PRT
<213> ORGANISM: Artificial Sequence
<220> FEATURE:
<223> OTHER INFORMATION: 1SEQ_H

<400> SEQUENCE: 2

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Ala Arg Gln Thr Pro Glu Lys Lys Leu Glu Trp Val
        35                  40                  45

Ala Tyr Ile Ser Lys Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80
```

```
Leu Gln Met Ser Ser Leu Lys Ser Glu Asp Thr Ala Leu Tyr Tyr Cys
                85                  90                  95

Ala Arg Gly Ala Met Phe Gly Asn Asp Phe Lys Tyr Pro Met Asp Arg
            100                 105                 110

Trp Gly Gln Gly Thr Ser Val Thr Val Ser Ser
            115                 120

<210> SEQ ID NO 3
<211> LENGTH: 124
<212> TYPE: PRT
<213> ORGANISM: Artificial Sequence
<220> FEATURE:
<223> OTHER INFORMATION: BAC02114

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Thr Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gln Gly Ser Arg Tyr Tyr Tyr Tyr Gly Met Asp
            100                 105                 110

Val Trp Gly Gln Gly Thr Thr Val Thr Val Ser Ser
            115                 120

<210> SEQ ID NO 4
<211> LENGTH: 120
<212> TYPE: PRT
<213> ORGANISM: Artificial Sequence
<220> FEATURE:
<223> OTHER INFORMATION: AAX82494

<400> SEQUENCE: 4

Gln Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Tyr Tyr Gly Tyr Arg Tyr Tyr Phe Asp Tyr Trp Gly Gln
            100                 105                 110

Gly Thr Met Val Thr Val Ser Ser
            115                 120

<210> SEQ ID NO 5
```

```
<211> LENGTH: 124
<212> TYPE: PRT
<213> ORGANISM: Artificial Sequence
<220> FEATURE:
<223> OTHER INFORMATION: Hu9D5VHv1

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Phe Ser Arg Asp Asn Ala Lys Asn Ser Leu Tyr
65                  70                  75                  80

Leu Gln Ser Asn Ser Leu Lys Ala Glu Asp Thr Ala Val Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Thr Val Thr Val Ser Ser
        115                 120

<210> SEQ ID NO 6
<211> LENGTH: 124
<212> TYPE: PRT
<213> ORGANISM: Artificial Sequence
<220> FEATURE:
<223> OTHER INFORMATION: Hu9D5VHv2

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Phe Ser Arg Asp Asn Ala Lys Asn Ser Leu Tyr
65                  70                  75                  80

Leu Gln Ser Asn Leu Leu Arg Ala Glu Asp Thr Ala Val Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Thr Val Thr Val Ser Ser
        115                 120

<210> SEQ ID NO 7
<211> LENGTH: 124
<212> TYPE: PRT
<213> ORGANISM: Artificial Sequence
<220> FEATURE:
<223> OTHER INFORMATION: Hu9D5VHv2b

<400> SEQUENCE: 7

Glu Val Gln Leu Val Glu Ser Gly Gly Gly Leu Val Gln Pro Gly Gly
1               5                   10                  15
```

```
Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Leu Val Thr Val Ser Ser
        115                 120
```

<210> SEQ ID NO 8
<211> LENGTH: 124
<212> TYPE: PRT
<213> ORGANISM: Artificial Sequence
<220> FEATURE:
<223> OTHER INFORMATION: Hu9D5VHv3

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Glu Ile Ser Asn Ser Gly Asp Thr Thr Tyr Tyr Pro Asp Thr Val
    50                  55                  60

Lys Gly Arg Phe Thr Phe Ser Arg Asp Asn Ala Lys Asn Ser Leu Tyr
65                  70                  75                  80

Leu Gln Ser Asn Leu Leu Arg Ala Glu Asp Thr Ala Val Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Thr Val Thr Val Ser Ser
        115                 120
```

<210> SEQ ID NO 9
<211> LENGTH: 124
<212> TYPE: PRT
<213> ORGANISM: Artificial Sequence
<220> FEATURE:
<223> OTHER INFORMATION: Hu9D5VHv3b

<400> SEQUENCE: 9

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Gly Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80
```

```
Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Leu Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: Hu9D5VHv4

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Ser Asn Leu Leu Arg Ala Glu Asp Thr Ala Val Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Val Thr Val Ser Ser
        115                 120

<210> SEQ ID NO 11
<211> LENGTH: 124
<212> TYPE: PRT
<213> ORGANISM: Artificial Sequence
<220> FEATURE:
<223> OTHER INFORMATION: Hu9D5VHv4b

<400> SEQUENCE: 11

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Ala Pro Gly Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Leu Val Thr Val Ser Ser
        115                 120
```

```
<210> SEQ ID NO 12
<211> LENGTH: 124
<212> TYPE: PRT
<213> ORGANISM: Artificial Sequence
<220> FEATURE:
<223> OTHER INFORMATION: Hu9D5VHv5

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Leu Leu Arg Ala Glu Asp Thr Ala Val Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Thr Val Thr Val Ser Ser
        115                 120

<210> SEQ ID NO 13
<211> LENGTH: 5
<212> TYPE: PRT
<213> ORGANISM: Artificial Sequence
<220> FEATURE:
<223> OTHER INFORMATION: 9D5 CDRH1 - Kabat

<400> SEQUENCE: 13

Ser Tyr Thr Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: 9D5 CDRH2 - Kabat

<400> SEQUENCE: 14

Glu Ile Ser Asn Ser Gly Asp Thr Thr Tyr Tyr Pro Asp Thr Val Lys
1               5                   10                  15

Gly

<210> SEQ ID NO 15
<211> LENGTH: 15
<212> TYPE: PRT
<213> ORGANISM: Artificial Sequence
<220> FEATURE:
<223> OTHER INFORMATION: 9D5 CDRH3 - Kabat

<400> SEQUENCE: 15

His Tyr Tyr Tyr Gly Gly Gly Tyr Gly Gly Trp Phe Phe Asp Val
1               5                   10                  15

<210> SEQ ID NO 16
<211> LENGTH: 112
<212> TYPE: PRT
<213> ORGANISM: Artificial Sequence
```

<220> FEATURE:
<223> OTHER INFORMATION: m9D5VL

<400> SEQUENCE: 16

Asp Ile Val Met Thr Gln Ala Ala Pro Ser Val Pro Val Thr Pro Gly
1               5                   10                  15

Glu Ser Val Ser Ile Ser Cys Arg Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 17
<211> LENGTH: 112
<212> TYPE: PRT
<213> ORGANISM: Artificial Sequence
<220> FEATURE:
<223> OTHER INFORMATION: 1MJU_L

<400> SEQUENCE: 17

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Leu Gln His
                85                  90                  95

Leu Glu Tyr Pro Phe Thr Phe Gly Ala Gly Thr Lys Leu Glu Leu Lys
            100                 105                 110

<210> SEQ ID NO 18
<211> LENGTH: 112
<212> TYPE: PRT
<213> ORGANISM: Artificial Sequence
<220> FEATURE:
<223> OTHER INFORMATION: ABC66952

<400> SEQUENCE: 18

Asp Ile Val Met Thr Gln Ser Pro Leu Ser Leu Pro Val Thr Pro Gly
1               5                   10                  15

Glu Pro Ala Ser Ile Ser Cys Arg Ser Asn Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Ser Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ser Pro Tyr Thr Phe Gly Gln Gly Thr Lys Leu Glu Ile Lys
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: Hu9D5VLv1

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: Hu9D5VLv2

<400> SEQUENCE: 20

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: Hu9D5VLv3

```
<400> SEQUENCE: 21

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Hu9D5VLv4

<400> SEQUENCE: 22

Asp Ile Val Met Thr Gln Ser Ala Pro Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: Hu9D5VLv5

<400> SEQUENCE: 23

Asp Ile Val Met Thr Gln Ser Ala Pro Ser Leu Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Ala Phe Thr Leu Arg Ile
65                  70                  75                  80
```

```
Ser Arg Val Glu Ala Glu Asp Val Gly Val Tyr Tyr Cys Met Gln His
            85                  90                  95

Leu Glu Tyr Pro Leu Thr Phe Gly Gln Gly Thr Lys Leu Glu Ile Lys
        100                 105                 110

<210> SEQ ID NO 24
<211> LENGTH: 16
<212> TYPE: PRT
<213> ORGANISM: Artificial Sequence
<220> FEATURE:
<223> OTHER INFORMATION: 9D5 CDRL1 - Kabat

<400> SEQUENCE: 24

Arg Ser Ser Lys Ser Leu Leu His Ser Asn Gly Asn Thr Tyr Leu Tyr
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: 9D5 CDRL2 - Kabat

<400> SEQUENCE: 25

Arg Val Ser Asn Leu Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: 9D5 CDRL3 - Kabat

<400> SEQUENCE: 26

Met Gln His Leu Glu Tyr Pro Leu Thr
1               5

<210> SEQ ID NO 27
<211> LENGTH: 454
<212> TYPE: PRT
<213> ORGANISM: Artificial Sequence
<220> FEATURE:
<223> OTHER INFORMATION: Hu9D5 H1 heavy chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Phe Ser Arg Asp Asn Ala Lys Asn Ser Leu Tyr
65                  70                  75                  80

Leu Gln Ser Asn Ser Leu Lys Ala Glu Asp Thr Ala Val Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Gln Gly Thr Thr Val Thr Val Ser Ser Ala Ser Thr Lys
        115                 120                 125
```

```
Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 28
<211> LENGTH: 454
<212> TYPE: PRT
<213> ORGANISM: Artificial Sequence
<220> FEATURE:
<223> OTHER INFORMATION: Hu9D5 H2 heavy chain

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Thr Met Ser Trp Val Arg Gln Ala Pro Gly Lys Gly Leu Glu Leu Val
     35                  40                  45
Ala Glu Ile Ser Asn Ser Gly Asp Thr Thr Tyr Tyr Pro Asp Thr Val
 50                  55                  60
Lys Gly Arg Phe Thr Phe Ser Arg Asp Asn Ala Lys Asn Ser Leu Tyr
 65                  70                  75                  80
Leu Gln Ser Asn Leu Leu Arg Ala Glu Asp Thr Ala Val Tyr Tyr Cys
                 85                  90                  95
Ala Arg His Tyr Tyr Gly Gly Tyr Gly Gly Trp Phe Phe Asp
                100                 105                 110
Val Trp Gly Gln Gly Thr Thr Val Thr Val Ser Ser Ala Ser Thr Lys
                115                 120                 125
Gly Pro Ser Val Phe Pro Leu Ala Pro Ser Ser Lys Ser Thr Ser Gly
130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Gln Thr Tyr Ile Cys Asn
                195                 200                 205
Val Asn His Lys Pro Ser Asn Thr Lys Val Asp Lys Arg Val Glu Pro
                210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
                275                 280                 285
Val Glu Val His Asn Ala Lys Thr Lys Pro Arg Glu Glu Gln Tyr Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
                355                 360                 365
Gln Val Ser Leu Thr Cys Leu Val Lys Gly Phe Tyr Pro Ser Asp Ile
                370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
435                 440                 445
Ser Leu Ser Pro Gly Lys
```

450

<210> SEQ ID NO 29
<211> LENGTH: 454
<212> TYPE: PRT
<213> ORGANISM: Artificial Sequence
<220> FEATURE:
<223> OTHER INFORMATION: Hu9D5 H2b heavy chain

<400> SEQUENCE: 29

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn

```
                355                 360                 365
Gln Val Ser Leu Thr Cys Leu Val Lys Gly Phe Tyr Pro Ser Asp Ile
            370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
        450

<210> SEQ ID NO 30
<211> LENGTH: 454
<212> TYPE: PRT
<213> ORGANISM: Artificial Sequence
<220> FEATURE:
<223> OTHER INFORMATION: Hu9D5 H3 heavy chain

<400> SEQUENCE: 30

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Thr Met Ser Trp Val Arg Gln Ala Pro Gly Lys Gly Leu Glu Trp Val
        35                  40                  45
Ser Glu Ile Ser Asn Ser Gly Asp Thr Thr Tyr Tyr Pro Asp Thr Val
    50                  55                  60
Lys Gly Arg Phe Thr Phe Ser Arg Asp Asn Ala Lys Asn Ser Leu Tyr
65                  70                  75                  80
Leu Gln Ser Asn Leu Leu Arg Ala Glu Asp Thr Ala Val Tyr Tyr Cys
                85                  90                  95
Ala Arg His Tyr Tyr Tyr Gly Gly Gly Tyr Gly Gly Trp Phe Phe Asp
            100                 105                 110
Val Trp Gly Gln Gly Thr Thr Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Arg Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
```

```
                260               265               270
Val Ser His Glu Asp Pro Glu Val Lys Phe Asn Trp Tyr Val Asp Gly
        275               280               285
Val Glu Val His Asn Ala Lys Thr Lys Pro Arg Glu Glu Gln Tyr Asn
        290               295               300
Ser Thr Tyr Arg Val Val Ser Val Leu Thr Val Leu His Gln Asp Trp
305               310               315               320
Leu Asn Gly Lys Glu Tyr Lys Cys Lys Val Ser Asn Lys Ala Leu Pro
                325               330               335
Ala Pro Ile Glu Lys Thr Ile Ser Lys Ala Lys Gly Gln Pro Arg Glu
                340               345               350
Pro Gln Val Tyr Thr Leu Pro Pro Ser Arg Glu Glu Met Thr Lys Asn
        355               360               365
Gln Val Ser Leu Thr Cys Leu Val Lys Gly Phe Tyr Pro Ser Asp Ile
        370               375               380
Ala Val Glu Trp Glu Ser Asn Gly Gln Pro Glu Asn Asn Tyr Lys Thr
385               390               395               400
Thr Pro Pro Val Leu Asp Ser Asp Gly Ser Phe Phe Leu Tyr Ser Lys
                405               410               415
Leu Thr Val Asp Lys Ser Arg Trp Gln Gln Gly Asn Val Phe Ser Cys
                420               425               430
Ser Val Met His Glu Ala Leu His Asn His Tyr Thr Gln Lys Ser Leu
        435               440               445
Ser Leu Ser Pro Gly Lys
    450

<210> SEQ ID NO 31
<211> LENGTH: 454
<212> TYPE: PRT
<213> ORGANISM: Artificial Sequence
<220> FEATURE:
<223> OTHER INFORMATION: Hu9D5 H3b heavy chain

<400> SEQUENCE: 31

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Ser Ser Tyr
            20                  25                  30
Thr Met Ser Trp Val Arg Gln Thr Pro Gly Lys Arg Leu Glu Leu Val
        35                  40                  45
Ala Glu Ile Ser Asn Ser Gly Asp Thr Thr Tyr Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Ser Ser Leu Lys Ser Glu Asp Thr Ala Met Tyr Tyr Cys
                85                  90                  95
Ala Arg His Tyr Tyr Gly Gly Tyr Gly Trp Phe Asp
            100                 105                 110
Val Trp Gly Gln Gly Thr Leu Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
```

```
                    165                 170                 175

Phe Pro Ala Val Leu Gln Ser Ser Gly Leu Tyr Ser Leu Ser Ser Val
                180                 185                 190

Val Thr Val Pro Ser Ser Leu Gly Thr Gln Thr Tyr Ile Cys Asn
            195                 200                 205

Val Asn His Lys Pro Ser Asn Thr Lys Val Asp Lys Arg Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
        450

<210> SEQ ID NO 32
<211> LENGTH: 454
<212> TYPE: PRT
<213> ORGANISM: Artificial Sequence
<220> FEATURE:
<223> OTHER INFORMATION: Hu9D5 H4 heavy chain

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Ser Leu Tyr
```

```
            65                  70                  75                  80
Leu Gln Ser Asn Leu Leu Arg Ala Glu Asp Thr Ala Val Tyr Tyr Cys
                85                  90                  95

Ala Arg His Tyr Tyr Gly Gly Tyr Gly Gly Trp Phe Phe Asp
                100                 105                 110

Val Trp Gly Gln Gly Thr Thr Val Thr Val Ser Ser Ala Ser Thr Lys
                115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
            450

<210> SEQ ID NO 33
<211> LENGTH: 454
<212> TYPE: PRT
<213> ORGANISM: Artificial Sequence
```

<220> FEATURE:
<223> OTHER INFORMATION: Hu9D5 H4b heavy chain

<400> SEQUENCE: 33

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Ala Pro Gly Lys Arg Leu Glu Leu Val
        35                  40                  45

Ala Glu Ile Ser Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400
```

```
Thr Pro Pro Val Leu Asp Ser Asp Gly Ser Phe Phe Leu Tyr Ser Lys
            405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
            435                 440                 445
Ser Leu Ser Pro Gly Lys
    450

<210> SEQ ID NO 34
<211> LENGTH: 454
<212> TYPE: PRT
<213> ORGANISM: Artificial Sequence
<220> FEATURE:
<223> OTHER INFORMATION: Hu9D5 H5 heavy chain

<400> SEQUENCE: 34

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Thr Met Ser Trp Val Arg Gln Thr Pro Glu Lys Arg Leu Glu Leu Val
        35                  40                  45
Ala Glu Ile Ser Asn Ser Gly Asp Thr Thr Tyr Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Asn Leu Leu Arg Ala Glu Asp Thr Ala Val Tyr Tyr Cys
                85                  90                  95
Ala Arg His Tyr Tyr Gly Gly Gly Tyr Gly Gly Trp Phe Phe Asp
            100                 105                 110
Val Trp Gly Gln Gly Thr Thr Val Thr Val Ser Ser Ala Ser Thr Lys
    115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Arg Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
```

```
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Glu Glu Met Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys
    450

<210> SEQ ID NO 35
<211> LENGTH: 219
<212> TYPE: PRT
<213> ORGANISM: Artificial Sequence
<220> FEATURE:
<223> OTHER INFORMATION: Hu9D5 L1 light chain

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

Pro Val Thr Lys Ser Phe Asn Arg Gly Glu Cys
    210                 215

<210> SEQ ID NO 36
<211> LENGTH: 219
<212> TYPE: PRT
<213> ORGANISM: Artificial Sequence
<220> FEATURE:
<223> OTHER INFORMATION: Hu9D5 L2 light chain

<400> SEQUENCE: 36

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 37
<211> LENGTH: 219
<212> TYPE: PRT
<213> ORGANISM: Artificial Sequence
<220> FEATURE:
<223> OTHER INFORMATION: Hu9D5 L3 light chain

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Tyr Leu Gln Lys Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Met Gln His
                    85                  90                  95

Leu Glu Tyr Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
210                 215

<210> SEQ ID NO 38
<211> LENGTH: 219
<212> TYPE: PRT
<213> ORGANISM: Artificial Sequence
<220> FEATURE:
<223> OTHER INFORMATION: Hu9D5 L4 light chain

<400> SEQUENCE: 38

Asp Ile Val Met Thr Gln Ser Ala Pro Ser Leu Pro Val Thr Pro Gly
1               5                   10                  15

Glu Pro Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
        50                  55                  60

Ser Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                    85                  90                  95

Leu Glu Tyr Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
```

<210> SEQ ID NO 39
<211> LENGTH: 219
<212> TYPE: PRT
<213> ORGANISM: Artificial Sequence
<220> FEATURE:
<223> OTHER INFORMATION: Hu9D5 L5 light chain

<400> SEQUENCE: 39

Asp Ile Val Met Thr Gln Ser Ala Pro Ser Leu Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 40
<211> LENGTH: 429
<212> TYPE: DNA
<213> ORGANISM: Artificial Sequence
<220> FEATURE:
<223> OTHER INFORMATION: m9D5VH with signal peptide

<400> SEQUENCE: 40
atggactttg ggctcagctt gattttcctt gtccttgttt taaaaggtgt cctgtgtgaa    60
gtgaagctgg tggagtctgg gggaggttta gtgcagcctg agggtccct gaaactctcc    120 tgtgcagcct ctggattcac tttcagtagc tataccatgt cttgggttcg ccagactcca    180 gaaagaggc tggagttggt cgcagaaatt agtaatagtg gtgataccac ctactatcca    240
gacactgtaa agggccgatt caccttctcc agagacaatg ccaagaacac cctgtacctg    300
caaatgagca gtctgaagtc tgaggacacg gccatgtatt actgtgcaag acattattac    360
tatggtggtg gctacggggg gtggttcttc gatgtctggg gcacagggac cacggtcacc    420
gtctcctcg                                                            429

<210> SEQ ID NO 41
<211> LENGTH: 143
<212> TYPE: PRT
<213> ORGANISM: Artificial Sequence
<220> FEATURE:
<223> OTHER INFORMATION: m9D5VH with signal peptide

<400> SEQUENCE: 41

Met Asp Phe Gly Leu Ser Leu Ile Phe Leu Val Leu Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Leu Val Ala Glu Ile Ser Asn Ser Gly Asp Thr Thr Tyr Tyr Pro
65                  70                  75                  80

Asp Thr Val Lys Gly Arg Phe Thr Phe Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Tyr Tyr Gly Gly Tyr Gly Gly Trp
        115                 120                 125

Phe Phe Asp Val Trp Gly Thr Gly Thr Thr Val Thr Val Ser Ser
    130                 135                 140

<210> SEQ ID NO 42
<211> LENGTH: 396
<212> TYPE: DNA
<213> ORGANISM: Artificial Sequence
<220> FEATURE:
<223> OTHER INFORMATION: m9D5VL with signal peptide

<400> SEQUENCE: 42
atgaggtgcc tagctgagtt cctggggctg cttgtgctct ggatccctgg agccattggg      60
gatattgtga tgactcaggc tgcacccctct gtacctgtca ctcctggaga gtcagtatcc     120
atctcctgca ggtctagtaa gagtctcctg catagtaatg caacacttta cttgtattgg     180
ttcctgcaga ggccaggcca gtctcctcaa ctcctgatat atcgggtgtc caaccttgcc     240
tcaggagtcc cagacaggtt cagtggcagt gggtcaggaa ctgctttcac actgagaatc     300
agtagagtgg aggctgagga tgtgggtgtt tattactgta tgcaacattt agaatatccg     360
ctcacgttcg gtgctgggac caagctggag ctgaaa                              396

<210> SEQ ID NO 43
<211> LENGTH: 132
<212> TYPE: PRT
<213> ORGANISM: Artificial Sequence
<220> FEATURE:
<223> OTHER INFORMATION: m9D5VL with signal peptide

<400> SEQUENCE: 43

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Ser Lys Ser

```
                    35                  40                  45
Leu Leu His Ser Asn Gly Asn Thr Tyr Leu Tyr Trp Phe Leu Gln Arg
         50                  55                  60

Pro Gly Gln Ser Pro Gln Leu Leu Ile Tyr Arg Val Ser Asn Leu Ala
 65                  70                  75                  80

Ser Gly Val Pro Asp Arg Phe Ser Gly Ser Gly Ser Gly Thr Ala Phe
                     85                  90                  95

Thr Leu Arg Ile Ser Arg Val Glu Ala Glu Asp Val Gly Val Tyr Tyr
                100                 105                 110

Cys Met Gln His Leu Glu Tyr Pro Leu Thr Phe Gly Ala Gly Thr Lys
            115                 120                 125

Leu Glu Leu Lys
      130

<210> SEQ ID NO 44
<211> LENGTH: 372
<212> TYPE: DNA
<213> ORGANISM: Artificial Sequence
<220> FEATURE:
<223> OTHER INFORMATION: Hu9D5VHv1

<400> SEQUENCE: 44
gaggtgcagc tggtggagtc cggcggcggc ctggtgcagc ccggcggctc cctgcgcctg      60
tcctgcgccg cctccggctt caccttctcc tcctacacca tgtcctgggt gcgccaggcc     120
cccggcaagg gcctggagct ggtggccgag atctccaact ccggcgacac cacctactac     180
cccgacaccg tgaagggccg cttcaccttc tcccgcgaca cgccaagaa ctccctgtac     240 ctgcagtcca actccctgaa ggccgaggac accgccgtgt actactgcgc cgccactac     300 tactacggcg gcggctacgg cggctggttc ttcgacgtgt ggggccaggg caccaccgtg     360
accgtgtcct ca                                                         372

<210> SEQ ID NO 45
<211> LENGTH: 372
<212> TYPE: DNA
<213> ORGANISM: Artificial Sequence
<220> FEATURE:
<223> OTHER INFORMATION: Hu9D5VHv2

<400> SEQUENCE: 45
gaggtgcagc tggtggagtc cggcggcggc ctggtgcagc ccggcggctc cctgcgcctg      60
tcctgcgccg cctccggctt caccttctcc tcctacacca tgtcctgggt gcgccaggcc     120
cccggcaagg gcctggagct ggtggccgag atctccaact ccggcgacac cacctactac     180
cccgacaccg tgaagggccg cttcaccttc tcccgcgaca cgccaagaa ctccctgtac     240 ctgcagtcca actgctgcg cgccgaggac accgccgtgt actactgcgc cgccactac     300 tactacggcg gcggctacgg cggctggttc ttcgacgtgt ggggccaggg caccaccgtg     360
accgtgtcct ca                                                         372

<210> SEQ ID NO 46
<211> LENGTH: 372
<212> TYPE: DNA
<213> ORGANISM: Artificial Sequence
<220> FEATURE:
<223> OTHER INFORMATION: Hu9D5VHv2b

<400> SEQUENCE: 46
gaggtgcaac tggtggagtc tggcggcggc ttggtgcaac ctggcggctc cctgaagctg      60
```

```
tcctgtgccg cctccggctt caccttcagc agctatacca tgtcttgggt gcgccaaacc    120
cccgagaaga ggctggagtt ggtggctgag attagtaata gcggcgatac cacctactat    180
cccgataccg tgaagggccg cttcaccatt ccagagata  atgctaagaa taccctgtat    240
ctgcaaatga gtagcctgaa gtctgaggat accgctatgt attattgtgc tagacattat    300
tattatggcg gcggctatgg cggctggttc ttcgatgtgt ggggccaagg caccctggtc    360
accgtgtcct ca                                                        372

<210> SEQ ID NO 47
<211> LENGTH: 372
<212> TYPE: DNA
<213> ORGANISM: Artificial Sequence
<220> FEATURE:
<223> OTHER INFORMATION: Hu9D5VHv3

<400> SEQUENCE: 47
gaggtgcagc tggtggagtc cggcggcggc ctggtgcagc ccggcggctc cctgcgcctg     60
tcctgcgccg cctccggctt caccttctcc tcctacacca tgtcctgggt gcgccaggcc    120
cccggcaagg gctggagtg  ggtgtccgag atctccaact ccggcgacac cacctactac    180
cccgacaccg tgaagggccg cttcaccttc tcccgcgaca cgccaagaa  ctccctgtac    240 ctgcagtcca acctgctgcg cgccgaggac accgccgtgt actactgcgc cgccactac    300 tactacggcg gcggctacgg cggctggttc ttcgacgtgt ggggccaggg caccaccgtg    360
accgtgtcct ca                                                        372

<210> SEQ ID NO 48
<211> LENGTH: 372
<212> TYPE: DNA
<213> ORGANISM: Artificial Sequence
<220> FEATURE:
<223> OTHER INFORMATION: Hu9D5VHv3b

<400> SEQUENCE: 48
gaggtgcaac tggtggagtc tggcggcggc ttggtgcaac ctggcggctc cctgaagctg     60
tcctgtgccg cctccggctt caccttcagc agctatacca tgtcttgggt gcgccaaacc    120
cccgggaaga ggctggagtt ggtggctgag attagtaata gcggcgatac cacctactat    180
cccgataccg tgaagggccg cttcaccatt ccagagata  atgctaagaa taccctgtat    240
ctgcaaatga gtagcctgaa gtctgaggat accgctatgt attattgtgc tagacattat    300
tattatggcg gcggctatgg cggctggttc ttcgatgtgt ggggccaagg caccctggtc    360
accgtgtcct ca                                                        372

<210> SEQ ID NO 49
<211> LENGTH: 372
<212> TYPE: DNA
<213> ORGANISM: Artificial Sequence
<220> FEATURE:
<223> OTHER INFORMATION: Hu9D5VHv4

<400> SEQUENCE: 49
gaggtgcagc tggtggagtc cggcggcggc ctggtgcagc ccggcggctc cctgcgcctg     60
tcctgcgccg cctccggctt caccttctcc tcctacacca tgtcctgggt gcgccaggcc    120
cccggcaagg gctggagtg  ggtgtccgag atctccaact ccggcgacac cacctactac    180
cccgacaccg tgaagggccg cttcaccatc tcccgcgaca cgccaagaa  ctccctgtac    240
```

```
ctgcagtcca acctgctgcg cgccgaggac accgccgtgt actactgcgc ccgccactac      300
tactacggcg gcggctacgg cggctggttc ttcgacgtgt ggggccaggg caccaccgtg      360
accgtgtcct ca                                                          372

<210> SEQ ID NO 50
<211> LENGTH: 372
<212> TYPE: DNA
<213> ORGANISM: Artificial Sequence
<220> FEATURE:
<223> OTHER INFORMATION: Hu9D5VHv4b

<400> SEQUENCE: 50
gaggtgcaac tggtggagtc tggcggcggc ttggtgcaac ctggcggctc cctgaagctg       60
tcctgtgccg cctccggctt caccttcagc agctatacca tgtcttgggt gcgccaagcc      120
cccgggaaga ggctggagtt ggtggctgag attagtaata gcggcgatac cacctactat      180
cccgataccg tgaagggccg cttcaccatt tccagagata tgctaagaa taccctgtat      240 ctgcaaatga gtagcctgaa gtctgaggat accgctatgt attattgtgc tagacattat      300
tattatggcg gcggctatgg cggctggttc ttcgatgtgt ggggccaagg caccctggtc      360
accgtgtcct ca                                                          372

<210> SEQ ID NO 51
<211> LENGTH: 372
<212> TYPE: DNA
<213> ORGANISM: Artificial Sequence
<220> FEATURE:
<223> OTHER INFORMATION: Hu9D5VHv5

<400> SEQUENCE: 51
gaggtgcagc tggtggagtc cggcggcggc ctggtgcagc ccggcggctc cctgcgcctg       60
tcctgcgccg cctccggctt caccttctcc tcctacacca tgtcctgggt cgccagacc      120 cccgagaagc gcctggagct ggtggccgag atctccaact ccggcgacac cacctactac      180
cccgacaccg tgaagggccg cttcaccatc tcccgcgaca cgccaagaa caccctgtac      240 ctgcagatga acctgctgcg cgccgaggac accgccgtgt actactgcgc ccgccactac      300
tactacggcg gcggctacgg cggctggttc ttcgacgtgt ggggccaagg caccaccgtg      360
accgtgtcct ca                                                          372

<210> SEQ ID NO 52
<211> LENGTH: 336
<212> TYPE: DNA
<213> ORGANISM: Artificial Sequence
<220> FEATURE:
<223> OTHER INFORMATION: Hu9D5VLv1

<400> SEQUENCE: 52
gacatcgtga tgacccagtc ccccctgtcc ctgcccgtga cccccggcga gcccgcctcc       60
atctcctgcc gctcctccaa gtccctgctg cactccaacg gcaacaccta cctgtactgg      120
ttcctgcaga agcccggcca gtcccccag ctgctgatct accgcgtgtc caacctggcc      180
tccggcgtgc ccgaccgctt ctccggctcc ggctccggca ccgacttcac cctgaagatc      240
tcccgcgtgg aggccgagga cgtgggcgtg tactactgca tgcagcacct ggagtacccc      300
ctgaccttcg gccagggcac caagctggag atcaaa                               336

<210> SEQ ID NO 53
<211> LENGTH: 336
```

```
<212> TYPE: DNA
<213> ORGANISM: Artificial Sequence
<220> FEATURE:
<223> OTHER INFORMATION: Hu9D5VLv2

<400> SEQUENCE: 53
gacatcgtga tgacccagtc cccctgtcc ctgcccgtga ccccggcga gcccgcctcc    60 atctcctgcc gctcctccaa gtccctgctg cactccaacg gcaacaccta cctgtactgg   120
tacctgcaga agcccggcca gtccccccag ctgctgatct accgcgtgtc caacctggcc   180
tccggcgtgc ccgaccgctt ctccggctcc ggctccggca ccgacttcac cctgaagatc   240
tcccgcgtgg aggccgagga cgtgggcgtg tactactgca tgcagcacct ggagtacccc   300
ctgaccttcg gccagggcac caagctggag atcaaa                              336

<210> SEQ ID NO 54
<211> LENGTH: 336
<212> TYPE: DNA
<213> ORGANISM: Artificial Sequence
<220> FEATURE:
<223> OTHER INFORMATION: Hu9D5VLv3

<400> SEQUENCE: 54
gacatcgtga tgacccagtc cccctgtcc ctgcccgtga ccccggcga gcccgcctcc    60 atctcctgcc gctcctccaa gtccctgctg cactccaacg gcaacaccta cctgtactgg   120
tacctgcaga agcccggcca gtccccccag ctgctgatct accgcgtgtc caacctggcc   180
tccggcgtgc cctcccgctt ctccggctcc ggctccggca ccgacttcac cctgaagatc   240
tcccgcgtgg aggccgagga cgtgggcgtg tactactgca tgcagcacct ggagtacccc   300
ctgaccttcg gccagggcac caagctggag atcaaa                              336

<210> SEQ ID NO 55
<211> LENGTH: 336
<212> TYPE: DNA
<213> ORGANISM: Artificial Sequence
<220> FEATURE:
<223> OTHER INFORMATION: Hu9D5VLv4

<400> SEQUENCE: 55
gacatcgtga tgacccagtc cgcccctcc ctgcccgtga ccccggcga gcccgtgtcc    60 atctcctgcc gctcctccaa gtccctgctg cactccaacg gcaacaccta cctgtactgg   120
ttcctgcagc gccccggcca gtccccccag ctgctgatct accgcgtgtc caacctggcc   180
tccggcgtgc cctcccgctt ctccggctcc ggctccggca ccgccttcac cctgcgcatc   240
tcccgcgtgg aggccgagga cgtgggcgtg tactactgca tgcagcacct ggagtacccc   300
ctgaccttcg gccaaggcac caagctggag atcaaa                              336

<210> SEQ ID NO 56
<211> LENGTH: 336
<212> TYPE: DNA
<213> ORGANISM: Artificial Sequence
<220> FEATURE:
<223> OTHER INFORMATION: Hu9D5VLv5

<400> SEQUENCE: 56
gacatcgtga tgacccagtc cgcccctcc ctgcccgtga ccccggcga gtccgtgtcc    60 atctcctgcc gctcctccaa gtccctgctg cactccaacg gcaacaccta cctgtactgg   120
ttcctgcagc gccccggcca gtccccccag ctgctgatct accgcgtgtc caacctggcc   180
```

```
tccggcgtgc cctcccgctt ctccggctcc ggctccggca ccgccttcac cctgcgcatc    240
tcccgcgtgg aggccgagga cgtgggcgtg tactactgca tgcagcacct ggagtacccc    300
ctgaccttcg gccaaggcac caagctggag atcaaa                              336
```

<210> SEQ ID NO 57
<211> LENGTH: 19
<212> TYPE: PRT
<213> ORGANISM: Artificial Sequence
<220> FEATURE:
<223> OTHER INFORMATION: 9D5VH Signal Peptide

<400> SEQUENCE: 57

Met Asp Phe Gly Leu Ser Leu Ile Phe Leu Val Leu Val Leu Lys Gly
1               5                   10                  15

Val Leu Cys

<210> SEQ ID NO 58
<211> LENGTH: 57
<212> TYPE: DNA
<213> ORGANISM: Artificial Sequence
<220> FEATURE:
<223> OTHER INFORMATION: 9D5VH Signal Peptide

<400> SEQUENCE: 58

```
atggactttg ggctcagctt gattttcctt gtccttgttt aaaaggtgt cctgtgt      57
```

<210> SEQ ID NO 59
<211> LENGTH: 20
<212> TYPE: PRT
<213> ORGANISM: Artificial Sequence
<220> FEATURE:
<223> OTHER INFORMATION: 9D5VL Signal Peptide

<400> SEQUENCE: 59

Met Arg Cys Leu Ala Glu Phe Leu Gly Leu Leu Val Leu Trp Ile Pro
1               5                   10                  15

Gly Ala Ile Gly
            20

<210> SEQ ID NO 60
<211> LENGTH: 60
<212> TYPE: DNA
<213> ORGANISM: Artificial Sequence
<220> FEATURE:
<223> OTHER INFORMATION: 9D5VL Signal Peptide

<400> SEQUENCE: 60

```
atgaggtgcc tagctgagtt cctggggctg cttgtgctct ggatccctgg agccattggg    60
```

<210> SEQ ID NO 61
<211> LENGTH: 124
<212> TYPE: PRT
<213> ORGANISM: Artificial Sequence
<220> FEATURE:
<223> OTHER INFORMATION: m14G8VH

<400> SEQUENCE: 61

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

```
Ala Glu Ile Asn Asn Ser Gly Asp Thr Thr Tyr Tyr Pro Asp Thr Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Tyr Tyr Tyr Gly Gly Tyr Gly Gly Trp Phe Phe Asp
             100                 105                 110

Val Trp Gly Thr Gly Thr Thr Val Thr Val Ser Ser
             115                 120
```

<210> SEQ ID NO 62
<211> LENGTH: 118
<212> TYPE: PRT
<213> ORGANISM: Artificial Sequence
<220> FEATURE:
<223> OTHER INFORMATION: 1MQK_H

<400> SEQUENCE: 62

```
Glu Val Lys Leu Gln Glu Ser Gly Gly Asp Leu Val Gln Pro Gly Gly
 1               5                  10                  15

Ser Leu Lys Leu Ser Cys Ala Ala Ser Gly Phe Thr Phe Ser Ser Tyr
                 20                  25                  30

Thr Met Ser Trp Val Arg Gln Thr Pro Glu Lys Arg Leu Glu Trp Val
             35                  40                  45

Ala Ser Ile Asn Asn Gly Gly Gly Arg Thr Tyr Tyr Pro Asp Thr Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Val Arg His Glu Tyr Tyr Tyr Ala Met Asp Tyr Trp Gly Gln Gly Thr
             100                 105                 110

Thr Val Thr Val Ser Ser
             115
```

<210> SEQ ID NO 63
<211> LENGTH: 124
<212> TYPE: PRT
<213> ORGANISM: Artificial Sequence
<220> FEATURE:
<223> OTHER INFORMATION: AAD30410

<400> SEQUENCE: 63

```
Gln Val Gln Leu Val Gln Ser Gly Gly Gly Leu Val Gln Pro Gly Gly
 1               5                  10                  15

Ser Arg Lys Leu Ser Cys Ala Ala Ser Gly Phe Thr Phe Ser Ser Tyr
                 20                  25                  30

Ala Met Ser Trp Val Arg Gln Thr Pro Glu Lys Arg Leu Glu Trp Val
             35                  40                  45

Ala Ala Ile Ser Thr Asp Gly Ser Phe Ile Tyr Tyr Ala Asp Thr Val
         50                  55                  60

Lys Gly Arg Phe Thr Ile Ser Gly Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Gly Ile Asp Ala Thr Ala Gln Val Gly Arg Phe Asp
```

```
                    100                 105                 110
Pro Trp Gly Gln Gly Thr Leu Val Thr Val Ser Ser
            115                 120

<210> SEQ ID NO 64
<211> LENGTH: 124
<212> TYPE: PRT
<213> ORGANISM: Artificial Sequence
<220> FEATURE:
<223> OTHER INFORMATION: Hu14G8VHv1

<400> SEQUENCE: 64

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Tyr Gly Gly Trp Phe Phe Asp
            100                 105                 110

Val Trp Gly Thr Gly Thr Leu Val Thr Val Ser Ser
            115                 120

<210> SEQ ID NO 65
<211> LENGTH: 124
<212> TYPE: PRT
<213> ORGANISM: Artificial Sequence
<220> FEATURE:
<223> OTHER INFORMATION: Hu14G8VHv2

<400> SEQUENCE: 65

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser
            115                 120

<210> SEQ ID NO 66
<211> LENGTH: 124
<212> TYPE: PRT
<213> ORGANISM: Artificial Sequence
<220> FEATURE:
```

<223> OTHER INFORMATION: Hu14G8VHv3

<400> SEQUENCE: 66

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg His Tyr Tyr Tyr Gly Gly Tyr Gly Gly Trp Phe Phe Asp
            100                 105                 110

Val Trp Gly Gln Gly Thr Leu Val Thr Val Ser Ser
        115                 120

<210> SEQ ID NO 67
<211> LENGTH: 5
<212> TYPE: PRT
<213> ORGANISM: Artificial Sequence
<220> FEATURE:
<223> OTHER INFORMATION: 14G8 CDRH1 - Kabat

<400> SEQUENCE: 67

Ser Tyr Thr Met Ser
1               5

<210> SEQ ID NO 68
<211> LENGTH: 17
<212> TYPE: PRT
<213> ORGANISM: Artificial Sequence
<220> FEATURE:
<223> OTHER INFORMATION: 14G8 CDRH2 - Kabat

<400> SEQUENCE: 68

Glu Ile Asn Asn Ser Gly Asp Thr Thr Tyr Tyr Pro Asp Thr Val Lys
1               5                   10                  15

Gly

<210> SEQ ID NO 69
<211> LENGTH: 15
<212> TYPE: PRT
<213> ORGANISM: Artificial Sequence
<220> FEATURE:
<223> OTHER INFORMATION: 14G8 CDRH3 - Kabat

<400> SEQUENCE: 69

His Tyr Tyr Tyr Gly Gly Tyr Gly Gly Trp Phe Phe Asp Val
1               5                   10              15

<210> SEQ ID NO 70
<211> LENGTH: 113
<212> TYPE: PRT
<213> ORGANISM: Artificial Sequence
<220> FEATURE:
<223> OTHER INFORMATION: m14G8VL

<400> SEQUENCE: 70

```
Asp Ile Val Met Thr Gln Ala Ala Pro Ser Val Pro Val Thr Pro Gly
1               5                   10                  15

Glu Ser Val Ser Ile Ser Cys Arg Ser Asn Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
            85                  90                  95

Leu Glu Tyr Pro Leu Thr Phe Gly Ala Gly Thr Lys Leu Glu Leu Lys
            100                 105                 110

Arg
```

<210> SEQ ID NO 71
<211> LENGTH: 113
<212> TYPE: PRT
<213> ORGANISM: Artificial Sequence
<220> FEATURE:
<223> OTHER INFORMATION: MJU_L

<400> SEQUENCE: 71

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Leu Gln His
            85                  90                  95

Leu Glu Tyr Pro Phe Thr Phe Gly Ala Gly Thr Lys Leu Glu Leu Lys
            100                 105                 110

Arg
```

<210> SEQ ID NO 72
<211> LENGTH: 113
<212> TYPE: PRT
<213> ORGANISM: Artificial Sequence
<220> FEATURE:
<223> OTHER INFORMATION: ABA71374

<400> SEQUENCE: 72

```
Asp Ile Val Met Thr Gln Thr Pro Leu Ser Leu Pro Val Thr Pro Gly
1               5                   10                  15

Glu Ser Ala Ser Ile Ser Cys Arg Ser Ser Gln Ser Leu Arg His Tyr
            20                  25                  30

Ser Gly Tyr Thr Tyr Ile Asp Trp Tyr Leu Gln Lys Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
```

```
            65                  70                  75                  80
Ser Arg Val Glu Ala Glu Asp Val Gly Val Tyr Tyr Cys Met Gln Ala
                    85                  90                  95

Leu Gln Thr Val Cys Ser Phe Gly Gln Gly Thr Lys Leu Glu Ile Lys
                100                 105                 110

Arg

<210> SEQ ID NO 73
<211> LENGTH: 113
<212> TYPE: PRT
<213> ORGANISM: Artificial Sequence
<220> FEATURE:
<223> OTHER INFORMATION: ABC66952.1

<400> SEQUENCE: 73

Asp Ile Val Met Thr Gln Ser Pro Leu Ser Leu Pro Val Thr Pro Gly
1               5                   10                  15

Glu Pro Ala Ser Ile Ser Cys Arg Ser Asn Gln Ser Leu Leu Tyr Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Ser Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                    85                  90                  95

Leu Gln Ser Pro Tyr Thr Phe Gly Gln Gly Thr Lys Leu Glu Ile Lys
                100                 105                 110

Arg

<210> SEQ ID NO 74
<211> LENGTH: 113
<212> TYPE: PRT
<213> ORGANISM: Artificial Sequence
<220> FEATURE:
<223> OTHER INFORMATION: Hu14G8VLv1

<400> SEQUENCE: 74

Asp Ile Val Met Thr Gln Ser Ala Pro Ser Leu Pro Val Thr Pro Gly
1               5                   10                  15

Glu Ser Val Ser Ile Ser Cys Arg Ser Asn Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                    85                  90                  95

Leu Glu Tyr Pro Leu Thr Phe Gly Gln Gly Thr Lys Leu Glu Ile Lys
                100                 105                 110

Arg

<210> SEQ ID NO 75
<211> LENGTH: 113
```

<212> TYPE: PRT
<213> ORGANISM: Artificial Sequence
<220> FEATURE:
<223> OTHER INFORMATION: Hu14G8VLv2

<400> SEQUENCE: 75

Asp Ile Val Met Thr Gln Ser Pro Leu Ser Leu Pro Val Thr Pro Gly
1               5                   10                  15

Glu Pro Ala Ser Ile Ser Cys Arg Ser Asn Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg

<210> SEQ ID NO 76
<211> LENGTH: 113
<212> TYPE: PRT
<213> ORGANISM: Artificial Sequence
<220> FEATURE:
<223> OTHER INFORMATION: Hu14G8VLv3

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Ser Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg

<210> SEQ ID NO 77
<211> LENGTH: 16
<212> TYPE: PRT
<213> ORGANISM: Artificial Sequence
<220> FEATURE:
<223> OTHER INFORMATION: 14G8 CDRL1 (mouse, HuVLv1, HuVLv2) - Kabat

<400> SEQUENCE: 77

Arg Ser Asn Lys Ser Leu Leu His Ser Asn Gly Asn Thr Tyr Leu Tyr
1               5                   10                  15

<210> SEQ ID NO 78
<211> LENGTH: 7

<210> SEQ ID NO 78
<211> LENGTH: 6 (implied)
<212> TYPE: PRT
<213> ORGANISM: Artificial Sequence
<220> FEATURE:
<223> OTHER INFORMATION: 14G8 CDRL2 - Kabat

<400> SEQUENCE: 78

Arg Val Ser Asn Leu Ala Ser
1               5

<210> SEQ ID NO 79
<211> LENGTH: 9
<212> TYPE: PRT
<213> ORGANISM: Artificial Sequence
<220> FEATURE:
<223> OTHER INFORMATION: 14G8 CDRL3 - Kabat

<400> SEQUENCE: 79

Met Gln His Leu Glu Tyr Pro Leu Thr
1               5

<210> SEQ ID NO 80
<211> LENGTH: 16
<212> TYPE: PRT
<213> ORGANISM: Artificial Sequence
<220> FEATURE:
<223> OTHER INFORMATION: 14G8 CDRL1 (HuVLv3) - Kabat

<400> SEQUENCE: 80

Arg Ser Ser Lys Ser Leu Leu His Ser Asn Gly Asn Thr Tyr Leu Tyr
1               5                   10                  15

<210> SEQ ID NO 81
<211> LENGTH: 454
<212> TYPE: PRT
<213> ORGANISM: Artificial Sequence
<220> FEATURE:
<223> OTHER INFORMATION: Hu14G8 H1 heavy chain

<400> SEQUENCE: 81

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Leu Val
            35                  40                  45

Ala Glu Ile Asn Asn Ser Gly Asp Thr Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
                100                 105                 110

Val Trp Gly Thr Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

```
Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 82
<211> LENGTH: 454
<212> TYPE: PRT
<213> ORGANISM: Artificial Sequence
<220> FEATURE:
<223> OTHER INFORMATION: Hu14G8 H2 heavy chain

<400> SEQUENCE: 82

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80
```

```
Leu Gln Met Ser Ser Leu Lys Ser Glu Asp Thr Ala Met Tyr Tyr Cys
                 85                  90                  95

Ala Arg His Tyr Tyr Gly Gly Tyr Gly Gly Trp Phe Phe Asp
            100                 105                 110

Val Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 83
<211> LENGTH: 454
<212> TYPE: PRT
<213> ORGANISM: Artificial Sequence
<220> FEATURE:
<223> OTHER INFORMATION: Hu14G8 H3 heavy chain
```

<400> SEQUENCE: 83

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Leu Val
        35                  40                  45

Ala Glu Ile Asn Asn Ser Gly Asp Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Tyr Tyr Gly Gly Tyr Gly Gly Trp Phe Phe Asp
            100                 105                 110

Val Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 84
<211> LENGTH: 219
<212> TYPE: PRT
<213> ORGANISM: Artificial Sequence
<220> FEATURE:
<223> OTHER INFORMATION: Hu14G8 L1 light chain

<400> SEQUENCE: 84

Asp Ile Val Met Thr Gln Ser Ala Pro Ser Leu Pro Val Thr Pro Gly
1               5                   10                  15

Glu Ser Val Ser Ile Ser Cys Arg Ser Asn Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Leu Leu Ile Tyr Arg Val Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 85
<211> LENGTH: 219
<212> TYPE: PRT
<213> ORGANISM: Artificial Sequence
<220> FEATURE:
<223> OTHER INFORMATION: Hu14G8 L2 light chain

<400> SEQUENCE: 85

Asp Ile Val Met Thr Gln Ser Pro Leu Ser Leu Pro Val Thr Pro Gly
1               5                   10                  15

Glu Pro Ala Ser Ile Ser Cys Arg Ser Asn Lys Ser Leu Leu His Ser
            20                  25                  30

```
Asn Gly Asn Thr Tyr Leu Tyr Trp Phe Leu Gln Lys Pro Gly Gln Ser
            35                  40                  45

Pro Gln Leu Leu Ile Tyr Arg Val Ser Asn Leu Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
               100                 105                 110

Arg Thr Val Ala Ala Pro Ser Val Phe Ile Phe Pro Pro Ser Asp Glu
           115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
       195                 200                 205

Pro Val Thr Lys Ser Phe Asn Arg Gly Glu Cys
           210                 215

<210> SEQ ID NO 86
<211> LENGTH: 219
<212> TYPE: PRT
<213> ORGANISM: Artificial Sequence
<220> FEATURE:
<223> OTHER INFORMATION: Hu14G8 L3 light chain

<400> SEQUENCE: 86

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
            35                  40                  45

Pro Gln Leu Leu Ile Tyr Arg Val Ser Asn Leu Ala Ser Gly Val Pro
 50                  55                  60

Ser Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Gln Gly Thr Lys Leu Glu Ile Lys
               100                 105                 110

Arg Thr Val Ala Ala Pro Ser Val Phe Ile Phe Pro Pro Ser Asp Glu
           115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 87
<211> LENGTH: 429
<212> TYPE: DNA
<213> ORGANISM: Artificial Sequence
<220> FEATURE:
<223> OTHER INFORMATION: m14G8VH with signal peptide

<400> SEQUENCE: 87
atgaatttcg ggctcagctt gattttcctt gtccttgttt taaaaggtgt cctgtgtgaa      60
gtgaagctgg tggagtctgg gggaggttta gtgcagcctg agggtccct gaaactctcc      120 tgtgcagcct ccggattcac tttcagtagc tataccatgt cttgggttcg ccagactcca     180
gaaaagaggc tggagttggt cgcagaaatt aataatagtg gtgataccac ctactatcca     240
gacactgtaa agggccgatt caccatctcc agagacaatg ccaagaacac cctgtacctg     300
caaatgagca gtctgaagtc tgaggacacg gccatgtatt actgtgcaag acattattac     360
tatggtggtg gctacggggg gtggttcttc gatgtctggg gcacagggac cacggtcacc     420
gtctcctca                                                            429

<210> SEQ ID NO 88
<211> LENGTH: 143
<212> TYPE: PRT
<213> ORGANISM: Artificial Sequence
<220> FEATURE:
<223> OTHER INFORMATION: m14G8VH with signal peptide

<400> SEQUENCE: 88

Met Asn Phe Gly Leu Ser Leu Ile Phe Leu Val Leu Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Thr Met Ser Trp Val Arg Gln Thr Pro Glu Lys Arg Leu
    50                  55                  60

Glu Leu Val Ala Glu Ile Asn Asn Ser Gly Asp Thr Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg His Tyr Tyr Gly Gly Gly Tyr Gly Gly Trp
        115                 120                 125

Phe Phe Asp Val Trp Gly Thr Gly Thr Thr Val Thr Val Ser Ser
    130                 135                 140

<210> SEQ ID NO 89
<211> LENGTH: 399
<212> TYPE: DNA
<213> ORGANISM: Artificial Sequence
<220> FEATURE:
<223> OTHER INFORMATION: m14G8VL with signal peptide

```
<400> SEQUENCE: 89
atgaggtgcc tagctgagtt cctggggctg cttgtgctct ggatccctgg agccattggg    60
gatattgtga tgactcaggc tgcaccctct gtacctgtca ctcctggaga gtcagtatcc   120
atctcctgca ggtctaataa gagtctcctg catagtaatg caacactta cttgtattgg   180 ttcctgcaga ggccaggcca gtctcctcaa ctcctgatat atcgggtgtc caaccttgcc   240
tcaggagtcc cagacaggtt cagtggcagt gggtcaggaa ctgctttcac actgagaatc   300
agtagagtgg aggctgagga tgtgggtgtt tattactgta tgcaacattt agaatatccg   360
ctcacgttcg gtgctgggac caagctggag ctgaaacgt                          399

<210> SEQ ID NO 90
<211> LENGTH: 133
<212> TYPE: PRT
<213> ORGANISM: Artificial Sequence
<220> FEATURE:
<223> OTHER INFORMATION: m14G8VL with signal peptide

<400> SEQUENCE: 90

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Asn Lys Ser
        35                  40                  45

Leu Leu His Ser Asn Gly Asn Thr Tyr Leu Tyr Trp Phe Leu Gln Arg
    50                  55                  60

Pro Gly Gln Ser Pro Gln Leu Leu Ile Tyr Arg Val Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Leu Thr Phe Gly Ala Gly Thr Lys
        115                 120                 125

Leu Glu Leu Lys Arg
    130

<210> SEQ ID NO 91
<211> LENGTH: 372
<212> TYPE: DNA
<213> ORGANISM: Artificial Sequence
<220> FEATURE:
<223> OTHER INFORMATION: Hu14G8VHv1

<400> SEQUENCE: 91
gaggtgaagc tggtggagtc tggcggcggc ttggtgcaac tggcggctc cctgaagctg     60 tcctgtgccg cctccggctt caccttcagc agctatacca tgtcttgggt gcgccaaacc   120
cccgagaaga ggctggagtt ggtggctgag attaataata gcggcgatac cacctactat   180
cccgataccg tgaagggccg cttcaccatt ccagagata atgctaagaa taccctgtat   240
ctgcaaatga gtagcctgaa gtctgaggat accgctatgt attattgtgc tagacattat   300
tattatggcg cggctatgg cggctggttc ttcgatgtgt ggggcaccgg caccctggtc   360
accgtgtcct ca                                                       372
```

```
<210> SEQ ID NO 92
<211> LENGTH: 372
<212> TYPE: DNA
<213> ORGANISM: Artificial Sequence
<220> FEATURE:
<223> OTHER INFORMATION: Hu14G8VHv2

<400> SEQUENCE: 92
gaggtgcaac tggtggagtc tggcggcggc ttggtgcaac ctggcggctc cctgaagctg      60
tcctgtgccg cctccggctt caccttcagc agctatacca tgtcttgggt gcgccaaacc     120
cccgagaaga ggctggagtt ggtggctgag attaataata gcggcgatac cacctactat     180
cccgataccg tgaagggccg cttcaccatt tccagagata tgctaagaa tacccctgtat    240 ctgcaaatga gtagcctgaa gtctgaggat accgctatgt attattgtgc tagacattat     300
tattatggcg gcggctatgg cggctggttc ttcgatgtgt ggggccaagg caccctggtc     360
accgtgtcct ca                                                        372

<210> SEQ ID NO 93
<211> LENGTH: 372
<212> TYPE: DNA
<213> ORGANISM: Artificial Sequence
<220> FEATURE:
<223> OTHER INFORMATION: Hu14G8VHv3

<400> SEQUENCE: 93
gaggtgcaac tggtggagtc tggcggcggc ttggtgcaac ctggcggctc cctgaagctg      60
tcctgtgccg cctccggctt caccttcagc agctatacca tgtcttgggt gcgccaaacc     120
cccgagaaga ggctggagtt ggtggctgag attaataata gcggcgatac cacctactat     180
cccgataccg tgaagggccg cttcaccatt tccagagata tgctaagaa tacccctgtat    240 ctgcaaatga atagcctgag ggctgaggat accgctgtgt attattgtgc tagacattat     300
tattatggcg gcggctatgg cggctggttc ttcgatgtgt ggggccaagg caccctggtc     360
accgtgtcct ca                                                        372

<210> SEQ ID NO 94
<211> LENGTH: 339
<212> TYPE: DNA
<213> ORGANISM: Artificial Sequence
<220> FEATURE:
<223> OTHER INFORMATION: Hu14G8VLv1

<400> SEQUENCE: 94
gatatcgtga tgacccagtc tgccccctcc ctgcctgtga cccctggcga gtccgtgtcc      60
atctcctgcc ggtccaacaa gagcctgctg cacagcaacg gcaacaccta cctgtactgg     120
ttcctgcaaa agcccggcca atcccctcaa ctgctgatct accgggtgtc caacctggcc     180
tccggcgtgc ccgataggtt ctccggaagc ggctccggca ccgccttcac cctgaagatt     240
agtagagtcg aggccgagga tgtgggcgtg tactactgta tgcaacactt ggagtacccc     300
ctgacgttcg gccaaggcac caagctggag atcaagcgt                            339

<210> SEQ ID NO 95
<211> LENGTH: 339
<212> TYPE: DNA
<213> ORGANISM: Artificial Sequence
<220> FEATURE:
<223> OTHER INFORMATION: Hu14G8VLv2

<400> SEQUENCE: 95
```

```
gatatcgtga tgacccagtc tcccctgtcc ctgcctgtga ccctggcga gcccgcctcc      60 atctcctgcc ggtccaacaa gagcctgctg cacagcaacg caacaccta cctgtactgg     120 ttcctgcaaa agcccggcca atcccctcaa ctgctgatct accgggtgtc caacctggcc    180
tccggcgtgc ccgataggtt ctccggaagc ggctccggca ccgatttcac cctgaagatt    240
agtagagtcg aggccgagga tgtgggcgtg tactactgta tgcaacactt ggagtacccc    300
ctgacgttcg gccaaggcac caagctggag atcaagcgt                            339
```

<210> SEQ ID NO 96
<211> LENGTH: 339
<212> TYPE: DNA
<213> ORGANISM: Artificial Sequence
<220> FEATURE:
<223> OTHER INFORMATION: Hu14G8VLv3

<400> SEQUENCE: 96

```
gatatcgtga tgacccagtc tcccctgtcc ctgcctgtga ccctggcga gcccgcctcc      60 atctcctgcc ggtccagcaa gagcctgctg cacagcaacg caacaccta cctgtactgg     120 ttcctgcaaa agcccggcca atcccctcaa ctgctgatct accgggtgtc caacctggcc    180
tccggcgtgc ccagtaggtt ctccggaagc ggctccggca ccgatttcac cctgaagatt    240
agtagagtcg aggccgagga tgtgggcgtg tactactgta tgcaacactt ggagtacccc    300
ctgacgttcg gccaaggcac caagctggag atcaagcgt                            339
```

<210> SEQ ID NO 97
<211> LENGTH: 19
<212> TYPE: PRT
<213> ORGANISM: Artificial Sequence
<220> FEATURE:
<223> OTHER INFORMATION: 14G8VH Signal Peptide

<400> SEQUENCE: 97

Met Asn Phe Gly Leu Ser Leu Ile Phe Leu Val Leu Val Leu Lys Gly
1               5                   10                  15

Val Leu Cys

<210> SEQ ID NO 98
<211> LENGTH: 57
<212> TYPE: DNA
<213> ORGANISM: Artificial Sequence
<220> FEATURE:
<223> OTHER INFORMATION: 14G8VH Signal Peptide

<400> SEQUENCE: 98

```
atgaatttcg gcctgagctt gattttcctg gtgctggtgt tgaagggcgt gctgtgt         57
```

<210> SEQ ID NO 99
<211> LENGTH: 20
<212> TYPE: PRT
<213> ORGANISM: Artificial Sequence
<220> FEATURE:
<223> OTHER INFORMATION: 14G8VL Signal Peptide

<400> SEQUENCE: 99

Met Arg Cys Leu Ala Glu Phe Leu Gly Leu Leu Val Leu Trp Ile Pro
1               5                   10                  15

Gly Ala Ile Gly
            20

<210> SEQ ID NO 100

```
<211> LENGTH: 60
<212> TYPE: DNA
<213> ORGANISM: Artificial Sequence
<220> FEATURE:
<223> OTHER INFORMATION: 14G8VL Signal Peptide

<400> SEQUENCE: 100
atgaggtgcc tggccgagtt cctgggcctg ctggtgctgt ggatccctgg cgccatcggc    60

<210> SEQ ID NO 101
<211> LENGTH: 330
<212> TYPE: PRT
<213> ORGANISM: Artificial Sequence
<220> FEATURE:
<223> OTHER INFORMATION: Human IgG1 heavy chain constant region

<400> SEQUENCE: 101
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 102
<211> LENGTH: 330
<212> TYPE: PRT
<213> ORGANISM: Artificial Sequence
<220> FEATURE:
<223> OTHER INFORMATION: Human IgG1 heavy chain constant region of IgG1
      G1m3 allotype

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 103
<211> LENGTH: 330
<212> TYPE: PRT
<213> ORGANISM: Artificial Sequence
<220> FEATURE:
<223> OTHER INFORMATION: Human IgG1 heavy chain constant region of IgG1
      G1m3 allotype

<400> SEQUENCE: 103

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 104
<211> LENGTH: 107
<212> TYPE: PRT
<213> ORGANISM: Artificial Sequence
<220> FEATURE:

<223> OTHER INFORMATION: Human kappa light chain constant region

<400> SEQUENCE: 104

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 105
<211> LENGTH: 106
<212> TYPE: PRT
<213> ORGANISM: Artificial Sequence
<220> FEATURE:
<223> OTHER INFORMATION: Human kappa light chain constant region

<400> SEQUENCE: 105

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 106
<211> LENGTH: 990
<212> TYPE: DNA
<213> ORGANISM: Artificial Sequence
<220> FEATURE:
<223> OTHER INFORMATION: Human IgG1 heavy chain constant region of IgG1
      G1m3 allotype

<400> SEQUENCE: 106
gcctccacca agggtccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggggga    360

```
ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag gcagccccg agaaccacag gtgtacaccc tgcccccatc ccgggaggag       720
atgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctat agcaagctca ccgtggacaa gagcaggtgg      900
cagcagggga acgtcttctc atgctccgtg atgcatgagg ctctgcacaa ccactacacg      960
cagaagagcc tctccctgtc cccgggtaaa                                      990

<210> SEQ ID NO 107
<211> LENGTH: 321
<212> TYPE: DNA
<213> ORGANISM: Artificial Sequence
<220> FEATURE:
<223> OTHER INFORMATION: Human kappa light chain constant region

<400> SEQUENCE: 107
cgaactgtgg ctgcaccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg t                                               321

<210> SEQ ID NO 108
<211> LENGTH: 318
<212> TYPE: DNA
<213> ORGANISM: Artificial Sequence
<220> FEATURE:
<223> OTHER INFORMATION: Human kappa light chain constant region

<400> SEQUENCE: 108
actgtggctg caccatctgt cttcatcttc cgccatctg atgagcagtt gaaatctgga       60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgt                                                   318

<210> SEQ ID NO 109
<211> LENGTH: 147
<212> TYPE: PRT
<213> ORGANISM: Homo sapiens

<400> SEQUENCE: 109

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30
```

```
Met Val Lys Val Leu Asp Ala Val Arg Gly Ser Pro Ala Ile Asn Val
            35                  40                  45

Ala Val His Val Phe Arg Lys Ala Ala Asp Asp Thr Trp Glu Pro Phe
 50                  55                  60

Ala Ser Gly Lys Thr Ser Glu Ser Gly Glu Leu His Gly Leu Thr Thr
 65                  70                  75                  80

Glu Glu Glu Phe Val Glu Gly Ile Tyr Lys Val Glu Ile Asp Thr Lys
                 85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
            130                 135                 140

Pro Lys Glu
145

<210> SEQ ID NO 110
<211> LENGTH: 127
<212> TYPE: PRT
<213> ORGANISM: Homo sapiens

<400> SEQUENCE: 110

Gly Pro Thr Gly Thr Gly Glu Ser Lys Cys Pro Leu Met Val Lys Val
 1               5                  10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
            35                  40                  45

Thr Ser Glu Ser Gly Glu Leu His Gly Leu Thr Thr Glu Glu Gln Phe
 50                  55                  60

Val Glu Gly Ile Tyr Lys Val Glu Ile Asp Thr Lys Ser Tyr Trp Lys
 65                  70                  75                  80

Ala Leu Gly Ile Ser Pro Phe His Glu His Ala Glu Val Val Phe Thr
                 85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
            115                 120                 125

<210> SEQ ID NO 111
<211> LENGTH: 127
<212> TYPE: PRT
<213> ORGANISM: Homo sapiens

<400> SEQUENCE: 111

Gly Pro Thr Gly Thr Gly Glu Ser Lys Cys Pro Leu Met Val Lys Val
 1               5                  10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
            35                  40                  45

Thr Ser Glu Ser Gly Glu Leu His Gly Leu Thr Thr Glu Glu Gln Phe
 50                  55                  60

Val Glu Gly Ile Tyr Lys Val Glu Ile Asp Thr Lys Ser Tyr Trp Lys
 65                  70                  75                  80
```

```
Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 112
<211> LENGTH: 138
<212> TYPE: PRT
<213> ORGANISM: Homo sapiens

<400> SEQUENCE: 112

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Ser Tyr Ser
        115                 120                 125

Thr Thr Ala Val Val Thr Asn Pro Lys Glu
    130                 135

<210> SEQ ID NO 113
<211> LENGTH: 9
<212> TYPE: PRT
<213> ORGANISM: Artificial Sequence
<220> FEATURE:
<223> OTHER INFORMATION: Transthyretin residues 89-97

<400> SEQUENCE: 113

Glu His Ala Glu Val Val Phe Thr Ala
1               5

<210> SEQ ID NO 114
<211> LENGTH: 15
<212> TYPE: PRT
<213> ORGANISM: Artificial Sequence
<220> FEATURE:
<223> OTHER INFORMATION: Potential transthyretin immunogen

<400> SEQUENCE: 114

Gly Gly Glu His Ala Glu Val Val Phe Thr Ala Gly Gly Lys Gly
1               5                   10                  15

<210> SEQ ID NO 115
<211> LENGTH: 12
<212> TYPE: PRT
<213> ORGANISM: Artificial Sequence
<220> FEATURE:
<223> OTHER INFORMATION: Potential transthyretin immunogen
```

```
<400> SEQUENCE: 115

Cys Gly Gly Glu His Ala Glu Val Val Phe Thr Ala
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Potential transthyretin immunogen

<400> SEQUENCE: 116

Glu His Ala Glu Val Val Phe Thr Ala Cys Gly Gly
1               5                   10

<210> SEQ ID NO 117
<211> LENGTH: 10
<212> TYPE: PRT
<213> ORGANISM: Artificial Sequence
<220> FEATURE:
<223> OTHER INFORMATION: 9D5 CDRH1 - Composite Chothia-Kabat

<400> SEQUENCE: 117

Gly Phe Thr Phe Ser Ser Tyr Thr Met Ser
1               5                   10

<210> SEQ ID NO 118
<211> LENGTH: 10
<212> TYPE: PRT
<213> ORGANISM: Artificial Sequence
<220> FEATURE:
<223> OTHER INFORMATION: 14G8 CDRH1 - Composite Chothia-Kabat

<400> SEQUENCE: 118

Gly Phe Thr Phe Ser Ser Tyr Thr Met Ser
1               5                   10
```